United States Patent [19]

Bray et al.

[11] Patent Number: 5,053,338
[45] Date of Patent: Oct. 1, 1991

[54] KINETIC RESOLUTION OF PYRIDAZINONES USING LIPASE

[75] Inventors: Brian L. Bray, Graham; John J. Partridge, Chapel Hill, both of N.C.

[73] Assignee: Glaxo Inc., Research Triangle Park, N.C.

[21] Appl. No.: 560,941

[22] Filed: Jul. 20, 1990

Related U.S. Application Data

[63] Continuation-in-part of Ser. No. 402,179, Sep. 1, 1989, abandoned.

[51] Int. Cl.$^5$ .............................................. C12P 41/00
[52] U.S. Cl. .................................. 435/280; 435/122; 435/198; 544/239
[58] Field of Search ...................... 435/280, 122, 197; 544/239

[56] References Cited

PUBLICATIONS

Kalaritis, Panos et al., Kinetic Resolution of 2-Substituted Esters Catalyzed by a Lipase Ex., J. Org. Chem. 1990, 55, 812-815.

Whitesides, George M., Enzymes as Catalysts in Synthetic Organic Chemistry, vol. 24, No. 8, Aug. 1985, 617-718.

*Primary Examiner*—Douglas W. Robinson
*Assistant Examiner*—Sandra Saucier
*Attorney, Agent, or Firm*—David J. Levy

[57] ABSTRACT

A kinetic resolution of pyridazinones of the following formula (A):

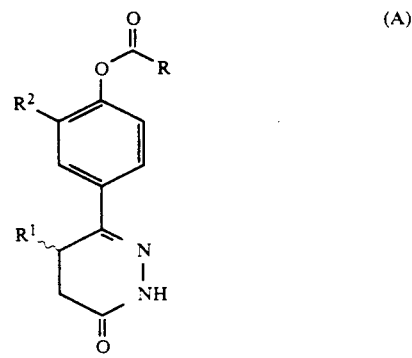

where $R^1$ is alkyl by enzymatic hydrolysis results in good optical purity of the phenolic product. This is significant considering the distance in the molecule (A) from the C-5 chiral center to the site of hydrolysis.

15 Claims, No Drawings

KINETIC RESOLUTION OF PYRIDAZINONES USING LIPASE

This application is a continuation-in-part of Ser. No. 402,179, filed Sept. 1, 1989, now abanonded.

BACKGROUND OF THE INVENTION

In co-pending U.S. Ser. No. 07/402,179 filed Sept. 1, 1989, now abandoned there are disclosed pyridazinones useful in treating persons diagnosed as having congestive heart failure of the following formula (I):

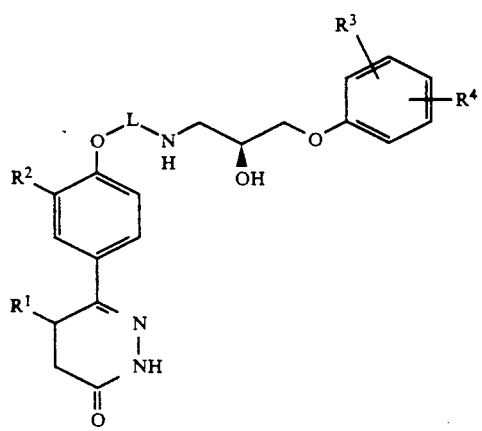

wherein:
$R^1$ is H or lower alkyl;
$R^2$ is H, halogen, $CF_3$, CN, lower alkyl or lower alkoxy;
L is an amide-containing alkylene chain or an alkylene chain and:
$R^3$ and $R^4$ represent a variety of substituents.

A method of making compounds of formula (I) involves reaction of a phenol of the following formula (B):

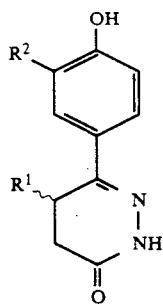

wherein $R^1$ and $R^2$ are as defined for formula (I) and the wavy line at the 5-position of the pyridazinone ring indicates that the bond could be up or down or a mixture of the two such enantiomers. An object of the present invention is to provide a method of obtaining the compound formula (B) enriched in one or the other of such enantiomers.

Publications relevant to the art of kinetic resolution include P. Kalaritis et al in J. Org. Chem., 1990, 55, pp 812–815, George M. Whitesides in Angewandte Chemie Vol. 24, No. 8, August 1985, pp 617–638 and European Patents 325,954 and 325,971 to John J. Partridge et al.

SUMMARY OF THE INVENTION

A process of enriching 6-(4-hydroxyphenyl)-pyridazinone having chirality in the pyridazinone ring by the enzymatic kinetic hydrolysis of the ester.

DETAILED DESCRIPTION OF THE INVENTION

The invention relates to a method of resolving isomers by kinetic resolution to obtain a product which has an increased amount, i.e. enantiomeric excess or optical purity greater than 0%, of one of the two isomers. In more detail, the method concerns a method of resolving a mixture of 5R and 5S pyridazinone esters of the following formula (A):

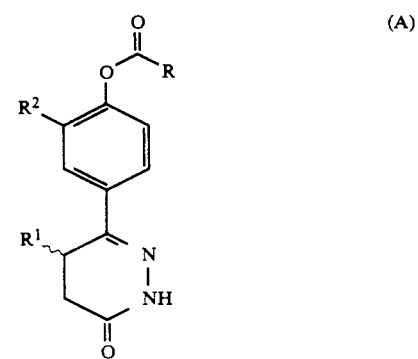

wherein:
$R^1$ represents lower alkyl;
$R^2$ represents hydrogen, halogen, trifluoromethyl, cyano, lower alkyl or loweralkyloxy; and
R represents alkyl,
which comprises reacting said ester mixture with a hydrolytic enzyme and recovering i) a mixture of esters of formula (A) optically enriched in one of the 5R or 5S enantiomers and ii) a mixture of the phenols of the following formula (B) optically enriched in the other of the 5R or 5S enantiomers:

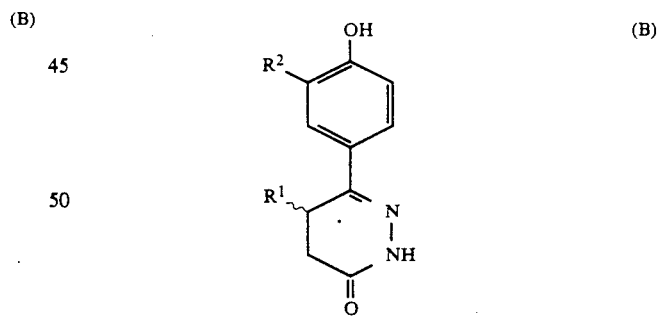

In particular, the method of the invention may be used to produce esters of formula (A) enriched in the 5S isomers and phenols of formula (B) enriched in the 5R phenol. The kinetic hydrolysis is conducted until a satisfactory level of completion; at just over 0%, the initial hydrolysis is heavily enriched in the 5R phenol since 5R reacts much faster than 5S while 100% hydrolysis results in 0% enrichment since all ester has been converted to phenol. Preferably, the kinetic enzymatic hydrolysis of the invention is conducted to about 40 to 60% completion. The reaction may be conducted in a ratio of about 100 to 10,000 units of enzyme per millimole of ester mixture (A), e.g. a racemic mixture, at a temperature of about 0° to 40° C. The reaction may be conducted in an aqueous solution with an organic cosolvent such as an ether, e.g. tetrahydrofuran or dioxane, an alkanol such as methanol or ethanol, a ketone such as acetone or methyl ethyl ketone or a halogenated hydrocarbon such as dichloroethane. The enzyme used in the invention process is a hydrolytic enzyme such as lipase, including an esterase. Such lipases may be obtained from sources such as Sigma Chemical Co. of St. Louis, Mo., U.S.A. and may be derived from biological systems such as Pseudomonas.

In formula (A), R is preferably an alkyl of less than 20 carbons such as less than 4 carbons, e.g. —CH$_3$ or —CH$_2$CH$_2$CH$_3$, and R$^2$ is hydrogen. R$^1$ may be methyl. The ester (A) may itself be obtained from the phenol (B) by reaction of the phenol with an acid chloride or anhydride e.g. acetyl chloride or acetic anhydride. The phenol mixture product (B) of the reaction of the invention may be further enriched by esterification with a source of —C(O)R and reacted again with a hydrolytic enzyme to yield a mixture of phenols (B) having a greater optical purity.

The unreacted ester mixture of formula (A) recovered in the reaction of the invention may be recycled by chemical hydrolysis to recover the corresponding phenol mixture of formula (B) followed by acid catalyzed epimerization at C-5. The process of the invention is the surprising result of optical enrichment at a site, i.e., the C-5 position of the pyridazinone, which is 6 atoms removed from the hydrolytic reaction. Thus the influence of the enzyme is surprisingly conveyed over a considerable molecular distance.

The pharmaceutical final products for which the process of the process of the present invention is useful are 4,5-dihydro-3(2H)-pyridazinones of the following formula (I):

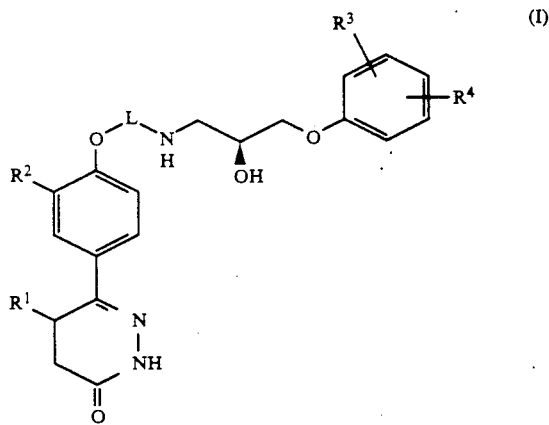

wherein:
R$^1$ represents hydrogen or lower alkyl;
R$^2$ represents hydrogen, halogen, trifluoromethyl, cyano, lower alkyl, or lower alkyloxy;
L represents a linking moiety of the formula (II) or (III):

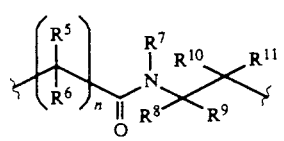

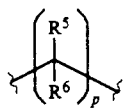

in which:
R$^5$–R$^{11}$ represent, independently, hydrogen or lower alkyl;
n represents the integer 1,2 or 3;
p represents the integer 2,3,4,5 or 6;
R$^3$ and R$^4$ represent, independently, hydrogen, alkyloxy, morpholino, cyano, halogen, trifluoromethyl, alkyl, alkyl sulfonyl, alkyloxyalkyl, cycloalkylalkyloxyalkyl, nitro, hydroxy, alkenyloxy, amino or amino substituted by one or two lower alkyl groups.

As used herein, "lower alkyl" per se or as part of another group such as lower alkyloxy may be about 1 to 3 carbons, straight or branched chain; similarly, "alkyl" may be of about 1 to 6 carbons, straight or branched chain; "cycloalkyl" may be of about 3 to 7 carbons; "independently" indicates that members, where two or more are present, need not be identical e.g. the definitions of R$^3$ and R$^4$ and the various possibilities for R$^5$ when n or p are 2 or more; "halogen" is fluoro, chloro, bromo or iodo; the L group is attached as shown in the definitions i.e. the carbon carrying R$^5$ and R$^6$ in formula (II) is attached to the left most oxygen of formula (I); the wavy lines in formulae (II) and (III) indicate the bond of attachment of L; and morpholino may be attached via the nitrogen or any ring carbon.

Particular products of this invention are those of formula (I) with one or more of the following definitions: R$^1$ is hydrogen or a methyl group; R$^2$ is hydrogen or a chlorine atom; L is the linking group (II); n is 1, R$^5$, R$^6$, R$^7$, R$^8$, and R$^9$ are hydrogen; and are methyl groups; R$^3$ is hydrogen and R$^4$ is a cyano, chlorine, or methyl substituted at position 2 of the phenyl ring; R stereochemistry at the 5-position of the pyridazinone ring.

The compounds of formula (I) contain a basic nitrogen atom and hence can form pharmaceutically acceptable acid addition salts. A wide variety of acids may be employed to form such salts and representative examples of such acids include: inorganic acids, e.g. hydrochloric acid, hydrobromic acid, hydroiodic acid, phosphoric acid, nitric acid, and sulfuric acid, and organic acids, e.g. maleic acid, fumaric acid, acetic acid, benzoic acid, p-toluenesulfonic acid, tartaric acid, citric acid, succinic acid, lactic acid and propionic acid. These acid addition salts are prepared by conventional methods. Compounds of formula (I) may also exist as a solvate, e.g. a hydrate or hemihydrate and such are within the scope of the invention.

Several of the compounds of formula (I) have one or more asymmetric carbon atoms in their structure, in addition to the carbon bearing the hydroxy of the 2-hydroxypropyl group of formula (I), and consequently they may exist in different optical isomeric forms or mixtures, e.g. racemates or mixtures of diastereomers. Thus when R$^1$ is a methyl group, there is an asymmetric carbon atom in the 4,5-dihydro-3(2H)-pyridazinone ring, and, depending upon the definition of R$^5$, R$^6$, R$^8$, R$^9$, and additional asymmetric carbon atoms may be present in the linking group, L. Enantiomeric forms and mixtures of such forms may b  btained separately by application of methods of resolution known to those skilled in the art such as, for example, salt formation with an optically active acid followed by selective crystallization or chiral derivatization followed by selective crystallization or silica gel chromatography. Alternatively, optically active starting material(s) may be employed in the synthesis. All stereoisomeric forms of the compounds of formula (I), including mixtures of diastereomers, pure diastereomers, enantiomers and mixtures thereof, are understood to be within the scope of this invention, except compositions with only the stereochemistry opposite to that shown at the carbon bearing the hydroxy moiety depicted in formula (I).

The compounds of formula (I) in which the linking moiety L is of the formula (II) may be prepared as shown in Scheme I.

acetyl chloride, pivaloyl chloride, or isobutoxycarbonyl chloride in the presence of a proton accepter and an inert solvent. The acyl imidazoles may be prepared by reacting the compound of the formula (IV) (X©OH) with N,N'-carbonyldiimidazole. Suitable proton accepters include both organic bases such as triethylamine or 4-dimethylaminopyridine and inorganic bases such as anhydrous potassium carbonate. Suitable solvents for forming reactive derivatives from (IV) where X=OH include diethyl ether, tetrahydrofuran, aromatic hydrocarbon solvents such benzene or toluene, methylene chloride, and CH3CN. Thus, X may specifically be hydroxy, chloro, acetoxy, propionoxy, pivaloxy, or imidazole; or 4-nitrobenzyl.

The compounds of formula (IV) are either already known or may be prepared by known methods, for

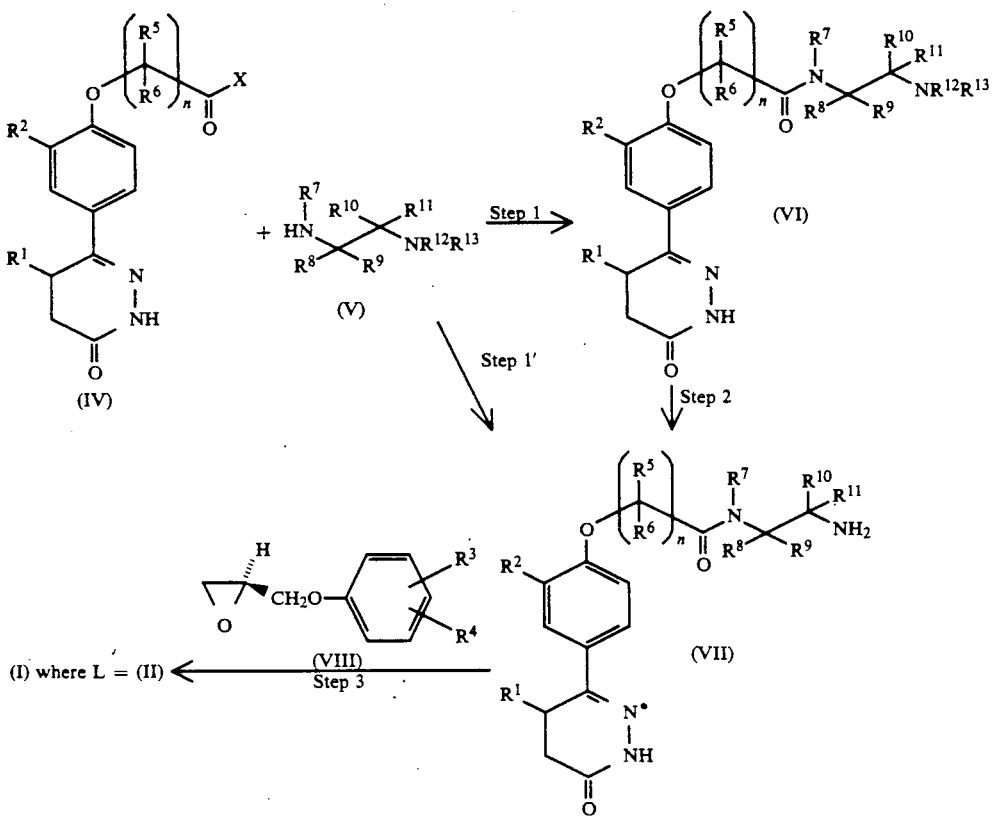

Scheme I

In Scheme I, n and the various R groups, except $R^{12}$ and $R^{13}$, and n are as defined above for formula (I). In the compound of formula (IV), X is a leaving group such as hydroxy whereby the starting material is a carboxylic acid. Alternatively, the compound of formula (IV) where X is OH may be converted to a suitably reactive derivative which is then reacted with an amine of formula (V). Suitable reactive derivatives of the carboxylic acid (IV) include: acid halides where X is halogen, such as the acid chloride; mixed anhydrides of the carboxylic acid with another organic acid, such as acetic acid, propionic acid, or pivalic acid whereby X is —OCOR where R is an organic moiety such as alkyul; acyl imidazoles; and active esters of carboxylic acid, such as the 4-nitrophenyl ester. With the exception of the acyl imidazole, these reactive derivatives can be prepared by treating the carboxylic acid with a suitable halogen compound, such as thionyl or oxalyl chloride, example as described in European Patent application 178,189 published Apr. 16, 1986.

In the compounds of formula (V), $R^{12}$ represents hydrogen and $R^{13}$ represents any of several monovalent amine protecting groups including, but not limited to carbamates, or N-benzyl derivatives, e.g. benzyl, or $R^{12}$ and $R^{13}$ together represent a divalent amine protecting group such as a phthalimide. For detailed examples of the use and removal of these amine protecting groups see T. W. Greene, *Protective Groups in Organic Synthesis*, John Wiley & Sons, 1981, pp. 218–323.

Depending upon the definition of $R^8$, $R^9$, $R^{10}$ and $R^{11}$, an amine protecting group $R^{13}$ or $R^{12}$ and $R^{13}$ may not be necessary. In those cases, Step 2 of Scheme I is unnecessary and the intermediate (VII) is prepared directly from (V) via Step 1' by the methods defined for Step 1. This is the case when $R^{10}$ and $R^{11}$ are methyl groups whereby there is no further reaction of the second amino group in (V).

The amines of formula (V) are commercially available or may be prepared by conventional methods. For example, see the *Journal of Medicinal Chemistry* 31, 898-901 (1988).

Steps 1 and 1' in Scheme I are coupling reactions and may be executed by treating a mixture of compounds (IV) and (V) in the presence of an inert solvent with suitable dehydrating agents including diethylcyanophosphonate and dicyclohexylcarbodiimide. Although the reaction can be carried out over a wide range of temperatures, it is most convenient to effect the reaction with diethylcyanophosphonate at 0° C. to 75° C. Suitable solvents for the coupling reaction are tetrahydrofuran, CH$_3$CN, benzene, toluene, methylene chloride, chloroform, and DMF. The preferred solvent when diethylcyanophosphonate is used as the dehydrating agent is DMF.

When X is other than OH in formula (IV), the reaction between (IV) and the amine of formula (V) is preferably effected in the presence of an inert solvent, such as aromatic hydrocarbons, e.g. benzene or toluene, ethers, such as diethyl ether or tetrahydrofuran, and halogenated solvents such as methylene chloride. The reaction may be carried out over a wide range of temperatures, but the preferred temperature range is 0° C. to 25° C. Within this temperature range, the time required for the reaction will generally range from 15 min to 6 hrs.

Step 2 of Scheme I, removal of the amine protective group R$^{12}$ or R$^{12}$ and R$^{13}$, is executed under conditions appropriate to the particular amine protective group. A preferred amine protective group is the tert-butoxycarbonyl group. When R$^{12}$ in Scheme I represents the tertbutoxycarbonyl group, Step 2 is effected by treating the compound of formula (VI) with an acid solution which may be either a mineral acid such as hydrochloric acid, hydrobromic acid, or sulfuric acid or an organic acid such as p-toluenesulfonic acid or trifluoroacetic acid. A wide range of solvents may be used for removal of tert-butoxycarbonyl as long as the solvent is stable to acids and does not react with the amine product, (VII). Suitable solvents include the halogenated hydrocarbons such as methylene chloride chloroform and aromatic solvents such as benzene and toluene. The reaction maybe run over a wide range of temperatures, but is generally carried out in the temperature range of 0° C. to 25° C. The time required for the reaction may be 15 min to 2 hrs and depends upon the solvent and temperature of the reaction. Removal of other amine protecting groups may be as set forth in the description below of Step 2 of Scheme III.

Step 3 in Scheme I is effected by reacting an amine of formula (VII) with an epoxide of the formula (VIII). Epoxides of the formula (VIII) are either known compounds or can be prepared by conventional procedures well known to those skilled in the art of organic synthesis. In known beta-adrenergic antagonists one of the enantiomers at the carbon bearing the hydroxyl group (namely the enantiomer having the S-configuration) has the property of antagonizing beta-adrenergic activity (see B. G. Maine and H. Tucker, *Progress in Medicinal Chemistry*. Vol. 22, p 124). It is thus of particular utility to utilize in Step 3 epoxides of the formula (VIII) having the S-configuration at the asymmetric carbon, since these epoxides will yield structures of the formula (I) having the S-configuration at the carbon bearing the hydroxyl group.

The desired S-epoxides are prepared as shown in Scheme II using the procedures described by K. B. Sharpless, et al in the *Journal of Organic Chemistry* 1989, 54, 1295-1304.

Scheme II

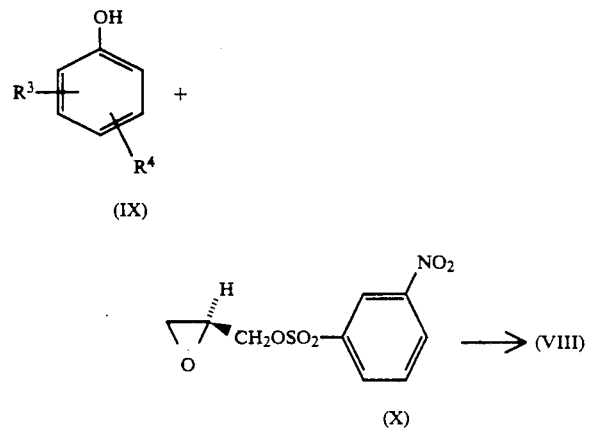

In Scheme II, R$^3$ and R$^4$ are as defined above for formula (I). In Scheme II, a salt of the phenol of formula (IX) is reacted with a sulfonate of formula (X) at 25° to 75° C. to yield the epoxide (VIII) as the S-enantiomer. Suitable salts include the sodium and potassium salts. The (2S)-(+)- glycidyl 3-nitrobenzenesulfonate shown in Scheme II is commercially available from the Aldrich Chemical Company or may be prepared by the methods cited in the Sharpless et. al. reference given above. The phenols of formula (IX) shown in Scheme II are known compounds that are commercially available or can be prepared by conventional methods.

A wide variety of solvents may be employed in Step 3 of Scheme I, provided that the solvent must be inert with respect to the amines (VII), epoxides (VIII), and products (I). Suitable solvents for Step 3 include alcohols such as CH$_3$OH, ethanol, or isopropanol; aromatic hydrocarbon solvents such as benzene or toluene, and ethers such as tetrahydrofuran or dioxane. The reaction in Step 3 may be run over a wide range of temperatures, but is generally conducted in the range of 25° C. to 100° C. The time required for the reaction of Step 3 is dependent upon temperature and the nature of the substituents R$^{10}$ and R$^{11}$, however, a time span of 3-24 hrs is usually sufficient for completion of the reaction.

The compounds of formula (I) in which L is a group of the formula (III) are prepared as shown in Scheme III.

Scheme III

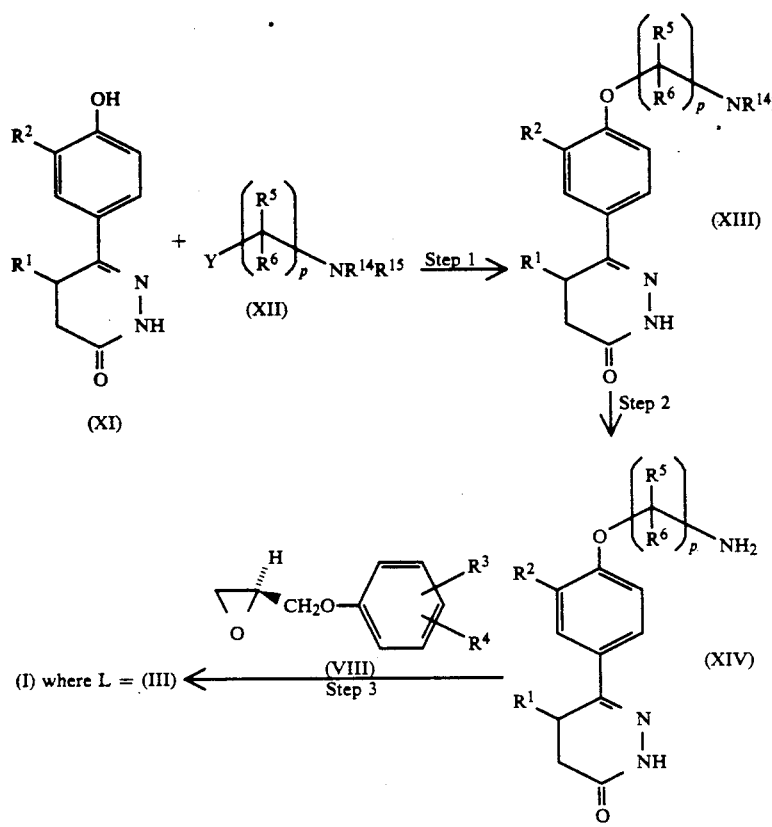

In Scheme III, $R^1$, $R^2$, $R^5$, $R^6$ and p are as defined in formula (I).

The phenols of formulas (XI) employed as starting materials in Scheme III are either already known or may be prepared by known methods, for example as described in the Journal of Medicinal Chemistry, 17, 273, (1974) or in European Patent application 178,189.

The compounds of formula (XIII) represent protected alkylamines with a leaving group, Y, at one end of the chain that is reactive toward displacement by nucleophiles. Suitable Y groups include halogen, p-toluenesulfonate esters, p-nitrobenzenesulfonate esters, methanesulfonate esters, and trifluoromethanesulfonate esters. In Scheme III, $R^{14}$ and $R^{15}$ are as defined above for $R^{12}$ and $R^{13}$. Suitable amine protecting group $R^{14}$ or $R^{14}$ and $R^{15}$ include, together with the nitrogen to which they are attached, a phthalimide group, carbamates, and N-benzylated amines. The compounds of formula (XII) are either known or may be prepared from the corresponding halo- or hydroxyalkylamines by conventional methods well known to those skilled in the art.

Step 1 in Scheme III is effected by reacting a phenol of the formula (XI) with a compound of the formula (XII) in the presence of a suitable base and appropriate solvent to give compounds of formula (XIII). Bases which may be used in Step 1 include sodium hydride, potassium carbonate, potassium t-butoxide, and similar non-nucleophilic basic reagents.

A wide variety of solvents may be used in Step 1 of Scheme III with the only restriction being that the solvent be inert toward starting materials (XI) and (XII) as well as to the basic reagent and the product (XIII). Suitable solvents include DMF, dimethylsulfoxide, aromatic hydrocarbon's such as benzene or toluene, and ethers such as tetrahydrofuran. Step 1 may be conducted over a wide temperature range, with the preferred temperature being about 75° C. to 125° C. The preferred conditions for effecting Step 1 of Scheme III is to use anhydrous, powdered potassium carbonate (10% excess) as the base, dimethylformamide as the solvent, and a temperature of 100° C. Under these conditions Step 1 is completed in 2-6 hrs.

The nature of the reaction conditions for Step 2 of Scheme III are dependent upon the amine protecting group $R^{14}$ or $R^{14}$ and $R^{15}$, that has been employed. If the amine protective group is a carbamate moiety, such as the tert-butoxycarbamoyl group, it may be removed under acid hydrolysis conditions. Reaction conditions and suitable acids are the same as those described earlier for Step 2 of Scheme I. If the amine protective group is a phthalimide group, the protecting group is conveniently removed by treatment of a compound of formula (XIII) with hydrazine in a suitable solvent. Solvents that may be used for this reaction include alcohols, e.g. ethanol or isopropanol, ethers such as tetrahydrofuran, $CH_3CN$, or aromatic hydrocarbon solvents such as benzene or toluene. The reaction may be executed over a wide temperature range, but the preferred temperature range is about 25° C. to 100° C. If the protecting group in formula (XII) is an N-benzylated amine, then the removal of the protection group (Step 2) in Scheme III is conveniently accomplished by catalytic reduction. Suitable catalysts for this reaction include platinum or palladium supported on activated charcoal. The reaction is carried out under a pressure of 1-3 atmospheres of hydrogen in the temperature range of about 25°–70° C.

Step 3 in Scheme III is carried out by reacting the amine (XIV) with an epoxide of the formula (VIII) as described for Step 3 of Scheme I.

An alternative method that has been employed to prepare compounds of formula (I) in which the L group is (II) is shown in Scheme IV below.

Scheme IV

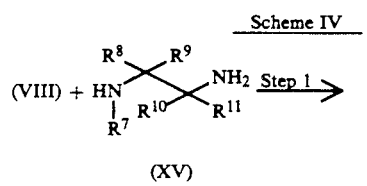

(XV)

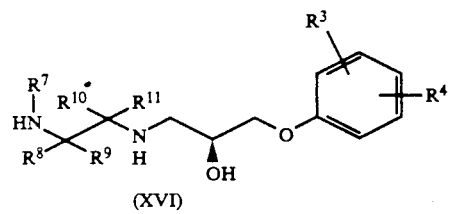

(XVI)

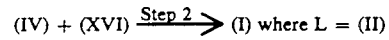

In Scheme IV all R groups are as previously defined for formula (I). Step 1 in Scheme IV is executed under conditions as previously described for Step 3 of Scheme I and Step 2 of Scheme IV is effected as described for Step 1 in Scheme I In addition, various compounds of formula (XVI) are known as seen in U.S. Pat. No. 4,608,383. The method shown in Scheme IV for the preparation of compounds of formula (I) with L=(II) is most advantageously employed when $R^7$–$R^{11}$ are all hydrogen or when $R^8$=$R^9$=$CH_3$ and $R^{10}$=$R^{11}$=H.

Specific Compounds

Specific examples of compounds of formula (I) where $R^1$ is $CH_3$ and $R^2$, $R^5$, $R^6$, $R^7$, $R^8$ and $R^9$ are hydrogen as set forth in Table I.

TABLE I

| | Formula (I) $R^1$ = methyl; $R^2$, $R^5$, $R^6$, $R^7$, $R^8$ and $R^9$ = H | | | | |
|---|---|---|---|---|---|
| Example | L | n | $R^{10}$,$R^{11}$ | p | $R^3$,$R^4$ |
| 1 | II | 1 | H,H | — | H,H |
| 2*** | II | 1 | H,H | — | 2-CN,H |
| 3 | II | 1 | H,H | — | 2-CH₃,H |
| 4 | II | 1 | H,H | — | 2-Cl,H |
| 5 | II | 1 | H,H | — | 2-(N-morpholino),H |
| 6 | II | 1 | H,H | — | 4-CH₂CH₂OCH₃,H |
| 7 | II | 1 | H,H | — | 4-CH₂CH₂OCH₂-cyclopropyl,H |
| 27* | II | 1 | H,H | — | 2-CN,H |
| 28** | II | 1 | H,H | — | 2-CN,H |
| 8 | II | 1 | CH₃,CH₃ | — | H,H |
| — | II | 1 | CH₃,CH₃ | — | 2-CH₃,H |
| 9 | II | 1 | CH₃,CH₃ | — | 2-CN,H |
| 10 | II | 1 | CH₃,CH₃ | — | 2-Cl,H |
| 29* | II | 1 | CH₃,CH₃ | — | 2-CN,H |
| 30** | II | 1 | CH₃,CH₃ | — | 2-CN,H |
| 11 | II | 3 | H,H | — | H,H |
| 12 | III | — | — | 3 | H,H |

*S-configuration at carbon bearing $R^1$
**R-configuration at carbon bearing $R^1$
***Mixture of R and S configuration at carbon bearing $R^1$ Further compounds of formula (I) where $R^1$ is hydrogen and $R^2$, $R^5$, $R^6$, $R^7$, $R^8$, and $R^9$ are hydrogen as set forth in Table II.

TABLE II

| | Formula (I) $R^1$, $R^2$, $R^5$, $R^6$, $R^7$, $R^8$ and $R^9$ = H | | | | |
|---|---|---|---|---|---|
| Example | L | n | $R^{10}$,$R^{11}$ | p | $R^3$,$R^4$ |
| 13 | II | 1 | H,H | — | H,H |
| 31 | II | 1 | H,H | — | 2-CN,H |
| 14 | II | 1 | CH₃,CH₃ | — | 2-CN,H |
| 15 | II | 1 | CH₃,CH₃ | — | 2-CH₃,H |
| 16 | II | 1 | CH₃,CH₃ | — | 2-Cl,H |
| 34 | II | 1 | CH₃,CH₃ | — | 2-CN,5-Cl |
| 17 | II | 3 | H,H | — | H,H |
| 32 | II | 3 | CH₃,CH₃ | — | 2-CN,H |
| 33 | II | 3 | H,H | — | 2-CN,H |
| 18 | III | — | — | 3 | H,H |

Further compounds of formula (I) where $R^1$, $R^5$, $R^6$, $R^7$, $R^8$ and $R^9$ are hydrogen and $R^2$ is chloro are as set forth in Table III.

TABLE III

| | Formula (I) $R^1$, $R^5$, $R^6$, $R^7$, $R^8$, and $R^9$ = H; $R^2$ = Cl | | | | |
|---|---|---|---|---|---|
| Example | L | n | $R^{10}$,$R^{11}$ | p | $R^3$,$R^4$ |
| 26 | III | — | — | 3 | 2-CH₃,H |
| 25 | III | — | — | 3 | 2-Cl,H |
| 24 | III | — | — | 3 | 2-CN,H |
| 19 | II | 1 | H,H | — | H,H |
| 35 | II | 1 | H,H | — | 2-CN,H |
| 20 | II | 1 | CH₃,CH₃ | — | 2-CN,H |
| 21 | II | 1 | CH₃,CH₃ | — | 2-CH₃,H |
| 22 | II | 1 | CH₃,CH₃ | — | 2-Cl,H |
| 37 | II | 1 | CH₃,CH₃ | — | 2-NO₂,H |
| 38 | II | 1 | CH₃,CH₃ | — | 2-CF₃,H |
| 39 | II | 1 | CH₃,CH₃ | — | 2-CN,5-Cl |
| 40 | II | 1 | CH₃,CH₃ | — | 3-Cl,4-Cl |
| 41 | II | 1 | CH₃,CH₃ | — | 2-Cl,3-Cl |
| 36 | II | 1 | H,CH₃ | — | 2-CN,H |
| 23 | II | 3 | H,H | — | H,H |
| 43 | II | 3 | H,H | — | 2-CN,H |
| 42 | II | 3 | CH₃,CH₃ | — | 2-CN,H |
| 44 | II | 3 | CH₃,CH₃ | — | 2-Cl,H |
| 45 | II | 3 | CH₃,CH₃ | — | 2-CH₃,H |
| 46 | II | 3 | CH₃,CH₃ | — | 2-CN,5-Cl |

Further compounds of formula (I) wherein $R^1$ is hydrogen, $R^2$ is chloro, L is (III), p is 3 and the carbon of L bearing the methyl groups is next to the propanolamine nitrogen.

TABLE IV

| | Formula (I) $R^1$ = H; $R^2$ = Cl | |
|---|---|---|
| Example | L = (III) | $R^3$,$R^4$ |
| 47 | —CH₂CH₂ C(CH₃)₂— | H,H |
| 48 | —CH₂CH₂ C(CH₃)₂— | 2-CN,H |
| 49 | —CH₂CH₂ C(CH₃)₂— | 2-Cl,H |

Pharmacology

The efficacy of compounds of formula (I) as both inotropic and beta-andrenergic blocking agents can be evaluated and measured using pharmacological methods known in the art or as described in detail below based on similarly established methodologies.

1. Rat Aorta Protocol

It has been shown by R. F. Kauffman et.al. in *J. of Pharmacol. Exp. Ther.* 242:864–872 (1987) that inotropic agents such as milrinone and enoximone produce marked relaxation of rat aorta. Such vasorelaxation appears to be related to inhibition of the phosphodiesterase (PDE) isozyme related to the cardiac sarcoplasmic reticulum. Thus, relaxation of rat aorta can be used as a screen to eliminate compounds which are not PDE inhibitors prior to testing for actual inotropic activity.

Rings of rat aorta (endothelium removed) were prepared for the measurement of isometric force in isolated tissue organ chambers essentially as previously described by T. J. Rimele et al in the *Journal of Pharmacol. Exp. Ther.* 245:102-111 (1988). The experimental portion of the protocol began with the addition of methylene blue ($1 \times 10^{-5}$M) and propranolol ($1 \times 10^{-6}$M) to each organ chamber to inhibit basal cGMP accumulation due to soluble guanylate cyclase and beta-adrenoceptors. Phenylephrine ($1 \times 10^{-7}$M) was then added and the rings were allowed to obtain a stable contractile response after which time, the test compound was added in a cumulative fashion. The relaxation induced by each concentration of the test compound was expressed as a percentage of the maximal relaxation produced by nitroprusside ($1 \times 10^{-4}$M) The results were graphically represented as a plot of the percentage relaxation vs. the negative log of the molar concentration of the test compound. The $IC_{50}$ (concentration of test compound which produced a relaxation equivalent to 50% of the maximal relaxation induced by nitroprusside) was determined for each tissue. The $IC_{50}$ for the compound of Example 19 was 0.34 micromolar with the maximal response being 100% at the highest dose tested (100 micromolar).

2. Anesthetized Dog

Inotropic effects were evaluated in barbiturate-anesthetized dogs by differentiating left intraventricular pressure. This procedure was carried out essentially as described by M. K. Grizzel et al in the FASEB Journal, Vol. 3, page 1039, abstract 4728 (1989). Purpose breed mongrel dogs (14-20 kg) of either sex were anesthetized with a mixture of sodium pentobarbital (15 mg/kg) and sodium barbital (300 mg/kg) i.v., intubated with a cuffed endotracheal tube and ventilated with a respirator (Harvard Apparatus, model 613, South Natick, Mass.) with room air (22 rpm,10-12 ml/kg/stroke). A 5F pressure transducer (Millar Instruments, Mikkro-tip Houston, Tex.) was inserted through the right carotid artery into the left ventricle to monitor intraventricular pressure. The left ventricular pressure signal was differentiated (using a 100 Hz low pass differential amplifier, Gould Inc., Cleveland, Ohio) to obtain its maximal rate of rise (+dP/dt), and used to trigger a biotach amplifier to record heart rate. Cardiac output was determined via thermodilution with a Spectramed computer (Starcom, Oxnard, Calif.) and a 5F Swan Ganz catheter which was inserted into the right jugular vein and positioned in the pulmonary artery. The femoral artery was cannulated for monitoring arterial blood pressure with a pressure transducer (Micron model MP15D, Simi Valley, Calif.). A lead II electrocardiogram was measured using subcutaneous electrodes. Following surgery and instrumentation, each dog was placed in the left lateral decubitus position for the remainder of the experiment, and allowed to stabilize for 45-60 min before starting the experimental protocol. Rectal temperature was monitored and maintained at 37°-38° C. with a heating pad (Baxter Health Care model K20, McGaw Park, Ill.). All variables were recorded using a Gould 3800S physiograph.

Isoproterenol (0.1-0.5 mg/kg) was injected i.v. into the cephalic vein at 10 min intervals except for when the test drug infusion was begun. Four of these initial injections were made to establish the baseline response. Ten min after the forth isoproterenol injection an infusion of test compound was started at 0.01 micromol/kg/10 min after 10 min of test drug infusion an isoproterenol injection was made and the dose rate of test compound was increased. This process was continued up to a dose of test compound ranging from 300 to 10,000 micromol/kg total cumulative dose. Inhibition of the isoproterenol responses on contractibility (dP/dt), heart rate and diastolic blood pressure were determined at each dose of test compound. The inotropic effect of each compound was determined by comparing the level of dP/dt at the end of each 10 min period to that of the level of dP/dt just prior to the infusion of test compound. The ED50s were determined by a 2 point interpolation of the responses obtained that were just below and above 50% inhibition of the isoproterenol response or a 50% increase in dP/dt. Data are expressed in nanomol/kg.

Inotropic effects of the compounds were determined by changes in the baseline dP/dt whereas the beta-blocking effects of the compounds were determined by quanitating inhibition of the dP/dt response to isoproterenol. The compound of the invention of Example 19 showed an inotropic $ED_{50}$ of 114 nanomoles/kg, compared to a baseline established prior to drug infusion and an $ED_{50}$ for inhibition of the isoproterenol response of 469 nanomoles/kg. Further, as opposed to many prior inotropic agents which show partial beta agonism whereby the inotropic effects can be prevented by infusion of atenolol, the compound of formula (I) produced in Example 19 showed inotropic effects which were not blocked by atenolol. In addition, many other inotropic agents whose inotropic effects are not prevented by atenolol are phosphodiesterase inhibitors which do not have beta blocking properties.

3. Guinea Pig Left Atria Test

Male Hartley guinea-pigs (300-400 grams) were sacrificed by cervical dislocation or carbon dioxide asphyxiation. The hearts were immediately removed and placed in oxygenated Krebs-Henseleit buffer (composition (millimolar): $Na^+$143, $K^+$5.9, $Ca^{++}$1.25, $Mg^{++}$1.2, $Cl^-$128, $HCO_3^-$25, $SO_4^{--}$1.2, $H_2PO_4^-$1.0, and D-glucose 10). Left atria were dissected away from the remainder of the heart and mounted on holders against platinum punctuate electrodes. The mounted atria were placed in tissue baths maintained at 31° C. and oxygenated with 95% $O_2$-5% $CO_2$ under 1.0 gram resting tension. The atria were stimulated through the punctuate electrode and an external platinum electrode at the threshold voltage plus thirty percent, one Hertz frequency and five to ten milliseconds duration. Contractions were detected with a force displacement transducer and recorded on a physiograph.

The atria were allowed to equilibrate for at least one-half hour before the experimental compounds were added to the tissue baths. Propranolol (1.0 micromolar) and phentolamine (1.0 micromolar) were added to the buffer solution in the tissue baths to eliminate any effects of endogenous catecholamine release. Propranolol and phentolamine were added at least thirty min prior to the addition of the test compounds. During the equilibration period, the buffer solution was removed and replaced frequently. Phentolamine and propranolol were immediately re-introduced to the tissue baths after refilling with buffer.

Direct effects of the test compounds on the force of atrial contraction were observed and recorded after addition of the compounds to the tissue bath. Test compounds were added in concentrations from 1.0 to 100 micromolar in ten-fold increments (1.0, 10, 100 micromolar) with an additional concentration of 300 micromolar. Atria were exposed to each concentration of the test compounds until a constant response was observed. After a constant response was observed with the highest concentration (or five min in the absence of a response), forskolin was added in the presence of the test compound. Forskolin was added in ten-fold increments from 0.1 to 100 micromolar. Responses to the test compounds and forskolin were expressed as a percentage of the maximal response to forskolin. $EC_{50}$ values for the test compounds were calculated as the concentration of the compound necessary to produce an inotropic response half that of the maximal response produced by the test compound. For the compound produced in Example 19 the maximal response was 83% at 100 micromolar with an $ED_{50}$ of 9 micromolar concentration.

4. Beta Adrenoceptor Binding Assays:

Because of its receptor density rat brain cortices were used as the source of membrane vesicles to be used in the receptor binding assays. Freshly excised cortexes were homogenized in 20 volumes (w/v) 50 mM TRIS HCl Buffer (pH 7.5), with a glass/Teflon homogenizer following the procedure previously described by T. J. Rimele in J. Pharmacol. Exp. Ther. 239: 1-8, 1986. Beta-1 adrenoceptor binding activity was determined following methods described by M. H. Randall, et al, J. Med. Chem. 20: 1090-1094, 1977, and J. Homberger, et al in Mol. Pharmacol. 20: 453-469, 1981. The incubation mixture consisted of ; 26 microliters of 50 mM TRIS/HCl, 10 mM $MgCl_2$ pH 7.6 buffer, 25 microliters of test drug or $10^{-6}$ pindolol to define nonspecific binding, 100 microliters of [I-125]-Pindolol (2200 Ci/mM) at a final concentration of $10^{-9}$, and 100 microliters of brain cortical membranes. The mixture was incubated at room temperature (22° C.) for two hours in the dark. The reaction was stopped by filtration of the mixture through buffer soaked glass fiber membranes (GF/B) using an cell harvesting device (Skatron Inc.). The radioactivity in each filter containing the trapped membrane particles was counted with a gamma counter. The value for non-specific binding in each assay was subtracted from total binding to give a value for specific binding. All specific binding values obtained in the presence of test compounds were expressed as the percentage of specific binding displaced by the individual agents. The resultant values were plotted on a log plot of concentration of test compound vs. percentage of displacement and an $IC_{50}$ value (drug concentration which produces 50% displacement) determined. Values obtained by this analysis are then reported as the negative log of the $IC_{50}$ ($pIC_{50}$) The compound of Example 19 showed a $pIC_{50}$ of 7.57.

Pharmaceutical Formulation and Doses

Compounds of formula (I) may be used in the treatment of CHF in a manner similar to the use of beta-adrenergic blocking agents and (+)-inotropic agents. After suffering a heart attack, one therapy which may be used is administration of a beta-blocker, such as atenolol to lessen oxygen consumption for the damaged heart muscle. However, there is often a negative inotropic action associated with beta-blockers whereby one may consider use of a positive inotropic agent. The usage of compounds of the invention may thus be correlated to the desire to manifest both beta-blocking and positive inotropic actions in a patient.

The compounds of formula (I) can be administered orally, topically or parentally, e.g. rectal or i.v., of which the preferred route is oral. The compounds may be admixed with conventional tableting aids, diluents, excepients as known in the art to form tablets, capsules, powders, elixirs, liquids or suspensions as known in the pharmaceutical art. For administration to humans, the compounds of the invention may be administered in an amount of about 0.1 to 5 mg/kg about 1-4 times per day. The particular dosage will depend on the activity of the specific compound chosen and the severity of the physiological condition being treated. The projected dosage can be determined by correlation of test results in pharmacological tests for known positive inotropic agents such as milrinone to those for compounds of formula (I).

In the following examples and throughout the specification, the following abbreviation may be used: g (grams),; mg (milligrams); l (liters); ml (milliliters); M (molar); mM (millimolar); i.v. (intravenous); Hz (Hertz); dP/dt (change in pressure per time period); mol (moles); DMF (N,N-dimethylformamide); DMSO (dimethylsulfoxide); TFA (trifluoroacetic acid): RT (room temperature); EtOAc (ethyl acetate); min (minutes); hrs (hours); m.p. (melting point); and TLC (thin layer chromatography).

Unless otherwise indicated, all temperatures are expressed in ° C. (degrees Centigrade), pressures in mmHg (millimeters of mercury), optical rotations measured at ambient temperature with the concentration (c) being in mg/10 ml and all references to ether are to diethyl ether.

EXAMPLE 1

6-{4-[N-[2-[3-phenoxy-2-hydroxypropylamino]ethyl carbamoylmethoxyphenyl]}-5-methyl-4,5-dihydro-3(2H)pyridazinone A mixture of 876 mg (3.34 mmol) of 6-(4-carboxymethoxyphenyl)-5-methyl-4-5-dihydro-3(2H)-pyridazinone, prepared according to the procedure of Y. Morisawa et al, Eur. Pat. Appl. 178,189, 589 mg (3.67 mmol) of 2-(tert-butoxycarbamoyl)ethyl amine, and 577 microliters (3.80 mmol) of diethylcyanophosphonate in 10 ml of DMF is stirred under an atmosphere of nitrogen while cooling in an ice-water bath. To this mixture is added, dropwise, 1.02 ml (7.34 mmol) of triethylamine in 4 ml of DMF. The mixture is stirred for 30 min in the ice-water bath and then overnight at RT. The DMF is removed under vacuum, and the residue is dissolved in 150 ml of EtOAc. The EtOAc solution is washed with 50 ml of 2% HCl, 100 ml of saturated sodium bicarbonate solution, and 75 ml of saturated sodium chloride solution. The EtOAc solution is dried (anhydrous MgS04), filtered, and the solvent removed under vacuum. The residue is flash chromatographed on silica gel (95:5 $CHCl_3$:$CH_3OH$) and then recrystallized from hexane-EtOAc to give 913 mg of 6-[4-[N-[2-tert-butoxycarbamoylethyl]carbamoylmethoxy]phenyl]-5-methyl-4,5-dihydro-3(2H)-pyridazinone as a white powder, m.p. 190°-192° C.; 68% yield.

| Elemental Analysis (for $C_{20}H_{28}N_4O_5$): | | | |
|---|---|---|---|
| | C (%) | H (%) | N (%) |
| Found: | 59.30 | 6.98 | 13.72. |
| Calculated: | 59.39 | 6.98 | 13.85 |

A solution of 830 mg (2.05 mmol) of 6-[4-[N-[2-tert-butoxycarbamoylethyl]carbamoylmethoxy]phenyl5-methyl-4,5-dihydro-3(2H) pyridazinone in 10 ml of methylene chloride is cooled in an ice-water bath while stirring under $N_2$. To the mixture is added, dropwise, 5 ml of TFA. The mixture is stirred 30 min in the ice bath, then allowed to warm to RT and stirred for 2 hrs. The solvent and excess reagent is removed under vacuum to leave a trifluoracetate salt as a pale yellow solid (1.09 g).

This solid is suspended in 150 ml of $CH_3CN$, 1.13 g (8.2 mmol) of powdered anhydrous $K_2CO_3$ added, and the mixture heated at reflux for 2 hrs. After cooling, the $CH_3CN$ is filtered. The solid collected from the filtration is placed in a soxhlet extractor and extracted continuously overnight with the $CH_3CN$ filtrate. The solvent is removed under vacuum to give 1.261 g of a white solid. This solid is dissolved in about 5 ml of $CH_3OH$, and flash chromatographed through silica gel (90:10:2 $CHCl_3:CH_3OH:NH_4OH$) to give 499 mg of 6-[4-[2-aminoethylcarbamoylmethoxy]phenyl]-5-methyl-4,5-dihydro-3(2H)-pyridazinone as a waxy white solid, 80% yield.

A solution of 499 mg (1.64 mmol) of 6-[4-[2-aminoethylcarbamoylmethoxy]phenyl]-5-methyl-4,5-dihydro-3(2H)-pyridazinone and 208 ml (1.54 mmol), of (2S)-(+)-3-phenoxy-1,2-epoxypropane, prepared by the procedure of K. B. Sharpless et. al, *J. Org. Chem.* 1989, 54, 1302, in 10 ml of $CH_3CN$ is heated at reflux for 10 hrs. The solvent is removed, the residue taken up in 1:1 $CHCl_3:CH_3OH$ (10 ml) and flash chromatographed on silica gel using 500 ml of 90:10 $CHCl_3:CH_3OH$ followed by 1000 ml of 90:10:2 $CHCl_3:CH_3OH:NH_4OH$ as the eluent to give 423 mg of 6-{4-[N-[2-[3-phenoxy-2-hydroxypropylamino]ethyl]carbamoylmethoxyphenyl]}-5-methyl-4,5-dihydro-3(2H)-pyridazinone as a white solid, yield, 60%. This product is dissolved in 15 ml of EtOAc and 5 ml of diethyl ether is added. While stirring vigorously, 12 ml of 0.10 M maleic acid in ether is added to the solution. The resulting white precipitate is collected by suction filtration, washed thoroughly with ethyl ether, and dried overnight at 50° C. under high vacuum to give the maleate salt as a white solid, m.p. 58°-73° C.

| Elemental Analysis (for $C_{24}H_{30}N_4O_5.C_4H_4O_4.H_2O$): | | | |
|---|---|---|---|
| | C (%) | H (%) | N (%) |
| Found: | 56.73 | 5.93 | 9.12 |
| Calculated: | 57.13 | 6.17 | 9.52 |

EXAMPLE 2

6-{4-[N-[2-[3-(2-cyanophenoxy)-2-hydroxypropylamino]ethyl carbamoylmethoxyphenyl]}-5-methyl-4,5-hydro-3(2H)pyridazinone A solution of 304 mg (1.00 mmol) of 6-[4-[2-aminoethylcarbamoylmethoxy]phenyl]-5-methyl 4,5-dihydro-3(2H)-pyridazinone, prepared as described in Example 1, and 131 mg (0.75 mmol) of (2S)-3-(2-cyanophenoxy)1,2-epoxypropane in 5 ml of $CH_3OH$ is heated at reflux under $N_2$ for 5 hrs. After cooling, the solvent is removed under vacuum and the residue flash chromatographed on silica gel using 250 ml of 90:10 $CHCl_3:CH_3OH$ followed by 250 ml of 90:10:2 $CHCl_3:CH_3OH:NH_4OH$ to give 233 mg of 6-{4-[N-[2-[3-cyanophenoxy)-2-hydroxypropylamino]ethyl]carbamoylmethoxyphenyl] -5-methyl-4,5-dihydro-3(2H)-pyridazinone as a white solid. Yield, 65%. This material is dissolved in 15 ml of EtOAc and converted to the maleate salt by treatment with a 0.10M ethereal solution of maleic acid. The maleate salt, 22 mg, is obtained as a white solid, m.p. 46°-62° C.

| Elemental Analysis (for $C_{25}H_{29}N_5O_5.C_4H_4O_4.\frac{1}{2}H_2O$): | | | |
|---|---|---|---|
| | C (%) | H (%) | N (%) |
| Found: | 57.54 | 5.63 | 11.38 |
| Calculated: | 57.61 | 5.67 | 11.58 |

EXAMPLE 3

6-{4-[N-[2-3-(2-methylphenoxy)-2-hydroxypropylamino1ethyl carbamoylmethoxyphenyl ]}-5-methyl-4,5-dihvdro-3(2H)pyridazinone A solution of 400 mg (1.3 mmol) of -[4-[2-aminoethylcarbamoylmethoxy]phenyl]-5-methyl-4,5-dihydro-3(2H)-pyridazinone, prepared as in Example 1, and 162 mg (1.0 mmol) of (2S)-3-(2-methylphenoxy)-1,2-epoxypropane in 5 ml of $CH_3OH$ is heated at reflux under $N_2$ for 5 hrs. After cooling, the solvent was removed under vacuum and the residue purified by flash chromatography on silica gel (95:5 $CHCl_3:CH_3OH$) to give 390 mg of 6-{4-[N-[2-[3-(2-methylphenoxy)-2-hydroxypropylamino]ethyl]carbamoylmethoxyphenyl]}-5-methyl-4,5-dihydro-3(2H)-pyridazinone as a tacky white solid. Yield, 83%. This material is dissolved in 25 ml of EtOAc and treated with 0.10M maleic acid in ethyl ether to precipitate the maleate salt. The salt is then recrystallized from $CH_3OH$-EtOAc to afford 340 mg of a white solid, m.p. 94°-102° C.

| Elemental Analysis (for $C_{25}H_{32}N_4O_5.C_4H_4O_4$): | | | |
|---|---|---|---|
| | C (%) | H (%) | N (%) |
| Found: | 59.56 | 6.36 | 9.38 |
| Calculated: | 59.57 | 6.21 | 9.58 |

EXAMPLE 4

6-{4-N-[2-chlorophenoxy1-2-hydroxypropylamino1ethyl carbamoylmethoxyphenyl]}-5-methyl-4,5-dihvdro-3(2H)-pyridazinone A solution of 400 mg (1.3 mmol) of 6-[4-[2-aminoethylcarbamoylmethoxy]phenyl]-5-methyl-4,5-dihydro-3(2H)-pyridazinone, prepared as in Example 1, and 187 mg (1.0 mmol) of (2S)-3-(2-chlorophenoxy)-1,2-epoxypropane in 5 ml of $CH_3OH$ is heated at reflux under $N_2$ for 5 hrs. The solvent was removed under vacuum and the residue flash chromatographed on silica gel (90:10 $CHCl_3:CH_3OH$) to give 400 mg of 6-{4-[N-[2-chlorophenoxy]-2-hydroxypropylamino]-ethyl]carbamoylmethoxyphenyl]}-5-methyl 4,5-dihydro-3(2H)pyridazinone as a tacky white solid. Yield, 82%. This material is dissolved in 25 ml of EtOAc and treated with ethereal 0.10 M maleic acid to precipitate the maleate salt. The maleate salt is recrystallized from acetone-hexane to give 380 mg of a white powder, m.p. 101°-109° C.

| Elemental Analysis (for C29H29ClN4O5.C4H4O4.½H2O: | | | |
|---|---|---|---|
| | C (%) | H (%) | N (%) |
| Found: | 55.18 | 5.63 | 9.04 |
| Calculated: | 54.77 | 5.58 | 9.13 |

EXAMPLE 5

6-{4-[N-2-[3-(2-morpholinophenoxy)-2-hydroxy-propylamino1ethylcarbamoylmethoxyphenyl]}-5-methyl 4,5-dihvdro-3(2H)pyridazinone A solution of 304 mg (1.00 mmol) of 6-[4-[2-aminoe-thylcarbamoylmethoxy]phenyl]-5-methyl-4,5-dihydro-3(2H)-pyridazinone, prepared as in Example 1, and 176 mg (0.75 mmol) of (2S)-3-(2-morpholinophenoxy)-1,2-epoxypropane in 5 ml of CH3OH is heated at reflux under N2 for 5 hrs. The solvent was removed under vacuum and the residue flash chromatographed on silica gel using 250 ml of 95:5 CHCl3:CH3OH, then 250 ml of 90:10:1 CHCl3:CH3OH:NH4OH and finally 250 ml of 90:10:2 CHCl3:CH3OH:NH4OH to give 227 mg of 6-{4-[N-[2-morpholinophenyl]-2-hydroxy-propylamino]ethyl]carbamoylmethoxyphenyl]}-5-methyl-4,5-dihydro-3(2H)pyridazinone as a white solid. Yield, 56%. This material is taken up in 20 ml of EtOAc and the maleate salt precipitated by the addition of 0.10 M maleic acid in ethyl ether. After drying overnight under high vacuum at 50° C., 243 mg of the maleate salt is obtained as a white powder, m.p. 62° (d).

| Elemental Analysis (for C28H37N5O6.1.5C4H4O4.H2O): | | | |
|---|---|---|---|
| | C (%) | H (%) | N (%) |
| Found: | 56.09 | 6.20 | 9.44 |
| Calculated: | 55.80 | 6.20 | 9.57 |

EXAMPLE 6

6-{4-[N-[2-3-4-(2-methoxy-1-ethyl)1phenoxy1-2-hydroxypropylamino ethyl]carbamoylmethoxyphenyl]}-5-methyl-4,5-dihydro-3(2H)-pyridazinone A solution of 304 mg (1.00 mmol) of 6-[4-[2-aminoe-thylcarbamoylmethoxy]phenyl]-5-methyl-4,5-dihydro-3(2H)-pyridazinone, prepared as in Example 1, and 156 mg (0.75 mmol) of (2S)-3-[4-(2-methoxyethyl)phenoxy]-1,2-epoxypropane in 5 ml of CH3OH is heated at reflux under N2 for 5 hrs. The solvent was removed under vacuum and the residue flash chromatographed on silica gel (90:10 CHCl :CH3OH) to give 145 mg of a white solid. Yield, 38%. This material is dissolved in 20 ml of EtOAc and treated with 0.10 M maleic acid in ethyl ether to precipitate the maleate salt. The maleate salt is dried overnight at 70° C. under high vacuum to give 177 mg of a white solid, m.p. 104°-108° C.

| Elemental Analysis (for C27H36N4O6.C4H4O4.H2O): | | | |
|---|---|---|---|
| | C (%) | H (%) | N (%) |
| Found: | 57.35 | 6.42 | 8.66 |
| Calculated | 57.57 | 6.55 | 8.66 |

EXAMPLE 7

6-{4-N-[2-[3-4-(2-cyclopropylmethoxy-1-ethyl)1-phenoxy]-2-hydroxypropylamino]ethyl]carbamoylme-thoxyphenyl]}-5-methyl 5-dihvdro-3(2H)-pyridazinone A solution of 304 mg (1.0 mmol) of 6-[4-[2-aminoe-thylcarbamoylmethoxy]phenyl]-5-methyl-4,5-dihydro-3(2H)-pyridazinone, prepared as in Example 1, and 186 mg (0.75 mmol) of (2S)-3-[4-(2-cyclopropylmethoxy-1-ethyl)]-phenoxy-1,2-epoxypropane in 5 ml of CH3OH is heated at reflux for 5 hrs under N2. The solvent is removed and the residue flash chromatographed on silica gel to give a white solid. Yield, 38%. This material is dissolved in 20 ml of EtOAc and treated with 0.10 M maleic acid in ether to precipitate the maleate salt. After drying at 70° C. overnight under high vacuum, 218 mg of the maleate salt was obtained as a white solid, m.p. 108°-113° C.

| Elemental Analysis (for C30H40N4O6.C4H4O4.H2O): | | | |
|---|---|---|---|
| | C (%) | H (%) | N (%) |
| Found: | 58.85 | 6.61 | 8.12 |
| Calculated: | 59.46 | 6.75 | 8.16 |

EXAMPLE 8

6-{4-[N-[2-[3-phenoxy-2-hydroxypropylamino1-2-methylpropyl]-carbamoylmethoxyphenyl]}-5-methyl-4.5-dihvdro-3(2H)Zpyridazinone A solution of 1.00 g (3.81 mmol) of 6-(4-carboxyme-thoxyphenyl)-5-methyl-4,5-dihydro-3(2H)-pyridazi-none, prepared according to the procedure of Y. Morisawa et.al. Eur. Pat Appl. 0178,189, 440 microliters (4.19 mmol) of 1,2-diamino-2-methylpropane, and 694 microliters (4.57 mmol) of diethylcyanophosphonate in 15 ml of DMF, is stirred under an atmosphere of N2 in an ice-water bath. A solution of 2.12 ml (15.2 mmol) of triethylamine in 5 ml of DMF is added dropwise to this mixture. The mixture is stirred for 30 min in the ice-water bath and then overnight at RT. The volatiles are removed under vacuum and the residue flash chromatographed on silica gel (250 ml of 90:10:0.5 CHCl3:CH3OH:NH4OH followed by 500 ml of 90:10:2 CHCl3:CH3OH:NH4OH) to give 1.352 g of a white solid. This solid resisted recrystallization from EtOAc-hexane, although 1H-NMR reveals it is a mixture of the desired amine and impurities derived from the diethyl-cyanophosphonate. The crude amine is dissolved in 25 ml of dry CH3OH and the oxalate salt precipitated by adding ethereal 0.10 M oxalic acid. The resulting precipitate was triturated twice with boiling CH3OH to give 991 mg of the oxalate salt of 6-[4-[N-[2-amino-2-methylpropyl]carbamoylmethoxy]phenyl]-5-methyl-4,5-dihydro-3(2H)-pyridazinone as a white powder. Yield, 62%. IH-NMR shows this material to be free of impurity.

The oxalate salt obtained above (816 mg, 1.93 mmol) is added to 175 ml of dry CH3CN containing 1.335 g (9.65 mmol) of powdered anhydrous K2CO3. The mixture is heated for 2 hrs at reflux, cooled, and filtered. The collected solids are placed in a soxhlet extractor and continuously extracted overnight with the CH3CN filtrate. The CH3CN is removed to leave 627 mg of 6-[4-[N-[2-amino-2-methylpropyl]carbamoylmethoxy]-phenyl]-5-methyl-4,5-dihydro-3(2H)-pyridazinone as a clear, glassy solid. Yield, 98%.

A solution of 627 mg (1.89 mmol) of the amine prepared above and 154 microliters (1.13 mmol) of (2S)-(+)-3-phenoxy1,2-epoxypropane in 5 ml of $CH_3OH$ is heated 24 hrs at reflux. The solvent is removed and the residue flash chromatographed on silica gel (250 ml of 95:5 CHCl $CH_3OH$ followed by 500 ml of 90:10:2 $CHCl_3:CH_3:NH_4OH$) to give 373 mg of 6-{4-[N-[2-[3-phenoxy-2-hydroxypropylamino]-2-methylpropyl]carbamoylmethoxyphenyl]}-5-methyl-4,5-dihydro-3(2H)pyridazinone as a clear, glassy solid. Yield 68%. This product is dissolved in 5 ml of $CH_3OH$, 5 ml of ether is added and the maleate salt precipitated by adding 0.1M maleic acid in ether. After drying overnight at 50° C. under high vacuum, 381 mg of the maleate salt is obtained as a white crystalline solid, m.p. 58°–78° C.

| Elemental Analysis (for $C_{26}H_{34}N_4O_5 \cdot C_4H_4O_4 \cdot 0.5H_2O$): | | | |
| --- | --- | --- | --- |
| | C (%) | H (%) | N (%) |
| Found: | 58.91 | 6.39 | 8.90 |
| Calculated: | 59.29 | 6.47 | 9.22 |

EXAMPLE 9

6-{4-N-[2-3-(2-cyanophenoxy)-2-hydroxypropylamino1-2methylpropyl]carbamoylmethoxyphenyl]}-5-methyl-4,5-dihvdro(2H)-pyridazinone A solution of 342 mg (1.03 mmol) of 6-{4-[N-[2-amino-2-methylpropyl]carbamoylmethoxy]phenyl]}-5-methyl-4,5-dihydro-3(2H)-pyridazinone, prepared as in Example 8, and 162 mg(0.927 mmol) of (2S)-3-(2-cyanophenoxy)-1,2-epoxypropane in 5 ml of $CH_3OH$ is heated under $N_2$ at reflux for 24 hrs. The solvent is removed under vacuum and the residue flash chromatographed on silica gel (250 ml of 95:5 $CHCl_3:CH_3OH$ followed by 500 ml of 90:10 $CHCl_3:CH_3OH$) to give 187 mg of 6-{[4-[N-[2-[3-(2-cyanophenoxy)-2-hydroxypropylamino]-2-methylpropyl]carbamoylmethoxyphenyl]}-5-methyl-4,5-dihydro-3(2H)-pyridazinone as a crystalline solid, m.p. 58°–73° C.

| Elemental Analysis (for $C_{27}H_{33}N_5O_5 \cdot 1.5H_2O$): | | | |
| --- | --- | --- | --- |
| | C (%) | H (%) | N (%) |
| Found: | 61.08 | 6.37 | 13.14 |
| Calculated: | 60.65 | 6.79 | 13.10 |

EXAMPLE 10

6-{4-[N-[2-3-(2-chlorophenoxy)-2-hydroxypropylamino1-2methylpropyl]carbamoylmethoxyphenyl]}-5-methyl-4,5-dihvdro-(2H)-pyridazinone A solution of 342 mg (1.03 mmol) of 6-{4-[N-[2-amino-2-methypropyl]carbamoylmethoxy]phenyl)-5-methyl-4,5-dihydro-3(2H)-pyridazinone, prepared as in Example 8, and 171 mg (0.927 mmol) of (2S)-3-(2-chlorophenoxy)-1,2-epoxypropane in 5 ml of $CH_3OH$ is heated under $N_2$ at reflux for 24 hrs. The solvent is removed under vacuum and the residue flash chromatographed on silica gel (500 ml of 95:5 $CHCl_3:CH_3OH$ followed by 500 ml of 90:10 $CHCl_3:CH_3OH$) to give 163 mg of 6-{4-[N-[2-[3-(2-chlorophenoxy)-2-hydroxypropylamino]-2methylpropyl]carbamoylmethoxyphenyl]}-5-methyl-4,5-dihydro-3(2H)-pyridazinone as a crystalline solid. Yield, 29%.

| Elemental Analysis (for $C_{26}H_{33}ClN_4O_5 \cdot 1.5H_2O$): | | | |
| --- | --- | --- | --- |
| | C (%) | H (%) | N (%) |
| Found: | 57.66 | 6.25 | 10.32 |
| Calculated: | 57.40 | 6.67 | 10.30 |

EXAMPLE 11

6-{4-N-[2-[(3-phenoxy-2-hydroxypropylamino}ethyl carbamoylpropyloxyphenyl]}-5-methyl-4,5-dihvdro-3(2H)-pyridazinone A mixture of 1.00g (4.90 mmol) of 6-4-(hydroxyphenyl)-5-methyl-4,5-dihydropyridazinone, 745 mg (5.39 mmol) of anhydrous $K_2CO_3$ and 1.15g (5.88 mmol) of ethyl 4-bromobutyrate in 20 ml of DMF is heated at 100° for 2 hrs under $N_2$. The DMF is then removed under vacuum, and the residue partitioned between water and EtOAc. The EtOAc is washed with water, dried ($MgSO_4$), filtered and the solvent removed to leave 1.471 g of 6-[4-(4-carbethoxypropyloxy)]phenyl-5-methyl-4,5-dihydro-3(2H)-pyridazinone as a white solid. Yield, 97%.

A solution of 1.623 g (5.10 mmol) of the ethyl ester prepared above, 816 mg (20.4) of sodium hydroxide, 12.5 ml of water, and 12.5 ml of ethanol is heated 2 hrs at 80° C. under $N_2$. After cooling, an equal volume of water is added, and the solution extracted with ether (2×100 ml). The aqueous phase is cooled in an ice-water bath, acidified with 1N HCl, and the resulting white precipitate of 6-[4-(4-carboxypropyloxy)]phenyl-5-methyl-4,5-dihydro-3(2H)-pyridazinone collected by suction filtration. Yield, 1.406 g (95%).

A mixture of 1.202 g (4.14 mmol) of the carboxylic acid prepared above, 729 mg (4.55 mmol) of 2-(tert-butoxycarbamoyl)ethyl amine, and 749 mg (4.59 mmol) of diethylcyanophosphonate in 10 ml of DMF is stirred under $N_2$ in an ice-water bath. A solution of 1.270 ml (9.11 mmol) of triethylamine in 5 ml of DMF is added dropwise, the solution is stirred for 30 min in the ice-water bath and then overnight at RT. The DMF is removed under vacuum and the residue flash chromatographed on silica gel (97:3 $CHCl_3:CH_3OH$) and the resulting foamy white solid is recrystallized from EtOAc-hexane to give 1.499 g of 6-[4-[N-[2-tert-butoxycarbamoylethyl]carbamoylpropyloxy]phenyl-5-methyl-4,5-dihydro-3(2H)-pyridazinone as a white solid. m.p. 124-125° C. Yield, 84%.

| Elemental Analysis (for $C_{22}H_{32}N_4O_5$): | | | |
| --- | --- | --- | --- |
| | C (%) | H (%) | N (%) |
| Found: | 61.25 | 7.43 | 12.89 |
| Calculated: | 61.09 | 7.46 | 12.96 |

A solution of 1.593 g (3.68 mmol) of the carbamate prepared above in 10 ml of $CH_2Cl_2$ is stirred under $N_2$ in an ice-water bath and treated dropwise with 10 ml of TFA. After 30 min in the ice-water bath, the mixture is allowed to come to RT and stirred two hrs. Volatile materials are removed under high vacuum to leave a viscous, pale yellow oil, 2.737 g. This oil is taken up in 100 ml of $CH_3CN$, 2.54 g (18.4 mmol) of powdered anhydrous potassium carbonate added, and the mixture heated at reflux for 2 hrs. After allowing to cool, the solution is filtered, and the recovered salts placed in a soxhlet extractor and continuously extracted overnight with the acetonitrile filtrate. The $CH_3CN$ is removed under high vacuum to leave 3.07 g of a tacky white solid. The $^1H$-NMR of this solid confirms it to be the desired 6-[4-[2-aminoethylcarbamoylpropyloxy]-phenyl]-5-methyl-4,5-dihydro-3(2H)-pyridazinone. However, the extra mass indicates the amine is contaminated with potassium trifluoroacetate. Assuming complete conversion of the tert-butyl carbamate to the amine and complete extraction of the amine, this 3.07 g is about 40% (by weight) the free amine. This solid was used in the next step without purification.

A solution of 1.500 g (1.79 mmol assuming 40% free amine) of the mixture of amine and $KOCOCF_3$ obtained above and 242 microliters (1.79 mol) of (2S)-(+)-3-phenoxy-1,2epoxypropane in 4 ml of $CH_3CN$ and 4 ml of $CH_3OH$ is heated at reflux under $N_2$ for 24 hrs. The solvent is removed and the residue flash chromatographed on silica gel (250 ml of 90:10 $CHCl_3:CH_3OH$ followed by 250 ml of 90:10:1 $CHCl_3:CH_3OH:NH_4OH$ followed by 250 ml of 90:10:2 $CHCl_3:CH_3OH:NH_4OH$) to give 360 mg of 6-{4-[N-[2-[3-phenoxy-2-hydroxy-propylamino]ethyl]carbamoylpropyloxyphenyl]}-5-methyl-4,5-dihydro-3(2H)pyridazinone as an amorphous white solid. Yield, 42%. This solid is dissolved in 15 ml of EtOAc, 10 ml of ethyl ether is added, and the maleate salt is precipitated by adding 0.100M maleic acid in ethyl ether. The salt is collected by suction filtration and dried overnight under high vacuum at 45° C. to give 281 mg of the maleate salt as a white powder, m.p. 48°–58° C.

| Elemental analysis (for $C_{26}H_{34}N_4O_5.C_4H_4O_4.0.5\ H_2O$): | | | |
|---|---|---|---|
| | C (%) | H (%) | N (%) |
| Found: | 59.41 | 6.55 | 9.23 |
| Calculated: | 59.29 | 6.47 | 9.22 |

EXAMPLE 12

6-{4-[3-[N-(3-phenoxy-2-hydroxypropyl)1amino1-propyloxyphenyl]}-5-methyl-4,5-dihvdro-3(2H)-pyridazinone A mixture of 500 mg (2.45 mmol) of 6-(4-hydroxyphenyl)-methyl-4,5-dihydro-3(2H)-pyridazinone (prepared by the method described in Eur. Pat. Appl. EP 178,189 A2), 373 mg (2.70 mmol) of powdered anhydrous $K_2CO_3$, and 790 mg (2.95 mmol) of N-(3-bromopropyl)phthalimide in 10 ml of DMF is heated at 100° C. for 2 hrs. The DMF is removed under vacuum, the residue is taken up in 125 ml of EtOAc and 100 ml of water, the organic phase washed once with 75 ml of water, died ($MgSO_4$), and the solvent removed to give 0.997 g of 6-[4-(3-phthalimidopropyloxy)phenyl]-5-methyl-4,5-dihydro-3(2H)-pyridazinone as a white solid. Yield, 99%.

A mixture of 0.997 g (2.55 mmol) of the phthalimide prepared above, 124 microliters (2.55 mmol) of 98% hydrazine monohydrate, and 25 ml of ethanol is heated at reflux under $N_2$ overnight. TLC (90:10 $CHCl_3:CH_3OH$) of the reaction mixture showed some phthalimide still present. An additional 25 ml of hydrazine was added, and the mixture heated at reflux for 3 hrs. The solvent is removed under vacuum, the residue taken up in about 10 ml of $CH_3OH$ and flash chromatographed on silica gel (90:10:2 $CHCl_3:CH_3OH:NH_4OH$) to give 531 mg of 6-[4-(3-aminopropyloxy)phenyl]-5-methyl-4,5-dihydro-3(2H)pyridazinone as a white solid. Yield 80%.

A solution of 250 mg (0.784 mmol) of the amine prepared above and 106 microliters (0.784 mmol) of (2S)-(+)-3-phenoxy-1,2-epoxypropane in 2 ml of 1:1 $CH_3CN:CH_3OH$ is heated at reflux under $N_2$ for five hrs. The solvent is removed under vacuum and the residue is flash chromatographed on silica gel (250 ml of 90:10 $CHCl_3:CH_3OH$, then 250 ml of 90:10:0.5 $CHCl_3:CH_3:NH_4OH$, then 250 ml of 90:10:1 $CHCl_3:CH_3OH:NH_4OH$, and finally 250 ml of 90:10:2 $CHCl_3:CH_3OH:NH_4OH$) to give 189 mg of 6-{4-[3-[N-(3-phenoxy-2-hydroxypropyl)]amino]-propyloxyphenyl }-5-methyl-4,5-dihydro-3(2H)-pyridazinone as an amorphous white solid. This is recrystallized from EtOAc-hexane to give 114 mg of a white powder, m.p. 109°–118° C.

| Elemental analysis (for $C_{23}H_{29}N_3O_4$): | | | |
|---|---|---|---|
| | C (%) | H (%) | N (%) |
| Found: | 67.11 | 7.10 | 10.18 |
| Calculated: | 67.13 | 7.10 | 10.21. |

EXAMPLE 13

6-{4-[-N-[2-[3-phenoxy-2-hydroxypropylamino1ethyl carbamoylmethoxyphenyl]}-4,5-dihvdro-3(2H)-pyridazinone A mixture of 25.0g (0.120 mmol) of 3-(4-methoxybenzoyl)-propionic acid and 175 ml of 48% HBr is heated under $N_2$ at 110° C. for 5 hrs. After cooling, the mixture is diluted with an equal volume of water and exhaustively extracted with EtOAc (5×100 ml). The organic phase is washed with saturated NaCl, dried ($MgSO_4$), filtered and the solvent removed to leave a white solid. After recrystallization from EtOAc, 16.8 g of 3-(4-hydroxybenzoyl)propionic acid, m.p. 157°–159° C., is obtained. Yield, 72%.

A mixture of 10.0 g (51.5 mmol) of the acid prepared above and 6.2 ml (128 mmol) of 98% hydrazine monohydrate in 172 ml of ethanol is heated at reflux overnight under $N_2$. The resulting white solid is collected by suction filtration to give 9.37 g of 6-(4-hydroxyphenyl)-4,5-dihydro-3(2H)pyridazinone as a white powder, m.p.>300° C.

| Elemental analysis for $C_{10}H_{10}N_2O_2$: | | | |
|---|---|---|---|
| | C (%) | H (%) | N (%) |
| Found: | 63.43 | 5.32 | 14.67 |
| Calculated: | 63.15 | 5.30 | 14.73 |

A mixture of 2.00 g (10.5 mmol) of the phenol prepared above, 1.60g (11.6 mmol) of anhydrous $K_2CO_3$, 1.304 ml (11.8 mmol) of ethyl bromoacetate, and 40 ml of DMF is heated at 100° C. for 2 hrs under $N_2$. The DMF is removed under vacuum and the residue taken up in 150 ml of EtOAc and 75 ml of water. The organic phase is washed with 50 ml of 5% aqueous NaOH, twice with saturated NaCl, dried ($MgSO_4$), filtered, and the solvent removed to leave 2.186 g of a slightly yellow solid. This is recrystallized from hexane-EtOAc to give 2.01 g of 6-(4-carboethoxymethoxyphenyl)-4,5-dihydro3(2H)-pyridazinone as a white, crystalline solid, m.p. 7°–129° C. Yield 69%.

A solution of 4.3 g (15.6 mmol) of the ethyl ester prepared above in 60 ml of 95% ethanol containing 3.49 g (62.3 mmol) of potassium hydroxide is stirred overnight at RT under $N_2$. The reaction is diluted with 150 ml of water and extracted with 75 ml of ether. The aqueous phase is cooled in ice, acidified with 20% HCl, the precipitate collected by suction filtration, washed twice with water then once with ethyl ether, and dried under high vacuum at 100° C. to give 3.7 g of 6-(4-carboxymethoxyphenyl)-4,5-dihydro-3(2H)-pyridazinone as a white powder. Yield, 96%.

A solution of 1.00 g (4.03 mmol) of the acid prepared above, 710 mg (4.43 mmol) of 2-tert-butoxycarbamoyl-)ethyl amine, and 697 microliters (4.59 mmol) of diethylcyanophosphonate in 15 ml of DMF is cooled in an ice-water bath and 1.20 ml of triethylamine in 2 ml of DMF is added dropwise. After 30 min the ice bath is removed and the solution stirred overnight at room temperature. The DMF is removed under vacuum and the residue flash chromatographed on silica gel (95:5 $CHCl_3:CH_3OH$). The white solid resulting from the chromatography is recrystallized from EtOAc to give 610 mg of 6-[4-[N-[2-tert-butoxycarbamoylethyl]carbamoylmethoxy]-phenyl]-4,5-dihydro-3(2H)pyridazinone as a white crystalline solid, m.p. 158°-160° C. Yield 39%.

A solution of 6lo mg (1.56 mmol) of the carbamate prepared above in 10 ml of $CH_2Cl_2$ is cooled in ice and 5 ml of TFA added. After 30 min the ice bath is removed and stirring at RT continued for 3 hrs. The volatiles are removed under high vacuum. The residual pale yellow solid is suspended in $CH_3CN$, treated with 862 mg (6.24 mmol) of powdered anhydrous $K_2CO_3$, and the mixture heated 2 hrs at reflux. After cooling, the $CH_3CN$ is filtered and the solids placed in a soxhlet extractor and continuously extracted overnight with $CH_3CN$. The $CH_3CN$ is removed under vacuum to leave 1.133 g of a white solid. $^1$H-NMR indicates this is the desired 6-[4-[2-aminoethylcarbamoyl-methoxy]-phenyl]-4,5-dihydro-3(2H)-pyridazinone but the extra mass indicates it also contains potassium trifluoroacetate. This solid is used without purification in the final step.

A solution of the amine prepared above (1.076 g, 1.56 mmol based on complete conversion of the tert-butylcarbamate) and 127 microliters (0.936 mmol) of (2S)-(+)-3-phenoxy1,2-epoxypropane in 5 ml of $CH_3CN$ and 1 ml of $CH_3OH$ is heated at reflux under $N_2$ for 7 hrs. The solvent is removed under vacuum and the residue flash chromatographed on silica gel (250 ml of 90:10 $CHCl_3$ $CH_3OH$ followed by 500 ml of 90:10:2 $CHCl_3:CH_3OH:NH_4OH$) to give 308 mg of a pale yellow solid. After recrystallization from hexane-EtOAc, 240 mg of 6(4-[N-[2-[3-phenoxy-2-hydroxypropylamino]ethyl]carbamoylmethoxyphenyl]}-4,5-dihydro-3(2H)-pyridazinone is obtained as a white powder, m.p. 113°-115° C.

| Elemental Analysis (for $C_{23}H_{28}N_4O_5.H_2O$): | | | |
|---|---|---|---|
| | C (%) | H (%) | N (%) |
| Found: | 59.83 | 6.09 | 11.82 |
| Calculated: | 60.25 | 6.59 | 12.20 |

EXAMPLE 14

6-{4-N-[2-2-cyanophenoxy-2-hydroxypropylamino]-2-methylpropyl carbamoylmethoxyphenyl]}-4,5-dihydro-3(2H)pyridazinone A solution of 3.0 g (12.1 mmol) of 6-(4-carboxymethoxy)-phenyl-4,5-dihydro-3(2H)-pyridazinone, prepared as described in Example 13, 1.17 g (13.3 mmol) of 1,2-diamino-2-methylpropane, and 2.02 ml (13.3 mmol) of diethyl cyanophosphonate in 25 ml of DMF is cooled in an ice-water bath. A solution of 1.85 ml (13.3 mmol) of triethylamine in 5 ml of DMF is added dropwise. The reaction is allowed to come to RT and stirred overnight. The volatiles are removed under vacuum and the residue flash chromatographed on silica gel (90:10:1 $CHCl_3:CH_3OH:NH_4OH$) to give a white solid. This solid is recrystallized from $CH_3OH$-EtOAc to give 2.4 g of 6-[4-[N-(2-amino-2-methylpropyl)carbamoylmethoxy]phenyl]-4,5-dihydro-3(2H)-pyridazinone as a white powder, m.p. 135°-137⊖ C. Yield, 62%.

A solution of 500 mg (1.6 mmol) of the amine prepared above and 248 mg (1.4 mmol) of (2S)-3-(2-cyanophenoxy)-1,2-epoxypropane in 10 ml of $CH_3OH$ is heated at reflux under $N_2$ for 12 hrs. The solvent is removed and the residue flash chromatographed on silica gel (90:10:2 $CHCl_3:CH_3OH:NH_4OH$) to give 6-(4-[2-[2-cyanophenoxy-2-hydroxypropylamino]-2methylpropyl]carbamoylmethoxyphenyl]}-4,5-dihydro-3(2H)pyridazinone as an amorphous white solid. This solid is taken up in 5 ml of $CH_3OH$, 5 ml of ether added, and the maleate salt is precipitated by adding 0.1 M maleic acid in ether. The maleate salt is washed thoroughly with ether and dried under high vacuum at 50° C. to give 501 mg of the maleate salt as a white solid, m.p. 72°-81° C. Yield, 66%

| Elemental Analysis (for $C_{26}H_{31}N_5O_5.C_4H_4O_4.0.5H_2O$): | | | |
|---|---|---|---|
| | C (%) | H (%) | N (%) |
| Found: | 58.04 | 5.81 | 11.22 |
| Calculated: | 58.24 | 5.89 | 11.32 |

EXAMPLE 15

6-{4-[N-[2-[2-methylphenoxy-2-hydroxypropylamino1-2-methylpropyl]carbamoylmethoxyphenyl]}-4,5-dihydro-3(2H)pyridazinone A solution of 500 mg (1.6 mmol) of 6-[4-[N-(2-amino-2-methylpropyl)carbamoylmethoxy]phenyl]4,5-dihydro-3(2H)-pyridazinone, prepared as described in Example 14, and 232 mg (1.40 mmol) of (2S)-3-(2-methylphenoxy)-1,2-epoxypropane in 10 ml of $CH_3OH$ is heated at reflux under $N_2$ overnight. The solvent is removed and the residue flash chromatographed on silica gel (90:10:2 $CHCl_3:CH_3OH:NH_4OH$) to give the product as a white solid. This is treated with 0.1 M maleic acid in ether to precipitate the maleate salt as 499 mg of a white powder, m.p. 70°-78° C. Yield, 65%.

| Elemental Analysis (for $C_{26}H_{34}N_4O_5.C_4H_4O_4.1.5 H_2O$): | | | |
|---|---|---|---|
| | C (%) | H (%) | N (%) |
| Found: | 57.20 | 6.14 | 8.50 |
| Calculated: | 57.58 | 6.53 | 8.95 |

EXAMPLE 16

6-{4-2-[2-chlorophenoxy-2-hydroxypropylamino-2-methylpropyl]carbamoylmethoxyphenyl]}-4,5-dihydro-3(2H)-pyridazinone A solution of 500 mg (1.6 mmol) of 6-[4-[N-(2-amino-2-methylpropyl)carbamoylmethoxy]phenyl]-4, 5dihydro-3(2H)-pyridazinone, prepared as described in Example 14, and 261 mg (1.4 mmol) of (2S)-3-(2-chlorophenoxy)-1,2-epoxypropane in 10 ml of $CH_3OH$ is heated at reflux under $N_2$ overnight. The solvent is removed and the residue flash chromatographed on silica gel (90:10:2 $CHCl_3:CH_3OH:NH_4OH$) to give the product as a white solid. This solid is taken up in 10 ml of 1:1 $CH_3OH—(C_2H_5)_2O$ and treated with 0.1 M maleic acid in ether to precipitate the maleate salt as 488 mg of white powder, m.p. 61°-67° C. Yield, 64%.

| Elemental Analysis (for $C_{25}H_{31}ClN_4O_5\cdot 2C_4H_4O_4\cdot H_2O$): | | | |
|---|---|---|---|
| | C (%) | H (%) | N (%) |
| Found: | 52.79 | 5.26 | 7.08 |
| Calculated: | 52.62 | 5.21 | 7.43 |

EXAMPLE 17

6-{4-N-[2-[(3-phenoxy)-2-hydroxypropylamino]ethyl carbamoylpropyloxyphenyl]}-4,5-dihydro-3(2H)-pyridazinone A mixture of 2.00 g (10.5 mmol) of 6-(4-hydroxyphenyl)-4,5-dihydro-3(2H)-pyridazinone, prepared as described in Example 13, 1.60 g (11.6 mmol) of anhydrous $K_2CO_3$ and 2.30 g (11.8 mmol) of ethyl 4-bromobutyrate in 40 ml of DMF is heated at 100° C. for 2 hrs under $N_2$. The DMF is removed under vacuum and the residue taken up in 150 ml of EtOAc and 75 ml of water. The organic phase is washed with 5% aqueous NaOH, then with saturated NaCl, dried ($MgSO_4$), and the solvent removed to leave 2.58 g of 6-[4-[3-carboethoxy-propyloxy]phenyl]-4,5-dihydro-3(2H)-pyridazinone as a white solid. Yield, 81%.

The ethyl ester prepared above (2.58 g, 8.48 mmol) is added to 40 ml of 1 1 ethanol-water containing 1 357 g (33.9 mmol) of NaOH. The mixture is heated at reflux for 3 hrs cooled to RT, acidified with 6N HCl, and the resulting bright yellow precipitate collected by suction filtration, washed thoroughly with water and dried overnight at 75° C. under high vacuum to give 2.262 g of 6-[4-[3-carboxypropyloxy]phenyl]-4,5-dihydro-3(2H)-pyridazinone as a yellow solid. $^1H$-NMR of this solid indicates about 30% contamination by products resulting from opening of the pyridazinone ring, but it was used without further purification in the next step.

A solution of 2.262 g (8.19 mmol) of the carboxylic acid prepared above, 1.444 g (9.01 mmol) of 2-tert-butoxycarbamoylethyl amine, and 1.603 g (9.83 mmol) of diethylcyanophosphonate in 25 ml of DMF is cooled in an ice-water bath and 2.486 g (24.6 mmol) of triethylamine in 5 ml of DMF added dropwise. After 30 min the ice bath is removed and the mixture allowed to stir overnight at RT. The DMF is removed under vacuum and the residue is taken up in 150 ml of EtOAc and 75 ml of water. The organic phase is washed with cold 2% aqueous HCl (2×50 ml), saturated $NaHCO_3$ solution (2×50 ml) and saturated $NaCl_3$ solution. After drying (MgSO ) and removal of the solvent, 1.457 g of yellow solid is obtained. This solid is flash chromatographed on silica gel (250 ml of 97:3 $CHCl_3:CH_3OH$ followed by 750 ml 55:5 $CHCl_3:CH_3OH$) to give 1.211 g of a yellow solid. This is recrystallized from EtOAc-$CH_3OH$ to give 932 mg of 6-[4-[N-[2-tert-butoxycarbamoylethyl]-carbamoylpropyloxy]-phenyl-4,5-dihydro-3(2H)-pyridazinone as a pale yellow solid, m.p. 162°-165° C.

| Elemental Analysis (for $C_{21}H_{30}N_4O_5$): | | | |
|---|---|---|---|
| | C (%) | H (%) | N (%) |
| Found: | 60.05 | 7.32 | 13.13 |
| Calculated: | 60.27 | 7.23 | 13.39 |

A solution of 932 mg (2.23 mmol) of the carbamate prepared above in 10 ml of $CH_2CL_2$ is cooled in an ice-water bath and 5 ml of TFA added dropwise. After 30 min, the ice bath is removed and stirring at RT continued for 3 hrs. Volatile materials are removed under vacuum and the residue taken up in 100 ml of $CH_3CN$, 2.466 g (17.8 mmol) of powdered anhydrous $K_2CO_3$ added, and the mixture heated 3 hrs at reflux. The solids are removed to leave 1.526 g of white solid. This solid is flash chromatographed on silica gel (85:15:3 $CHCl_3:CH_3OH:NH_4OH$) to give 242 mg of 6-[4-[2-aminoethylcarbamoylpropyloxy]phenyl]-4,5-dihydro(2H)-pyridazinone as a white solid. Yield, 34%.

A solution of 237 mg (0.744 mmol) of the amine prepared above and 81.0 microliters (0.596 mmol) of (2S)-(+)-3-phenoxy-1,2-epoxypropane in 5 ml of $CH_3OH$ is heated at reflux for 6 hrs under $N_2$. The solvent is removed under vacuum and the residue flash chromatographed on silica gel (250 ml of 90:10 $CHCl_3:CH_3OH$ followed by 500 ml of 90:10:2 $CHCl_3:CH_3OH:NH_4OH$) to give 177 mg of a white solid. This is recrystallized from EtOAc-CH OH to give 137 mg of 6-{4-[N-[2-[3-phenoxy-2-hydroxypropylamino]ethyl]carbamoylpropyloxyphenyl]}-4,5-dihydro-3(2H)-pyridazinone as a white powder, m.p. 121°-123° C.

| Elemental Analysis (for $C_{25}H_{32}N_4O_5$): | | | |
|---|---|---|---|
| | C (%) | H (%) | N (%) |
| Found: | 63.86 | 6.84 | 11.89 |
| Calculated: | 64.08 | 6.88 | 11.96 |

EXAMPLE 18

6-{4-[3-[N-3-phenoxy-2-hydroxypropylamino]-propyloxyphenyl]}4,5-dihydro-3(2H)-pyridazinone A mixture of 2.00 g (10.5 mmol) of 6-(4-hydroxyphenyl)-4,5-dihydro-3(2H)-pyridazinone, prepared as described in Example 13, 1.60 g (11.6 mmol) of anhydrous $K_2CO_3$, and 3.39 (1.26 mmol) of N-(bromopropyl)phthalimide in 43 ml of DMF is heated at 100° C. for 3 hrs under $N_2$. The DMF is removed under vacuum and the residue taken up in 125 ml of EtOAc and 50 ml of water. The organic phase is washed with 50 ml of 5% aqueous NaOH, then with saturated NaCl, dried ($MgSO_4$), and the solvent removed to leave a yellow solid. This solid is recrystallized from EtOAc to give 2.748 g of 6-[4-(3-phthalimidopropyloxy)phenyl]-4,5-dihydro3(2H)-pyridazinone as a white solid. Yield, 69%.

A solution of 2.748 g (7.28 mmol) of the phthalimide prepared above and 398 microliters (8.0 mmol) of 98% hydrazine hydrate in 75 ml o  hanol is heated overnight at reflux under $N_2$. After cooling to RT, the volatiles are removed under vacuum. The residual white solid is taken up in 15 ml of 70:30 $CH_3OH:NH_4OH$ and flash chromatographed on silica gel (90:10:2 $CHCl_3:CH_3OH:NH_4OH$) to give 929 mg of 6-[4-(3-aminopropyloxy)phenyl]-4,5-dihydro-3(2H)-pyridazinone as a white solid. Yield, 23%.

A solution of 500 mg (2.02 mmol) of the amine prepared above and 191 microliters (1.41 mmol) of (2S)-(+)-3-phenoxy-1,2-epoxypropane in 10 ml of 4:1 $CH_3OH:DMSO$ is heated at reflux for 6 hrs under $N_2$. The solvent is removed under vacuum and the residue flash chromatographed on silica gel (250 ml of 90:10 $CHCl_3:CH_3OH$ followed by 500 ml of 90:10:2 $CHCl_3:CH_3OH:NH_4OH$) to give 413 mg of a white solid. The solid is recrystallized from EtOAc-hexane to give 360 mg of the title product as a white powder, m.p. 110°–111° C.

| Elemental Analysis (for $C_{22}H_{27}N_3O_4$): | | | |
|---|---|---|---|
| | C (%) | H (%) | N (%) |
| Found: | 65.93 | 6.89 | 10.40 |
| Calculated: | 66.48 | 6.85 | 10.57 |

EXAMPLE 19

6-{4-N-[2-[3-phenoxy-2-hydroxypropylamino]ethyl]carbamoylmethoxy]-3-chlorophenyl}-4,5-dihydro-3(2H)-pyridazinone A solution of 1.310 g.(4 63 mmol) of 6-{4-[3-carboxymethoxy]-3-chlorophenyl}-4,5-dihydro-3(2H)-pyridazinone, prepared by the method of Eur. Pat. Application EP 0178189, 804 mg (5.02 mmol) of 2-tert-butoxycarbamoylethyl amine, and 870 microliters (5.73 mmol) of diethylcyanophosphonate in 13 ml of DMF is cooled in an ice-water bath and 1.874 g (18.5 mmol) of triethylamine is added dropwise. After 30 min the ice bath is removed and the mixture is stirred overnight at RT. The DMF is removed under vacuum and the residue taken up in 150 ml of EtOAc, washed with cold 2% aqueous HCl (2×50 ml), saturated $NaHCO_3$ (2×50 ml), saturated NaCl (1×50 ml), dried and the solvent removed to leave 1.514 g of a yellow solid. This material is flash chromatographed on silica gel (250 ml of 97:3 $CHCl_3:CH_3OH$ followed by 500 ml of 95:5 $CHCl_3:CH_3OH$) and the resulting solid recrystallized from EtOAc to give 793 mg of 6-[4-[N-[2-tert-butoxycarbamoylethyl]carbamoylmethoxy]-3-chlorophenyl]-4,5-dihydro-3(2H)-pyridazinone as a white powder, m.p. 184°–186° C.

| Elemental Analysis (for $C_{19}H_{25}ClN_4O_5$): | | | |
|---|---|---|---|
| | C (%) | H (%) | N (%) |
| Found: | 53.54 | 5.92 | 13.03 |
| Calculated: | 53.71 | 5.93 | 13.19 |

A solution of 682 mg (1.61 mmol) of the carbamate obtained above in 5 ml of $CH_2Cl_2$ is cooled in an ice bath and 5 ml of TFA is added dropwise. After 30 min the ice bath is removed and stirring continued at RT for 2 hrs. Volatiles are removed under vacuum, and the residue taken up in 150 ml of $CH_3CN$, 1.113 g (8.05 mmol) of anhydrous $K_2CO_3$ added, and the mixture heated at reflux for 2 hrs. After cooling, the solution is filtered and the recovered solids are continuously extracted in a soxhlet apparatus overnight with the $CH_3CN$ filtrate. The $CH_3CN$ is removed under vacuum to least 860 mg of a white solid. $^1H$-NMR shows this solid contains 6-[4-[2-aminoethylcarbamoylmethoxy]-3-chlorophenyl]-4,5-dihydro-3(2H)-pyridazinone presumably contaminated with potassium trifluoroacetate. Assuming complete conversion of the carbamate, this solid is 611% by weight the desired amine. This solid is used without purification in the final step.

A solution of 857 mg (1.16 mmol) of the amine prepared above and 153 ml (1.13 mmol) of (2S)-(+)-3-phenoxy-1,2-epoxypropane in 5 ml of $CH_3OH$ is heated at reflux under $N_2$ for 6 hrs. The solvent is removed under vacuum and the residue flash chromatographed on silica gel to give 269 mg of an amorphous white solid. This solid is recrystallized from EtOAc-hexane to give 215 mg of 6-{4-[N-[2-[3-phenoxy-2-hydroxypropylamino]ethyl]carbamoylmethoxy]-3-chlorophenyl}-4,5-dihydro-3(2H)-pyridazinone as a white powder, m.p. 112°–115°.

| Elemental Analysis (for $C_{23}H_{27}ClN_4O_5$): | | | |
|---|---|---|---|
| | C (%) | H (%) | N (%) |
| Found: | 58.18 | 5.67 | 11.59 |
| Calculated: | 58.16 | 5.73 | 11.80 |

EXAMPLE 20

6-{4-[N-[2-[3-(2-cyanophenoxy1-2-hydroxypropylamino1-2methylpropyl]carbamoylmethoxy-3-chlorophenyl}-4,5-dihvdro-3(2H)-pyridazinone A solution of 2.00 g (7.08 mmol) of 6-{4-[3-carboxymethoxy]-3-chlorophenyl}-4,5-dihydro-3(2H)-pyridazinone, prepared by the method of Eur. Pat. Appl. EP 178,189, 1.182 ml (7.79 mmol) of diethyl cyanophosphonate, and 815 microliters (7.79 mmol) of 1,2-diamino-2-methylpropane in 15 ml of DMF is cooled in an ice-water bath, and 1.036 (7.43 mmol) of triethylamine in 3 ml of DMF is added dropwise. After 30 min, the ice bath is removed and the mixture is stirred overnight at RT. The DMF is removed under vacuum and the residue flash chromatographed on silica gel (90:10:2 $CHCl_3:CH_3OH:NH_4OH$) to give 1.788 g of a white solid. This solid is twice recrystallized from EtOAc to give 1.466 g of 6-{4-[N-[2-amino-2-methylpropyl]carbamoylmethoxy]-3-chlorophenyl}-4,5-dihydro-3(2H)-pyridazinone as a white solid. Yield, 59%.

A solution of 600 mg (1.70 mmol) of the amine prepared above and 223 mg (1.28 mmol) of (2S)-3-(2-cyanophenoxy)1,2-epoxypropane in 7 ml of $CH_3OH$ is heated at reflux under $N_2$ for 15 hrs. The solvent is removed and the residue flash chromatographed on silica gel (95:5 $CHCl_3:CH_3OH$) to give 607 mg of 6-=4-[N-[2-[3-(2-cyanophenoxy)-2-hydroxypropylamino]-2-methylpropyl]carbamoylmethoxy-3-chlorophenyl]}-4,5-dihydro-3(2H)-pyridazinone as an amorphous white solid.

This solid is taken up in 5 ml of $CH_3OH$, 5 ml of ethyl ether added, and the maleate salt precipitated by adding a 0.10 M solution of maleic acid in ether. After drying overnight under vacuum at 85° C., 608 mg of the maleate salt is obtained as a white powder, m.p. 190°–191° C. Yield, 54%.

| Elemental Analysis (for $C_{26}H_{30}ClN_5O_5 \cdot C_4H_4O_4 \cdot H_2O$): | | | |
|---|---|---|---|
| | C (%) | H (%) | N (%) |
| Found: | 55.05 | 5.34 | 10.59 |
| Calculated: | 54.85 | 5.48 | 10.58 |

EXAMPLE 21

6-≡4-[N-2-[3-(2-methylphenoxy)-2-hydroxy-propylamino1-2-methylpropyl]carbamoylmethoxy-3-chlorophenyl]}-4,5-dihvdro-3(2H)pyridazinone A solution of 429 mg (1.22 mmol) of 6-{4-[N-[2-amino-2-methylpropyl]carbamoylmethoxy-3chlorophenyl}-4,5-dihydro-3(2H)-pyridazinone, prepared as described in Example 20, and 180 mg (1.10 mmol) of (2S)-3-(2-methylphenoxy)-1,2-epoxypropane in 5 ml of ethanol is heated at reflux under $N_2$ for 24 hrs. The solvent is removed and the residue flash chromatographed on silica gel (95:5 $CHCl_3$:$CH_3OH$) to give 501 mg of an amorphous white solid. This solid is taken up in 5 ml of $CH_3OH$, 5 ml of ethyl ether is added, and the maleate salt is precipitate by adding 0.1 M maleic acid in ether. After drying overnight under vacuum at 75° C., 439 mg of the maleate salt of 6-{4-[N-[2-[3-(2-methylphenoxy)-2-hydroxypropylamino]-2methylpropyl]carbamoylmethoxy-3-chlorophenyl]}-4,5-dihydro-3(2H)-pyridazinone is obtained as a white powder, m.p. 162°–165° C.

| Elemental Analysis (for $C_{26}H_{33}ClN_4O_5O \cdot C_4H_4O_4$): | | | |
|---|---|---|---|
| | C (%) | H (%) | N (%) |
| Found: | 56.81 | 5.89 | 8.83 |
| Calculated: | 56.91 | 5.89 | 8.85 |

EXAMPLE 22

6-{4-[N-2-[3-(2-chlorophenoxy)-2-hydroxy-propylamino1-2methylpropyl]carbamoylmethoxy-3-chlorophenyl]}-4,5-dihvdro-3(2H)-pyridazinone A solution of 429 mg (1.22 mmol) of 6-{4-[N-[2-amino-2-methylpropyl]carbamoylmethoxy]-3-chlorophenyl}-4,5-dihydro-3(2H)-pyridazinone, prepared as described in Example 20, and 203 mg (1.10 mmol) of (2S)-3-(2-chlorophenoxy)-1,2-epoxypropane in 5 ml of methanol is heated at reflux under $N_2$ for 24 hrs. The solvent is removed and the residue flash chromatographed on silica gel (95:5 $CHCl_3$:$CH_3OH$) to give 510 mg of 6-{4-[N-[2-[3-(2-chlorophenoxy)-2-hydroxypropylamino]-2-methylpropyl]carbamoylmethoxy-3-chlorophenyl]}-4,5-dihydro-3(2H)-pyridazinone as a white solid. The maleate salt is prepared by adding 0.10 M maleic acid in ethyl ether to a solution of the above amine in 10 ml of 1:1 $CH_3OH$:ether. After drying overnight under vacuum at 75° C., 524 mg of the maleate salt is obtained as a white powder, m.p. 181°–183° C. Yield, 71%.

| Elemental Analysis (for $C_{25}H_{30}Cl_2N_4O_5 \cdot C_4H_4O_4$): | | | |
|---|---|---|---|
| | C (%) | H (%) | N (%) |
| Found: | 53.27 | 5.23 | 8.44 |
| Calculated: | 53.30 | 5.24 | 8.57 |

EXAMPLE 23

6-{4-[N-[2-[3-phenoxy-2-hydroxypropylamino1ethyl carbamoylpropyloxy-3-chlorophenyl]}-4,5-dihvdro-3(2H)-pyridazinone A mixture of 1.500 mg (6.675 mmol) of 6-(3-chloro-4-hydroxyphenyl)-4,5-dihydro-3(2H)-pyridazinone, prepared by the method of Eur. Pat. Appl. 178,189, 1.010 g (7.34 mmol) $K_2CO_3$, and 1.463 g (7.50 mmol) of ethyl 4-bromobutyrate in 30 ml of DMF is heated at 100° C. for 2 hrs under $N_2$. The DMF is removed under vacuum and the residue taken up in 150 ml of EtOAc and 50 ml of water. The organic phase is washed with 50 ml of 5% NaOH, then saturated NaCl solution, dried ($MgSO_4$), and the solvent removed to leave a white solid. This solid is recrystallized from hexane-EtOAc to give 1.711 g of 6-[4-carboethyoxypropyloxy-3-chlorophenyl]-4,5-dihydro-3(2H)-pyridazinone as white needles, m.p. 109°–110° C.. Yield, 82%.

A solution of the ethyl ester prepared above (1.711 g, 5.05 mmol) in 16 ml of 501% aqueous ethanol containing 800 mg (20.1 mmol) of NaOH is heated at 80° C. under $N_2$ for 40 min. After cooling, the solution is diluted with an equal volume of water and extracted with ether (2×25 ml). The aqueous phase is cooled in an ice bath, acidified with 20% HCl, and the precipitate collected by suction filtration. After washing with water, the precipitate is dried under vacuum at 100° C. to give 1.145 g of 6-[4-carboxypropyloxy-3chlorophenyl]-4,5-dihydro-3(2H)-pyridazinone as a pale yellow solid, m.p. 195°–197° C. Yield, 73%.

A solution of 1.135 g (3.65 mmol) of the carboxylic acid prepared above, 634 mg (3.96 mmol) of 2-tert-butoxycarbamoylethyl amine, and 685 microliters (4.52 mmol) of diethylcyanophosphonate in 10 ml of DMF is cooled in an ice-water bath and 1.477 g (14.6 mmol) of triethylamine in 2 ml of DMF is added dropwise. After 30 min, the ice bath is removed and the mixture stirred overnight under $N_2$ at room temperature. The DMF is then removed under vacuum and the residue taken up in 150 ml of EtOAc. This solution is washed with cold 2% HCl (2×50 ml), saturated $NaHCO_3$ solution (2 x 50 ml), saturated NaCl (50 ml), dried ($MgSO_4$), and the solvent removed under vacuum to leave 1.578 g of residue. This residue is recrystallized from EtOAc to give 1.271 g of 6-[4-[N-[2-tert-butoxycarbamoylethyl]carbamoylpropyloxy]-3-chlorophenyl]-4,5-dihydro-3(2H)-pyridazinone as a white powder, m.p. 187°–188° C.

| Elemental Analysis (for $C_{21}H_{29}ClN_4O_5$): | | | |
|---|---|---|---|
| | C (%) | H (%) | N (%) |
| Found: | 55.49 | 6.55 | 12.26 |
| Calculated: | 55.68 | 6.45 | 12.37 |

A solution of 1.160 g (2.56 mmol) of the carbamate prepared above in 10 ml of $CH_2Cl_2$ is cooled in an ice bath and 10 ml of TFA added dropwise. After 30 min the ice bath is removed and the mixture stirred 2 hrs at RT. Volatiles are removed under vacuum and the residue taken up in 150 ml of acetonitrile. After adding 1.769 g (12.8 mmol) of powdered anhydrous $K_2CO_3$, the mixture is heated 2 hrs at reflux. After cooling, the solids are collected by suction filtration, placed in a soxhlet extractor, and continuously extracted overnight with the $CH_3CN$ filtrate. The $CH_3CN$ is removed under vacuum to leave 1.352 g of a white solid. $^1$H-

NMR of this solid confirms that it contains 6-[4-[2-aminoethylcarbamoylpropyloxy]-3-chlorophenyl-4,5-dihydro-3(2H)-pyridazinone presumably contaminated with potassium trifluoroacetate. Assuming complete conversion of the carbamate, this solid is 64% by weight the desired amine. This solid is used in the next step without purification.

A solution of 903 mg (2.56 mmol, assuming 64% by weight is the desired amine) of the solid containing the amine prepared above and 243 mg (1.79 mmol) of (2S)-3-phenoxy1,2-epoxypropane in 5 ml of $CH_3OH$ is heated at reflux 7 hrs under $N_2$. The solvent is removed under vacuum and the residue flash chromatographed on silica gel (500 ml 90:10 $CHCl_3$:$CH_3OH$, then 250 ml 90:10:1 $CHCl_3$:$CH_3OH$:$NH_4OH$, then 250 ml 90:10:2 $CHCl_3$:$CH_3OH$:$NH_4OH$) to give 632 mg of solid. This solid is recrystallized from EtOAc-hexane and dried overnight under high vacuum at 75° C. to give 471 mg of 6-{4-[N-[2-[3-phenoxy-2-hydroxypropylamino]ethyl]carbamoylpropyloxy-3-chlorophenyl]}-4,5-dihydro-3(2H)-pyridazinone as a white powder, m.p. 127°–131° C. Yield, 37%

EXAMPLE 24

6-{4-3-[N-2-cyanophenoxy-2-hydroxypropyl)1amino]-propyloxy-3-chlorophenyl)-4,5-dihvdro-3(2H)-pyridazinone A mixture of 3.4 g (15.1 mmol) of 6-(4-hydroxy-3-chlorophenyl)-4,5-dihydro-3(2H)-pyridazinone, prepared according to the methods described in Eur. Pat. Appl. 178,189A2, 4.87 g (18.2 mmol) of N-(3-bromopropyl)-phthalimide, and 2.30 g (16.6 mmol) of anhydrous $K_2CO_3$ in 80 ml of DMF is heated for 3 hrs at 100° C. The DMF is removed under vacuum and 150 ml of 1:1 EtOAc-$H_2O$ is added to the residue and stirred vigorously for 10 min. The solid precipitate is collected by suction filtration, washed with water (2×150 ml), washed with EtOAc (2. 50 ml), and dried under vacuum at 80° C. to give 5.45 g of 6-[4-(3-phthalimidopropyloxy)-3-chlorophenyl]-4,5-dihydro-3(2H)-pyridazinone as a white solid, m.p. 230°–232° C.

A mixture of 5.4 g (13.1 mmol) of the phthalimide prepared above and 700 microliters (14.4 mmol) of hydrazine monohydrate in 150 ml of isopropanol is heated at reflux overnight. The solvent is removed under vacuum, the residue is taken up in 15 ml of 70:30 ($CH_3OH$:$NH_4OH$) and flash chromatographed on silica gel (90:I0:2 $CHCl_3$:$CH_3OH$:$NH_4OH$) to give 2.13 g of 6-[4-(3-aminopropyl)-3-chlorophenyl]-4,5-dihydro-3(2H)-pyridazinone as a pale yellow solid. Yield, 58%.

A solution of 500 mg (1.8 mmol) of the amine prepared above and 239 mg (1.4 mmol) of (2S)-3-(2-cyanophenoxy)-1,2epoxypropane in 10 ml of $CH_3OH$ is heated at reflux under $N_2$ for 5 hrs. The solvent is removed under vacuum and the residue flash chromatographed on silica gel (90:10 $CHCl_3$:$CH_3OH$) to afford 256 mg of 6-{4-[3-N-(2-cyanophenoxy-2-hydroxypropyl)]amino]propyloxy-3-chlorophenyl}-4,5-dihydro-3(2H)-pyridazinone as a white solid, m.p. 166°–170° C. Yield, 41%.

| Elemental Analysis (for $C_{23}H_{25}ClN_4O_4.H_2O$): | | | |
|---|---|---|---|
| | C (%) | H (%) | N (%) |
| Found: | 58.20 | 5.30 | 11.77 |
| Calculated: | 58.16 | 5.73 | 11.80 |

EXAMPLE 25

6-{4-[3-N-(2-chlorophenoxy-2-hydroxypropylamino)1-propyloxy]-3-chlorophenyl}-4,5-dihvdro-3(2H)-pyridazinone A solution of 500 mg (1.8 mmol) of 6-[4-(3-aminopropyl)-3-chlorophenyl]-4,5-dihydro-3(2H)-pyridazinone, prepared as described in Example 24, and 252 mg (1.4 mmol) of (2S)-3-(2-chlorophenoxy)-1,2-epoxypropane in 10 ml of $CH_3OH$ is heated at reflux under $N_2$ for 5 hrs. The solvent is removed under vacuum and the residue is flash chromatographed on silica gel (90: 0 $CHCl_3$:$CH_3OH$) to afford 280 mg of the desired propanolamine as a white solid, m.p. 149°–152.5° C. Yield, 44%.

| Elemental Analysis (for $C_{22}H_{25}Cl_2N_3O_4.0.5H_2O$): | | | |
|---|---|---|---|
| | C (%) | H (%) | N (%) |
| Found: | 55.21 | 5.22 | 8.84 |
| Calculated: | 55.58 | 5.51 | 8.84 |

EXAMPLE 26

6-{4-[3-[N-(2-methylphenoxy)-2-hydroxypropylamino]-propyloxy]-3-chlorophenyl)-4,5-dihvdro-3(2H)[-pyridazinone A solution of 500 mg (1.8 mmol) of 6-[4-(3-aminopropyl)-3-chlorophenyl]-4,5-dihydro-3(2H)-pyridazinone, prepared as described in Example 24, and 224 mg (1.4 mmol) of (2S)-3-(2-methylphenoxy)-1,2-epoxypropane in 8 ml of $CH_3OH$ and 2 ml of DMSO is heated at reflux under $N_2$ for 5 hrs. The solvent is removed under vacuum and the residue is flash chromatographed on silica gel to afford 335 mg of the desired propanolamine as a white solid, m.p. 130°–133° C. Yield, 55%.

| Elemental Analysis (for $C_{23}H_{28}ClN_3O_4$): | | | |
|---|---|---|---|
| | C (%) | H (%) | N (%) |
| Found: | 61.66 | 6.30 | 9.42 |
| Calculated: | 61.94 | 6.33 | 9.42 |

EXAMPLE 27

6-{4-[N-[2-[3-(2-cyanophenoxy)-(2S,-hydroxypropylamino1ethyl]-carbamovlmethoxvphenyl]}-(5-)-methyl-4,5-dihvdro-3(2H)-pyridazinone A mixture of 1.08 g (5.29 mmol; of 6-(4-hydroxyphenyl)-(5S)-methyl-4,5-dihydro-3(2H)-pyridazinone (prepared according to the procedure described in Example L), 804 mg (5.82 mmol) of anhydrous $K_2CO_3$, and 1.06 g (6.34 mmol) of ethyl bromoacetate in 20 ml of DMF is heated at 100° C. for 4 hrs under N . The DMF is then removed under vacuum, and the residue partitioned between water and EtOAc The organic phase is washed with saturated NaCl, dried (MgSO4), and the solvent removed under vacuum to give 1.50 g of crude product. This material is recrystallized from ethyl acetate-hexane to give 1.26 g of 6-(4-carbethoxymethoxyphenyl)-(5S)-methyl-4,5-dihydro-3(2H)pyridazinone as a white crystalline solid, m.p. 128°–133° C. Yield 82%.

A 1.230 g (4.24 mmol) sample of the ethyl ester prepared above is dissolved in 15 ml of ethylenediamine and heat at 60° C. for 1 hr under $N_2$. TLC (85:15:2 $CHCl_3$:$CH_3OH$:$NH_4OH$) indicates no ethyl ester is present. Volatile materials are removed under high vacuum on the rotary evaporator and the residue is flash chromatographed on silica gel (250 ml of 90:10 CHCl$_3$—CH$_3$OH, 250 ml of 90:10:1 CHCl$_3$:CH$_3$OH:NH$_4$OH, 250 ml of B5:15:2, and 500 ml of 80:20:2 CHCl$_3$:CH$_3$OH:NH$_4$OH) to give 1.158 q of 6-[4-[2-aminoethylcarbamoylmethoxy]phenyl]-(5R)-methyl-4,5-dihydro-3(2H)-pyridazinone as a transparent glassy solid, 90% yield.

A solution of 1.158 g (3.80 mmol) of the amine prepared above and 500 mg (2.85 mmol) of (2S)-3-(2-cyanophenoxy)1,2-epoxypropane in 2 ml of methanol is heated overnight at reflux under N$_2$. The methanol is removed under vacuum and the residue flash chromatographed on silica gel (250 ml 95:5 CHCl$_3$:CH$_3$OH, 250 ml 90:10 CHCl$_3$—CH$_3$OH, and 500 ml of 90:10:2 CHCl$_3$:CH$_3$OH:NH$_4$OH) to give 855 mg of 6-[4-[N-[2-[3-(2-cyanophenoxy)-(2S)-hydroxypropylamino]-ethyl]carbamoylmethyoxyphenyl]}-(5S)-methyl-4,5-dihydro-3(2H)-pyridazinone as a foamy white solid.

The above solid is dissolved in 5 ml of acetone, cooled with stirring in an ice bath, and a solution of 310 mg of maleic acid in acetone (about 5 ml) added. The solution was stirred vigorously for 30 min, then allowed to stand overnight at room temperature. The crystals which had formed were collected by filtration and dried overnight at 85° C. under high vacuum to give 277 mg of the maleate salt monohydrate, m.p. 117°–119° C.

| Elemental analysis (for C$_{25}$H$_{29}$N$_5$O$_5$.H$_2$O): | | | |
|---|---|---|---|
| | C % | H % | N % |
| Found: | 56.51 | 5.58 | 11.40 |
| Calculated: | 56.76 | 5.75 | 11.41 |

The solvent was removed from the filtrate under vacuum, and the residue triturated with EtOAc. The EtOAc is decanted from the oily residue which was dried overnight under high vacuum at 50° C. to give an additional 505 mg of maleate salt as a foamy white solid hemihydrate, m.p. 58°–63° C.

| Elemental analysis (for C$_{25}$H$_{29}$N$_5$O$_5$.½H$_2$O): | | | |
|---|---|---|---|
| | C % | H % | N % |
| Found: | 57.62 | 5.62 | 11.27 |
| Calculated: | 57.61 | 5.67 | 11.58 |

EXAMPLE 28

6-{4-[N-[2-[3-(2-Cyanophenoxy)-(2S)-hydroxypropylamino1ethyl]carbamoylmethoxyphenyl]}-(5R)-methyl-4,5-dihvdro-3(2H)-pyridazinone Following the procedure described in Example 27, a mixture of 1.07 g (5.24 mmol) of 6-(4-hydroxyphenyl)-(5R)-methyl-4,5-dihydro-3(2H)-pyridazinone (prepared according to the procedure described in Example K), 804 mg of anhydrous K$_2$CO$_3$, and 1.06 g (6.34 mmol) of ethyl bromoacetate in converted to 1.093 g of 6-(4-carbethoxymethoxyphenyl)-(5R)-methyl-4,5-dihydro-3(2H)-pyridazinone obtained as a white crystalline solid after recrystallization from hexane-EtOAc, m.p. 128°–131° C. Yield, 72%.

A mixture of 1.093 g (3.77 mmol) of the ethyl ester prepared above and 15 ml of ethylenediamine is heated under N$_2$ at 60° C. for 1 hr. The volatile materials are removed under vacuum and the residue flash chromatographed on silica gel as described in Example 27 to give 1.002 g of 6-[4-[2-aminoethylcarbamoylmethoxy]-phenyl]-(5R)-methyl-4,5-dihydro-3(2H)-pyridazinone as a foamy white solid, yield 87%.

A solution of 1.002 g (3.29 mmol) of the amine prepared above and 432 mg (2.47 mmol) of (2S)-3-(2-cyanophenoxy)-1,2-epoxypropane in 15 ml of methanol is heated overnight at reflux under N$_2$. The methanol is removed under vacuum and the residue flash chromatographed on silica gel as described in Example 27 to give 770 mg of 6-{4-[N-[2-[3-(2-cyanophenoxy)-(2S)-hydroxypropylamino]ethyl]carbamoylmethoxyphenyl]}-(5R)-methyl-4,5-dihydro-3(2H)-pyridazinone as a white solid. This solid is triturated with boiling acetone, collected by filtration, and dried overnight under high vacuum at 100° C. to give 624 mg of a white powder, m.p. 170°–171° C. Yield 53%.

| Elemental analysis (for C$_{25}$H$_{29}$N$_5$O$_5$): | | | |
|---|---|---|---|
| | C % | H % | N % |
| Found: | 62.41 | 6.24 | 14.48 |
| Calculated: | 62.61• | 6.10 | 14.61 |

The amine obtained above (1.373 g, 2.86 mmol) is suspended in 15 ml of methanol, stirred vigorously while cooling with an ice water bath, and 5 ml of a methanolic HCl solution ($\approx$0.1 g HCl/ml) added. After stirring 15 min the precipitate is collected, dried at 100° C. under high vacuum to give 1.477 g of the propanolamine as its hydrochloride salt, m.p. 210°–212° C.

| Elemental analysis (for C$_{25}$H$_{29}$N$_5$O$_5$.HCl): | | | |
|---|---|---|---|
| | C % | H % | N % |
| Found: | 57.72 | 5.83 | 13.50 |
| Calculated: | 58.19 | 5.86 | 13.57 |

EXAMPLE 29

6-(4-[N-[2-[3-(2-Cyanophenoxy)-(2S)-hydroxypropylamino1-2methylpropyl]carbamoylmethoxyphenyl]}-(5S)-methyl-4,5-dihydro-3(2H)-pyridazinone A mixture of 620 mg (2.1 mmol) of 6-(4-carbethoxymethoxyphenyl)-(5S)-methyl-4,5-dihydro-3(2H)-pyridazinone (obtained as described in Example 27) and 570 mg (6.6 mmol) of 1,2-diamino-2-methylpropane in 10 ml of methanol is heated under N$_2$ at reflux for 4 hr. The mixture is concentrated in vacuo and purified by flash chromatography on silica gel (94:6 CHCl$_3$:CH$_3$OH) to give 430 mg of 6-{4-[N-[2-amino-2-methylpropyl]carbamoylmethoxy]phenyl]}-(5S)-methyl-4,5-dihydro-3(2H)-pyridazinone as a while foamy solid. [α]$_D$+212°(c 0.4,methanol).

A mixture of the amine prepared above (910 mg, 2.7 mmol), 480 mg (2.7 mmol) of (2S)-3-(2-cyanophenoxy)-1,2-epoxypropane, and 15 ml of methanol is heated at reflux under N$_2$ for 12 hrs, the solvent removed under vacuum, and the residue flash chromatographed on silica gel (90:10 CHCl$_3$:CH$_3$OH) to give 950 mg of 6-{[4-[N-[2-[3-(2-cyanophenoxy)-(2S)-hydroxypropylamino]-2-methylpropyl]carbamoylmethoxyphenyl]}-(5S)-methyl-4,5-dihydro-3(2H)-pyridazinone as a white foamy solid. [α]$_C$+131° (c 0.445, methanol).

The foamy solid is dissolved in EtOAc (35 ml), cooled in an ice bath, and 27 ml (3 mmol) of a 0.11M maleic acid solution in ether added. The precipitate which turned to an oil was obtained by decanting off the solvent and drying under high vacuum to 890 mg of the maleate salt as a white foam, m.p. 70°-73° C. $[\alpha]_D +109°$ (c 0.245, methanol). Yield, 52%.

| Elemental analysis (for $C_{31}H_{37}N_5O_9.3/2H_2O$): | | | |
|---|---|---|---|
| | C % | H % | N % |
| Found: | 57.31 | 6.15 | 10.67 |
| Calculated: | 57.22 | 6.20 | 10.76 |

EXAMPLE 30

6-{4-[N-[2-[3-(2-Cyanophenoxy)-(2S)-hydroxypropylamino1-2methylpropyl]carbamoylmethoxyphenyl]}-(5R)-methyl-4,5-dihydro-3(2H)-pyridazinone A mixture of 1.2 g (4. mmol) of 6-(4-carbethoxymethoxyphenyl)-(5R)-methyl-4,5-dihydro-3(2H)pyridazinone (obtained as described in Example 28) and 1.11 g (12.6 mmol) of 1,2-diamino-2-methylpropane in 21 ml of methanol is converted to 1.32 g of 6-{4-[N-[2-amino-2methylpropyl]carbamoylmethoxy]phenyl])-(5R)-methyl-4,5-dihydro-3(2H)-pyridazinone as described in Example 29. The product is obtained as a foamy white solid, $[\alpha]_D -216°$ (c 0.19, methanol).

Using the procedure of Example 29, 730 mg (2.2 mmol) of the amine obtained above and 380 mg of (2S)-3-(2-cyanophenoxy)-1,2-epoxypropane in 10 ml of methanol is converted to 820 mg of 6-{4-[N-[2-[3-(2-cyanophenoxy)-(2S)-hydroxypropylamino]-2-methylpropyl]carbamoylmethoxyphenyl]}-(5R)-methyl-4,5-dihydro-3(2H)-pyridazinone, $[\alpha]_D 145°$ (c 0.48,methanol). This material is then converted to the maleate salt as described in Example 29 to give 760 mg of the maleate salt as an amorphous white solid, m.p. 70°-73° C. $[\alpha]_D 145°$ (c 0.375, methanol).

| Elemental analysis (for $C_{31}H_{27}N_5O_9.3/2H_2O$) | | | |
|---|---|---|---|
| | C % | H % | N % |
| Found: | 57.36 | 6.21 | 10.65 |
| Calculated: | 57.22 | 6.20 | 10.76 |

EXAMPLE 31

6-{4-N-[2-[3-(2-Cyanophenoxy)-(2S)-hydroxypropylamino1 ethyl]carbamoylmethoxyphenyl]}-4,5-dihydro-3(2H1-pyridazinone A mixture of 2.85 g (10.3 mmol) of 6-(4-carbethoxymethoxyphenyl)-4,5-dihydro-3(2H)-pyridazinone (prepared as described in Example 13) and 9.3 g (155 mmol) of ethylenediamine is heated at 60° C. under $N_2$ for 30 min. Volatile materials are removed in vacuo, and the residue is recrystallized from methanol-EtOAc to give 2.40 g of 6-[4-[2-aminoethylcarbamoylmethoxy]phenyl]-4,5-dihydro3(2H)-pyridazinone as a white solid, m.p. 176°-177.5° C. Yield, 80%.

A mixture of 621 mg (2.1 mmol) of the above amine and 250 mg (1.4 mmol) of (2S)-3-(2-cyanophenoxy)-1,2-epoxypropane in 10 ml of methanol is heated at reflux for 5 hrs. The solvent is removed under vacuum and the residue flash chromatographed on silica gel (500 ml of 90:10 $CHCl_3$:$CH_3OH$, 500 ml of 90:10:1 $CHCl_3$:$CH_3OH$:$NH_4OH$) to give a white solid. This solid is triturated with boiling acetone to give 350 mg of 6-{4-[N-[2-[3-(2-cyanophenoxy)-(2S)-hydroxypropylamino]ethyl]carbamoylmethoxyphenyl]}-4,5-dihydro-3(2H)-pyridazinone as a white powder, m.p. 144°-149° C.

| Elemental analysis (for $C_{24}H_{27}N_5O_5.\frac{1}{2}H_2O$): | | | |
|---|---|---|---|
| | C % | H % | N % |
| Found: | 61.30 | 5.78 | 14.78 |
| Calculated: | 60.74 | 5.84 | 14.76 |

The above propanolamine is converted to the hydrochloride salt by the addition of methanolic HCl. From 195 mg of the amine, 202 mg of the hydrochloride salt is obtained as a white solid, m.p. 244°-247° C.

| Elemental analysis (for $C_{24}H_{27}N_5O_5.HCl$): | | | |
|---|---|---|---|
| | C % | H % | N % |
| Found: | 57.32 | 5.64 | 13.91 |
| Calculated: | 57.42 | 5.62 | 13.95 |

EXAMPLE 32

6-{4-[N-[2-3-(2-Cyanophenoxy)-(2S)-hydroxypropylamino]-2-methylpropyl]carbamoylpropyloxyphenyl]}-4,5-dihydro-3(2H)pyridazinone A mixture of 6.80 g (22.3 mmol) of 6-[4-[3-carboethoxypropyloxy]phenyl]-4,5-dihydro-3(2H)-pyridazinone (prepared as described in Example 17 and 9.84 g (112 mmol) of 1,2-diamino-2-methylpropane is heated at 100° C. under $N_2$ for 12 hrs. The volatiles are removed in vacuo and the residue flash chromatographed on silica gel (90:10:2 $CHCl_3$:$CH_3OH$:$NH_4OH$) to give a white foamy solid. This recrystallized from methanol EtOAc to give 3.2 g of 6-[4-[N-(2-amino-2-methylpropyl)carbamoylpropyloxy]phenyl]-4,5-dihydro-3(2H)-pyridazinone as a white solid, m.p. 112°-114° C.

A mixture of 600 mg (1.73 mmol) of the amine prepared above and 303 mg (1.73 mmol) of (2S)-3-(2-cyanophenoxy)1,2-epoxypropane in 10 ml of methanol is heated at 80° C. overnight under $N_2$. The solvent is removed in vacuo and the residue flash chromatographed on silica gel (90:10 $CHCl_3$—$CH_3OH$ to afford 650 mg of 6-{4-[N-[2-[3-(2-cyanophenoxy)-(2S)-hydroxypropylamino]-2methylpropyl]carbamoylpropyloxyphenyl]}-4,5-dihydro-3(2H)pyridazinone as a foamy white solid. This solid is converted to the hydrochloride salt by treatment with methanolic HCl. A total of 580 mg of the hydrochloride salt is obtained as a white powder, m.p. 102°-108° C.

| Elemental analysis (for $C_{28}H_{35}N_5O_5.HCl.H_2O$): | | | |
|---|---|---|---|
| | C % | H % | N % |
| Found: | 58.40 | 6.52 | 12.00 |
| Calculated: | 58.37 | 6.64 | 12.15 |

EXAMPLE 33

6-{4-[N-2-[3-(2-Cyanophenoxy)-(2S)-hydroxypropylamino1ethyl]-carbamoylpropyloxyphenyl]}-4,5-dihydro-3(2H)pyridazinone A mixture of 3.00 g (10.9 mmol) of 6-[4-[3-carboxypropyloxy]phenyl]-4,5-dihydro-3(2H)-pyridazinone (prepared as described in Example 17), 1.92 g (11.9 mmol) of 2-tert-butoxycarbamoylethyl amine, 1.95 g (11.9 mmol) of diethycyanophosphonate, and 3.3 ml of triethylamine in 60 ml of DMF is converted to 4.30 g of 6-[4-[N-[2-tert-butoxycarbamoylethyl]carbamoyl-propyloxyphenyl-4,5-dihydro-3(2H)-pyridazinone, obtained as a white crystalline solid, m.p. 165°-167° C., as described in Example 17.

The carbamate prepared above (4.20 g, 10.0 mmol) is deprotected with TFA in $CH_2Cl_2$ followed by extraction with $K_2CO_3$ and flash chromatography on silica gel (90:10:2 $CHCl_3:CH_3OH:NH_4OH$) as described in Example 17 to give a White solid. After recrystallization from methanol-EtOAc, 2.25 g of 6-[4-[2-aminoethylcarbamoylpropyloxy]phenyl]-4,5-dihydro-3(2H)-pyridazinone is obtained as a white crystalline solid, m.p. 174°-175° C. Yield, 70%.

A solution of the amine prepared above (680 mg, 2.1 mmol) and 250 mg (1.4 mmol) of (2S)-3-(2-cyanophenoxy)-1,2epoxypropane in 10 ml of methanol is heated for 5 hrs at reflux under $N_2$. The solvent is removed under vacuum and the residue flash chromatographed on silica gel (500 ml 90:10 $CHCl_3:CH_3OH$) to give a white solid. This solid is recrystallized from methanol-EtOAc to give 395 mg of 6-{4-[N-[2-[3-(2-cyanophenoxy-(2S)-hydroxy-propylamino]ethyl]carbamoylpropyloxyphenyl]}-4,5-dihydro-3(2H)-pyridazinone as a white crystalline solid, m.p. 105°-108° C. Yield, 56%.

| Elemental analysis (for $C_{26}H_{31}N_5O_5$): | | | |
|---|---|---|---|
| | C % | H % | N % |
| Found: | 62.88 | 6.37 | 14.24 |
| Calculated: | 63.27 | 6.33 | 14.19 |

EXAMPLE 34

6-{4-[N-[2-(2-Cyano-5-chlorophenoxy)-(2S)-hydroxypropylamino]-2-methylpropyl11carbamoylmethoxyphenyl]}-4.5-dihydro-3(2H)-pyridazinone A mixture of 400 mg (1.3 mmol) of 6-[4-[N-(2-amino-2methylpropyl) carbamoylmethoxy]phenyl]-4,5-dihydro-3(2H)-pyridazinone (prepared as described in Example 14) and 263 mg (1.3 mmol) of (2S) -3-(2-cyano-5-chlorophenoxy)-1,2-epoxypropane in 10 ml of methanol is heated at 80° C. overnight. The solvent is removed under vacuum and the residue flash chromatographed on silica gel (90:10: $CHCl_3$—$CH_3OH$) to afford 310.mg of 6-{4-[N-[2-[(2-cyano-5-chlorophenoxy)-(2S)-hydroxypropylamino]-2-methylpropyl]carbamoylmethoxyphenyl]}-4,5-dihydro-3(2H)-pyridazinone as a white powder, m.p. 78°-85° C.

| Elemental analysis (for $C_{26}H_{29}ClN_5O_5.H_2O$): | | | |
|---|---|---|---|
| | C % | H % | N % |
| Found: | 57.36 | 5.82 | 12.73 |
| Calculated: | 57.19 | 5.90 | 12.82 |

EXAMPLE 35

6-{4-[N-[2-3-(2-Cyanophenoxy)-(2S)-hydroxypropylamino1ethyl]carbamoylmethoxy]-3-chlorophenyl}-4.5-dihydro-3(2H)pyridazinone A solution of 1.0 g (3.2 mmol) of 6-(4-carboethoxymethoxy-3-chlorophenyl)-4,5-dihydro-3(2H)-p-pyridazione (prepared according to Eur. Pat. Application EPO 178189) and 2.69 g (45 mmol) of ethylenediamine is heated at 60° C. under $N_2$ for 20 min. Volatiles are removed under vacuum and the residue recrystal- lized from EtOAc-methanol to give 950 mg of 6-[4-[2-aminoethylcarbamoylmethoxy] -3-chlorophenyl]-4,5-dihydro-3(2H)-pyridazinone as a white crystalline solid, m.p. 168-170° C. Yield, 91%.

A solution of 422 mg (1.3 mmol) of the amine prepared above and 175 mg (1.0 mmol) of (2S)-3-(2-cyanophenoxy)1,2-epoxypropane in 5 ml of methanol is heated at for reflux 3 hrs under $N_2$. The solvent is removed and the residue flash chromatographed on silica gel (90:10:1 $CHCl_3$—$CH_3OH:NH_4OH$) to afford 302 mg of 6-{4-[N-[2-[3-(2-cyanophenoxy)-(2S)-hydroxypropylamino]ethyl]carbamoylmethoxy]-3-chlorophenyl}-4,5-dihydro-3(2H)-pyridazinone as a white powder, m.p. 190°-192° C. Yield, 60%.

The HCl salt of the above propanolamine is prepared by treating 181 mg with methanolic HCl to give 185 mg of the hydrochloride salt as a white powder, m.p. 223°-225° C.

| Elemental analysis (for $C_{24}H_{26}ClN_5O_5.HCl$): | | | |
|---|---|---|---|
| | C % | H % | N % |
| Found: | 53.33 | 5.09 | 13.20 |
| Calculated: | 53.74 | 5.07 | 13.06 |

EXAMPLE 36

6-{4-N-[2-[3-(2-Cyanophenoxy)-(2S)-hydroxypropylamino1-2-propyl]carbamoylmethoxy-3-chlorophenyl}-4,5-dihydro-3(2H)pyridazinone A solution of 1.00 g (3.22 mmol) of 6-[4-carboethoxymethoxy-3-chlorophenyl]-4,5-dihydro-3(2H)-pyridazinone (prepared according to Eur. Pat. application EPO 178,189) in 10 ml of 1,2-diaminopropane is heated at 45°-50° C. under $N_2$ for thirty min. Volatiles are removed under vacuum and the residue is recrystallized from EtOAc to give 984 mg of a white solid. $^1$H-NMR of this solid shows it to consist of 85% 6-[4-[2-aminopropylcarbamoylmethoxy]-3chlorophenyl]-4,5-dihydro-3(2H)-pyridazinone and 15% 6-[4-[2-amino-1-methylethylcarbamoylmethoxy]-3-chlorophenyl]-4,5-dihydro-3(2H)-pyridazinone. This mixture is used in the next step without further purification.

A solution of 975 mg (2.88 mmol) of the amine prepared above and 378 mg (2.16 mmol) of (2S)-3-(2-cyanophenoxy)-1,2-epoxypropane in 15 ml of methanol is heated at reflux overnight under $N_2$. The solvent is removed under vacuum and the residue flash chromatographed in silica gel (250 ml 95:5 $CHCl_3:CH_3OH$ then 500 ml 90:10 $CHCl_3:CH_3OH$) to give 872 mg of a foamy White solid. This solid is recrystallized from acetone to give 616 mg of 6-{4-[N-[2-[3-(2-cyanophenoxy)-(2S)-hydroxypropyl-amino]-2-propyl]carbamoylmethoxy-3-chlorophenyl]}-4,5-dihydro-3(2H)-pyridazinone, m.p. 147°-149° C. Concentration of the acetone filtrate gave a second 163 mg batch of solid, m.p. 147-149° C. $^1$H-NMR of both solids indicates contamination by $\approx 16\%$ of the isomeric 6-{4-[N-[2-[3-(2-cyanophenoxy)-(2S)-hydroxypropylamino]-(1-methylethyl)]carbamoylmethoxy-3-chlorophenyl]}-4,5-dihydro-pyridazinone.

| Elemental analysis (for $C_{25}H_{28}ClN_5O_5$): | | | |
|---|---|---|---|
| | C % | H % | N % |
| Found: | 58.09 | 5.49 | 13.43 |

-continued

| Elemental analysis (for $C_{25}H_{28}ClN_5O_5$): | | | |
|---|---|---|---|
| | C % | H % | N % |
| Calculated: | 58.42 | 5.49 | 13.63 |

EXAMPLE 37

6-{4-[N-2-[3-(2-Nitrophenoxy)-(2S)-hydroxypropylamino1-2methvpropvl]carbamoylmethoxy-3-chlorophenyl]}-4,5-dihydro-3(2H)-pyridazinone A solution of 600 mg (1.70 mmol) of 6-{4-[N-[2-amino-2-methylpropyl]carbamoylmethoxy]-3-chlorophenyl}-4,5-dihydro-3(2H)-pyridazinone (prepared as described in Example 20) and 332 mg (1.70 mmol) of (2S)-3-(2-nitrophenoxy)-1,2-epoxypropane in 7 ml of methanol is heated overnight at reflux under $N_2$. Solvent is removed under vacuum and the residue flash chromatographed on silica gel (250 ml of 95:5 $CHCl_3$:$CH_3OH$, 250 ml 90:10:1 $CHCl_3$—$CH_3OH$—$NH_4OH$, 500 ml 190:10:2 $CHCl_3$:$CH_3OH$:$NH_4OH$) to give 688 mg of 6-{4-[N-[2-[3-(2-nitrophenoxy)-(2S)-hydroxypropylamino]-2-methylpropyl]carbamoylmethoxy-3-chlorophenyl]}-4,5-dihydro-3(2H)-pyridazinone as a pale yellow powder.

The yellow powder is dissolved in 10 ml of methanol and treated with an excess of maleic acid in ether to give 795 mg of the maleate salt as a white powder, m.p. 198° C.(d).

| Elemental analysis (for $C_{29}H_{34}ClN_5O_{11}$): | | | |
|---|---|---|---|
| | C % | H % | N % |
| Found: | 52.65 | 5.22 | 10.61 |
| Calculated: | 52.45 | 5.16 | 10.55 |

EXAMPLE 38

6-{4-[N-[2-3-(2-Trifluoromethylphenoxy)-(2S)-hydroxypropylamino]-2-methylpropyl11carbamoylmethoxy-3-chlorophenyl]}-4,5-dihydro-3(2H)-pyridazinone A solution of 600 mg (1.70 mmol) of 6-{4-[N-[2-amino-2-methylpropyl]carbamoylmethoxy]-3-chlorophenyl}-4,5-dihydro-3(2H)-pyridazinone (prepared as described in Example 20) and 372 mg (1.97 mmol) of (2S)-3-(2-trifluoromethylphenoxy)-1,2-epoxypropanol in 7 ml of methanol is heated at reflux overnight under $N_2$. Solvent is removed under vacuum and the residue flash chromatographed on silica gel (250 ml of 95:5 $CHCl_3$:$CH_3OH$, 250 ml 90:10:1 $CHCl_3$:$CH_3OH$:$NH_4OH$, 500 ml 90:10:2 $CHCl_3$:$CH_3OH$:$NH_4OH$) to give 748 mg of 6-{4-[N-[2-[3-(2-trifluoromethylphenoxy)-(2S)-hydroxy-propylamino]-2-methylpropyl]carbamoylmethoxy]-3-chlorophenyl]}-4,5-dihydro-3(2H)pyridazinone as a white solid. This solid is dissolved in 10 ml of methanol and treated with an excess of maleic acid in ether to give the maleate salt (789 mg) as a white powder, m.p. 198°-201° C.(d)

| Elemental analysis (for $C_{30}H_{36}ClF_3N_4O_{10}$): | | | |
|---|---|---|---|
| | C % | H % | N % |
| Found: | 52.52 | 4.95 | 8.20 |
| Calculated: | 52.44 | 4.99 | 8.16 |

EXAMPLE 39

6-{4-N-[2-[3-(2-Cyano-5-chlorophenoxy)-(2S)-hydroxypropylamino]-2-methylpropyl11carbamoylmethoxy-3-chlorophenyl]}-4,5-dihydro-3(2H)-pyridazinone A solution of 500 mg (1.4 mmol) of 6-{4-[N-[2-amino-2-methylpropyl]carbamoylmethoxy]-3chlorophenyl}-4,5-dihydro-3(2H)-pyridazinone (prepared as described in Example 20) and 282 mg (1.35 mmol) of (2S)-3-(2-cyano-5-chlorophenoxy)-1,2-epoxypropane in 10 ml of methanol is heated at reflux overnight under $N_2$. Solvent is removed under vacuum and the residue flash chromatographed on silica gel (90:10 $CHCl$ $CH_3OH$) to give 610 mg of 6-(4-[N-[2-[3-(2-cyano-5-chlorophenoxy)-(2S)- o hydroxypropylamino]-2-methylpropyl]carbamoylmethoxy-3-chlorophenyl-4,5-dihydro-3(2H)-pyridazinone as a white powder, m.p. 90°-97° C.

| Elemental analysis (for $C_{26}H_{29}Cl_2N_5O_5 \cdot \frac{1}{2}H_2O$): | | | |
|---|---|---|---|
| | C % | H % | N % |
| Found: | 54.65 | 5.34 | 12.26 |
| Calculated: | 54.64 | 5.29 | 12.26 |

EXAMPLE 40

6-{4-N-[2-[3-(3,4-Dichlorophenoxy)-(2S)-hydroxypropylamino]-2-methylpropyl]carbamoylmethoxy-3-chlorophenyl]}-4,5-dihydro-3(2H)-pyridazinone A solution of 600 mg (1.7 mmol)of 6-{4-[N-[2-amino-2-methylpropyl]carbamoylmethoxy]-3-chlorophenyl}-4,5-dihydro-3(2H)-pyridazinone (prepared as described in Example 20) and 373 mg (1.7 mmol) of (2S)-3-(3,4-dichlorophenoxy)-1,2-epoxypropane in 10 ml of methanol is heated at reflux overnight under $N_2$. Solvent is removed under vacuum and the residue flash chromatographed on silica gel (95:5 $CHCl_3$:$CH_3OH$) to afford 690 mg of 6-{4-[N-[2-[3-(3,4-dichlorophenoxy)-(2S)-hydroxypropylamino]-2-methylpropyl]carbamoylmethoxy-3-chlorophenyl]}-4,5-dihydro-3(2H)-pyridazinone as a white solid. This solid is dissolved in EtOAc and treated with excess gaseous HCl to give 643 mg of the hydrochloride salt as a white powder, m.p. 127°-134° C(d).

| Elemental Analysis (for $C_{25}H_{29}Cl_3N_4O_5 \cdot HCl \cdot \frac{1}{2}H_2O$): | | | |
|---|---|---|---|
| | C % | H % | N % |
| Found: | 48.64 | 5.09 | 8.77 |
| Calculated: | 48.63 | 5.06 | 9.07 |

EXAMPLE 41

6-{4-[N-2-[3-(2,3-Dichlorophenoxy)-(2S)-hydroxypropylamino]-2-methylpropyl11carbamoylmethoxy-3-chlorophenyl]}-4.5-dihydro-3(2H)pyridazinone A solution of 600 mg (1.70 mmol) of .6-{4-[N-[2-amino-2-methylpropyl]carbamoylmethoxy]-3-chlorophenyl)-4,5-dihydro-3(2H)-pyridazinone (prepared as described in Example 20) and 373 mg (1.7 mmol) of (2S)-3-(2,3-dichlorophenoxy)-1,2-epoxypropane in 10 ml of methanol is heated 24 hr at reflux under $N_2$. Solvent is removed under vacuum, and the residue flash chromatographed on silica gel (95:5 $CHCl_3$—$CH_3OH$) to give 570 mg of 6-{4-[N-[2-[3-(2,3-dichlorophenoxy)-(2S)-hydroxypropylamino]-2-methylpropyl]carbamoylmethoxy-3-chlorophenyl]}-4,5-dihydro-3(2H)-pyridazinone as a white foamy solid. This solid is dissolved in EtOAc and treated with excess gaseous HCl to give 530 mg of the hydrochloride salt as a white powder, m.p. 175°-180° C.

| Elemental Analysis (for $C_{25}H_{29}Cl_3N_4O_5.HCl.\frac{1}{2} H_2O$): | | | |
|---|---|---|---|
| | C % | H % | N % |
| Found: | 48.65 | 5.16 | 8.73 |
| Calculated: | 48.63 | 5.06 | 9.07 |

EXAMPLE 42

6-{4-N-2-3-(2-Cyanophenoxy)-(2S)-hydroxypropylamino]-2-methylpropyl]carbamoylpropyloxy-3-chlorophenyl]}-4,5-dihydro-3(2H)-pyridazinone Using the procedure described in Example 14, a mixture of 3 58 g (11.5 mmol) of 6-(4-carboxypropyloxy-3-chlorophenyl)-4,5-dihydro-3(2H)-pyridazinone (prepared as described in Example 23), 1.12 g (12.7 mmol) of 1,2-diamino-2-methylpropane, 2.07 g (12.7 mmol) of diethyl cyanophosphonate, and 1.75 ml of triethylamine in 60 ml of DMF is converted to 3.64 g of 6-{4-[N-[2-amino-2-methylpropyl]carbamoylpropyloxy-3-chlorophenyl]}-4,5-dihydro-3(2H)-pyridazinone, obtained as a white crystalline solid, m.p. 101°-103° C.

A solution of 500 mg (1.31 mmol) of the above amine and 209 mg (1.19 mmol) of (2S)-3-(2-cyanophenoxy)-1,2-epoxypropane in 10 ml of methanol is heated at reflux for 16 hrs under $N_2$. Solvent is removed and the residue flash chromatographed on silica gel (95:5 $CHCl_3:CH_3OH$) to give 360 mg of 6-{4-[N-[2-[3-(2-cyanophenoxy)-(2S)-hydroxypropylamino]-2-methylpropyl]carbamoylpropyloxy-3-chlorophenyl]}-4,5-dihydro-3(2H)-pyridazinone as a white powder, m.p. 65°-75° C.

| Elemental Analysis (for $C_{28}H_{34}ClN_5O_5.H_2O$): | | | |
|---|---|---|---|
| | C % | H % | N % |
| Found: | 58.82 | 6.30 | 12.22 |
| Calculated: | 58.58 | 6.32 | 12.20 |

EXAMPLE 43

6-{4-[N-[2-3-(2-Cyanophenoxy)-(2S)-hydroxypropylamino1ethyl]carbamoylpropyloxy-3-chlorophenyl]}-4,5-dihydro-3(2H)pyridazinone A solution of 4.5 g (13.3 mol) of 6-[4-carboethoxypropyloxy-3-chlorophenyl]-4,5-dihydro-3(2H)-pyridazinone (prepared as described in Example 23) in 12.0 g 199 mmol) of ethylenediamine is heated at 95° C. under $N_2$ for 12 hrs. Volatiles are removed under vacuum and the residue recrystallized from EtOAc-methanol to give 3.65 g of 6-{4-[2-aminoethylcarbamoylpropyloxy]-3-chlorophenyl}-4,5-dihydro-3(2H)-pyridazinone as a white powder. Yield, 78%.

A solution of 755 mg (2.1 mmol) of the above amine and 250 mg (1.4 mmol) of (2S)-3-(2-cyanophenoxy)-1,2-epoxypropane in 10 ml of methanol is heated at reflux 5 hrs under $N_2$. Solvent is removed under vacuum and the residue flash chromatographed on silica gel (500 ml 90:10 $CHCl_3—CH_3OH$, 1000 ml 90:10:1 $CHCl_3:CH_3OH:NH_4OH$) to afford a white foamy solid. This is recrystallized from acetone to give 410 mg of 6-{4-[N-[2-[3-(2-cyanophenoxy)-(2S)-hydroxypropylamino]ethyl]carbamoylpropyloxy-3-chlorophenyl]}-4,5-dihydro-3(2H)-pyridazinone as a white powder, m.p. 108°-113° C..

| Elemental Analysis (for $C_{26}H_{30}ClN_5O_5.\frac{1}{2} H_2O$): | | | |
|---|---|---|---|
| | C % | H % | N % |
| Found: | 58.53 | 5.70 | 13.01 |
| Calculated: | 58.14 | 5.81 | 13.04 |

The above solid (247 mg) was added to 10 ml of methanol and treated with excess methanolic HCl to give the hydrochloride salt as a white powder, 229 mg, m.p. 163°-165° C.

| Elemental Analysis (for $C_{26}H_{30}ClN_5O_5.HCl.\frac{1}{2} H_2O$): | | | |
|---|---|---|---|
| | C % | H % | N % |
| Found: | 54.74 | 5.68 | 12.36 |
| Calculated: | 54.54 | 5.62 | 12.21 |

EXAMPLE 44

6-{4-[N-2-[3-(2-Chlorophenoxy)-(2S)-hydroxypropylamino1-2methylpropyl]carbamoylpropyloxy-3-chlorophenyl11)-4,5-dihydro-3(2H)-pyridazinone A solution of 500 mg (1.31 mmol) of 6-{(4-[N-[2-amino-2-methylpropyl]carbamoylpropyloxy-3-chlorophenyl]}-4,5-dihydro-3(2H)-pyridazinone (prepared as described in Example 42) and 220 mg (1.19 mol) of (2S)-3-(2-chlorophenoxy)-1,2-epoxypropane in 10 ml of methanol is heated at reflux for 20 hrs under $N_2$. Solvent is removed under vacuum and the residue flash chromatographed on silica gel (95:5 CHCl to give 370 mg of 6-{4-[N-[2-[3-(2l-chlorophenoxy)-(2S)-hydroxypropylamino]-2-methylpropyl]carbamoylpropyloxy-3-chlorophenyl]}-4,5-dihydro-3(2H)-pyridazinone as a white powder, m.p. 55°-64° C.

| Elemental Analysis for $(C_{27}H_{34}Cl_2N_4O_5.\frac{1}{2} H_2O)$: | | | |
|---|---|---|---|
| | C % | H % | N % |
| Found: | 56.38 | 6.19 | 9.71 |
| Calculated: | 56.44 | 6.14 | 9.75 |

EXAMPLE 45

6-{4-[N-[2-[3-(2-Methylphenoxy)-(2S)-hydroxypropylamino1-2methylpropyl]carbamoylpropyloxy-3-chlorophenyl]}-4,5-dihydro-3(2H)-pyridazinone A solution of 500 mg of (1.31 mmol) of 6-{4-[N-[2-amino-2-methylpropyl]carbamoylpropyloxy-3chlorophenyl]}-4,5-dihydro-3(2H)-pyridazinone (prepared as described in Example 42) and 196 mg (1.19 mmol) of (2S)-3-(2-methylphenoxy)-1,2-epoxypropane in 10 ml of methanol is heated at reflux for 20 hrs under $N_2$. Solvent is removed under vacuum and the residue purified by flash chromatography on silica gel (95:5 $CHCl_3:CH_3OH$) to give 330 mg of 6-{4-[N-[2-[3-(2-methylphenoxy)-(2S)-hydroxypropylamino]-2-methylpropyl]carbamoylpropyloxy-3-chlorophenyl]}-4,5-dihydro-3(2H)-pyridazinone as a white powder, m.p. 53°-63° C.

| Elemental Analysis (for $C_{28}H_{37}ClN_4O_5 \cdot \frac{1}{4} H_2O$): | | | |
|---|---|---|---|
| | C % | H % | N % |
| Found: | 60.27 | 6.92 | 9.98 |
| Calculated: | 60.69 | 6.91 | 10.11 |

EXAMPLE 46

6-{4-[N-[2-[3-(2-Cyano-5-chlorophenoxy)-(2S)-hydroxypropylamino]-2-methylpropyl]carbamoylpropyloxy-3-chlorophenyl]}-4,5-dihydro-3(2H)-pyridazinone A solution of 400 mg (1.3 mmol) of 6-{4-[N-[2-amino-2-methylpropyl]carbamoylpropyloxy-3chlorophenyl]}-4,5-dihydro-3(2H)-pyridazinone (prepared as described in Example 42) and 263 mg (1.3 mmol) of (2S)-3-(2-cyano-5-chlorophenoxy)-1,2-epoxypropane in 10 ml of methanol is heated overnight at reflux under $N_2$. Solvent is removed under vacuum and the residue flash chromatographed on silica gel (90:10 $CHCl_3$—$CH_3OH$) to give 350 mg of 6-{4-[N-[2-[3-(2-cyano-5-chlorophenoxy)-(2S)-hydroxypropylamino]-2-methylpropyl]-carbamoylpropyloxy-3chlorophenyl]}-4,5-dihydro-3(2H)-pyridazinone as a white powder, m.p. 75°-82° C.

| Elemental Analysis (for $C_{28}H_{33}Cl_2N_5O_5 \cdot H_2O$): | | | |
|---|---|---|---|
| | C % | H % | N % |
| Found: | 55.17 | 5.65 | 11.33 |
| Calculated: | 55.26 | 5.79 | 11.50 |

EXAMPLE 47

6-{4-3-[N-[Phenoxy-(2S)-hydroxypropyl]amino]-3,3-dimethylpropyloxy1-3-chlorophenyl}-4,5-dihydro-3(2H)pyridazinone A mixture of 4.05 g (18.0 mmol) of 6-(3-chloro-4-hydroxyphenyl)-4,5-dihydro-3(2H)-pyridazinone (prepared as described in Eur. Pat. application EPO 178,189), 4.52 g (21.6 mmol) of methyl 4-bromo-2,2dimethylbutyrate (prepared by treatment of 2,2-dimethylbutyrolactone with gaseous HBr, conversion to the acid chloride with oxalyl chloride, and treatment with methanol and triethylamine), and 2.99 g (21.6 mmol) of anhydrous $K_2CO_3$ in 40 ml of DMF is heated at 100° C. for 4 hrs under $N_2$. The DMF is removed under vacuum, the residue taken up in 300 ml of 50:50 waterEtOAc, the organic phase washed with cold 5% NaOH (50 ml), then water (50 ml), and dried (MgSO$_4$). The solvent is removed under vacuum to give an oily residue The oil is crystallized by the addition of 50 ml of ethyl ether to give 4.75 g of 6-[4-(3-carbomethoxy3,3-dimethylpropyloxy)-3-chlorophenyl]-4,5-dihydro-3(2H)-pyridazinone as a white crystalline solid, m.p. 109°-110° C. Yield, 75%.

A mixture of 4.7 g (13.3 mmol) of the methyl ester prepared above and 3.51 g (53.3 mmol) of 85% KOH in 70 ml of water and 70 ml of methanol is heated at 60° C. for 24 hrs under $N_2$. The solution is concentrated under vacuum, extracted with 50 ml of EtOAc, the aqueous phase acidified to pH=3 with 10% HCl, and the resulting precipitate is collected by filtration. The precipitate is collected by filtration. The precipitate is washed with water followed by ether and dried overnight under high vacuum to give 4.31 g of 6-[4-(3-carboxy-3,3-dimethylpropyloxy)-3-chlorophenyl]4,5-dihydro-3(2H)-pyridazinone as a white crystalline solid. Yield 96%.

A mixture of 5.15 g (15.2 mmol) of the carboxylic acid prepared above, 5.02 g (18.2 mmol) of diphenyl phosphoryl azide, and 1.84 g (18.2 mmol) of triethylamine in 100 ml of benzene is heated to reflux for 2 hrs under $N_2$. The reaction is concentrated under vacuum, 100 ml of dry t-butyl alcohol added, and the mixture heated at reflux under $N_2$ for 5 days. Solvent is removed under vacuum, the residue taken up in 150 ml of $CHCl_3$, washed with saturated $NaHCO_3$ (2×50 ml), water (50 ml) dried ($MgSO_4$), and the solvent removed under vacuum to give a yellow solid. Recrystallization from hexane-EtOAc gives 4.51 of 6-[4-(3-tert-butoxycarbamoyl-3,3-dimethylpropyloxy)-3chlorophenyl]-4,5-dihydro-3(2H)-pyridazinone as a white crystalline solid, m.p. 133°-135° C. Yield, 72%.

A solution of 4.45 g (10.9 mmol) of the carbamate prepared above in 50 ml of $CH_2Cl_2$ is cooled in an ice bath and 40 ml of trifluoroacetic acid is added dropwise. The mixture is allowed to come to room temperature and stirred 4 hrs. Solvent is removed under high vacuum, the residue taken up in 100 ml of $CH_3CN$, 6.0 g of anhydrous $K_2CO_3$ added, and the mixture stirred 3 hrs at 60° C. The mixture is filtered and the precipitate continuously extracted overnight with a Soxhlet extractor. All $CH_3CN$ fractions were combined, the solvent removed under vacuum, and the residue flash chromatographed on silica gel (500 ml 90:10 $CHCl_3$:$CH_3OH$, 1000 ml 90:10:2 $CHCl_3$:$CH_3OH$:$NH_4OH$) to afford a white foamy solid. This is recrystallized form EtOAc to give 3.10 g of 6-[4-(3-amino-3,3-dimethylpropyloxy)-3chlorophenyl]-4,5-dihydro-3(2H)-pyridazinone as a white crystalline solid, m.p. 152°-156° C. Yield, 92%.

A solution of 500 mg (1.6 mmol) of the amine prepared above and 242 mg (1.6 mmol) of (2S)-3-phenoxy-1,2-epoxypropane in 10 ml of methanol is heated at reflux for 48 hrs under $N_2$. Solvent is removed under vacuum and the residue flash chromatographed on silica gel (95:5 $CHCl_3$:$CH_3OH$) to give 330 mg of 6-{4-[3-[N-[phenoxy-(2S)-hydroxypropyl]amino]-3,3-dimethylpropyloxy]-3-chlorophenyl}-4,5-dihydro-3(2H)-pyridazinone as a white foamy solid. This solid is converted to the HCl salt by dissolving in EtOAc and treating with gaseous HCl to give 320 mg of the hydrochloride salt as a white powder, m.p. 125°-132° C.

| Elemental Analysis (for $C_{24}H_{30}ClN_3O_4 \cdot HCl \cdot \frac{1}{4} H_2O$): | | | |
|---|---|---|---|
| | C % | H % | N % |
| Found: | 57.42 | 6.41 | 8.38 |
| Calculated: | 57.03 | 6.38 | 8.31 |

EXAMPLE 48

6-(4-[3-[N-; 2-Cyanophenoxy)-(2S)-hydroxypropyl]amino]-3,3-dimethylpropyloxy]-3-chlorophenyl)-4,5-dihydro-3(2H)pyridazinone A solution of 500 mg of (1.6 mmol) of 6-[4-(3-amino-3,3-dimethylpropyloxy)-3-chlorophenyl]-4,5-dihydro-3(2H)-pyridazinone (prepared as described in Example 47) and 283 mg (1.6 mmol) of (2S)-3-(2-cyanophenoxy)-1,2epoxypropane in 10 ml of methanol is heated at reflux overnight under $N_2$. Solvent is removed under vacuum and the residue flash chromatographed on silica gel (95:5 CHCl₃:CH₃OH) to give 330 mg of 6-{4-[3-[N-(2-cyanophenoxy)(2S)-hydroxypropyl]amino]-3,3-dimethylpropyloxy]-3-chlorophenyl}-4,5-dihydro-3(2H)-pyridazinone as a foamy white solid. This solid is taken up in 5 ml of EtOAc and converted to the HCl salt using gaseous HCl. The result is 280 mg of the hydrochloride salt obtained as a white powder, m.p. 153°-160° C.

| Elemental Analysis (for $C_{25}H_{29}ClN_4O_4 \cdot HCl \cdot \frac{1}{2} H_2O$): | | | |
|---|---|---|---|
| | C % | H % | N % |
| Found: | 56.84 | 5.82 | 10.50 |
| Calculated: | 56.60 | 5.70 | 10.56 |

EXAMPLE 49

6-(4-[3-[N-[2-Chlorophenoxy)-(2S)-hydroxypropyl]amino]-3,3-dimethylpropyloxy]-3-chlorophenyl}-4,5-dihydro-3(2H)pyridazinone A solution of 500 mg (1.6 mmol) of 6-[4-(3-amino-3,3-dimethylpropyloxy)-3-chlorophenyl]-4,5-dihydro-3(2H)-pyridazinone (prepared as described in Example 47) and 274 mg (1.48 mmol) of (2S)-3-(2-chlorophenoxy)-1,2epoxypropane in 10 ml of methanol is heated at reflux for 48 hrs. Solvent is removed under vacuum and the residue flash chromatographed on silica gel (95:5 CHCl₃:CH₃OH) to afford 340 mg of 6-{4-[3-[N-(2-chlorophenoxy)-(2S)-hydroxypropyl]amino]-3,3-dimethylpropyloxy]-3-chlorophenyl}-4,5-dihydro-3(2H)-pyridazinone as a white foamy solid. This solid is dissolved in 5 ml of EtOAc and converted to the HCl salt by treatment with gaseous HCl to give 305 mg of the hydrochloride salt as a white powder, m.p. 146°-153° C.

| Elemental Analysis (for $C_{24}H_{29}Cl_2N_3O_4 \cdot HCl \cdot \frac{1}{2} H_2O$) | | | |
|---|---|---|---|
| | C % | H % | N % |
| Found: | 53.41 | 5.94 | 7.72 |
| Calculated: | 53.39 | 5.79 | 7.78 |

EXAMPLE 50

6-{4-[N-Methyl-N-[2-[3-(2-cyanophenoxy)-(2S)-hydroxypropylamino]-2-methylpropyl]carbamoylmethoxy-3-chlorophenyl]}-4,5-dihydro-3(2H)-pyridazinone A solution of 349 mg (1.2 mmol) of 6-{4-[3-carboxymethoxy]-3-chlorophenyl}-4,5-dihydro-3-(2H)pyridazinone, prepared by the method of Eur. Pat. Appl. EPO 178,189, 206 µl (1.4 mmol) of triethylamine, and 15 ml of CHCl₃ is cooled to −10° C and 160 µl (1.2 mmol) of isobutylchloroformate added. After 15 min of stirring at −10° C., 250 mg (1.2 mmol) of N-methyl-2-methyl-2-t-butoxycarbamoylpropyl amine in 5 ml of CHCl₃ was added dropwise. After stirring 15 min at −10° C. and 15 min at 0° C., the solution is allowed to come to RT. The mixture is concentrated under vacuum and flash chromatographed on silica gel (500 ml of 50:50 hexane-EtOAc then 500 ml of 90:10 CHCl₃:CH₃OH) to give 550 mg of 6-{4-[N-methyl-N-[2-t-butoxycarbamoyl-2-methylpropyl]carbamoylmethoxy]-3-chlorophenyl}-4,5-dihydro-3(2H)-pyridazinone as a white solid. Yield 91%.

The N-methyl-2-methyl-2-t-butoxycarbamoylpropyl amine used above is prepared as follows: A mixture of 721 mg (10.7 mmol) of methylamine hydrochloride and 880 mg (10.7 mmol) of NaOAc in 15 ml of methanol is stirred for one and one-half hrs To the mixture is added 500 mg (2.7 mmol) of 2-t-butoxycarbamoyl-2-methylpropanal (prepared as described in U.S. Pat. No. 4,843,072) and 5 g of Type 3A molecular sieves. The mixture is stirred 30 min and 101 mg (1.6 mmol) of NaCNBH₃ is added all at once. The mixture is stirred overnight at RT, filtered, and the solvent removed under vacuum. The residue is flash chromatographed on silica gel (90:10:2 CHCl₃:CH₃OH:NH₄OH) to give 230 mg of the amine as an oil. Yield, 43%

A solution of 750 mg (1.6 mmol) of 6-{4-[N-methyl-[2-t-butoxycarbamoyl-2-methylpropyl]carbamoylmethoxy]-3-chlorophenyl}-4,5-dihydro-3(2H)-pyridazinone in 7 ml of CH₂Cl₂ is cooled to 0° C. and treated with 7 ml of trifluoroacetic acid. The mixture is allowed to come to RT and stirred 3 hrs. Solvent is removed under vacuum and the residue taken up in 15 ml of CH₃CN, treated with 890 mg (6.4 mmol) of anhydrous K₂CO₃, and heated to 60° C. for 2 hrs. The mixture is filtered and the solvent removed under vacuum. The residue is flash chromatographed on silica gel (90:10:1 CHCl₃:CH₃OH:NH₄OH) to give a white solid. This solid is recrystallized from EtOAc to give 510 mg of white solid which nmr shows to be ≈63% 6-{4-[N-methyl-N-[2-amino-2-methylpropyl]carbamoylmethoxy]-chlorophenyl}-4,5-dihydro-3(2H)-pyridazinone and ≈37% 6-{4-[N-[3-(N-methylamino)-2-methyl-2-propyl]carbamoylmethoxy]-3-chlorophenyl}-4,5-dihydro-3(2H)-pyridazinone.

A 500 mg (1.4 mmol) sample of the mixture of amines obtained above is dissolved in 10 ml of methanol and 239 mg (1.4 mmol) of (2S)-3-(2-cyanophenoxy)-1,2-epoxypropane and the mixture is heated at reflux under N₂ for 3 days. The solvent is removed under vacuum and the residue flash chromatographed on silica gel (90:10 CHCl₃:CH₃OH) to afford 20 mg of 6-[4-[N-methyl-N-[2-[3-(2-cyanophenoxy-(2S)hydroxypropylamino]-2-methylpropyl]carbamoylmethoxy-3chlorophenyl]}-4,5-dihydro-3(2H)-pyridazinone as a foamy white solid. This material is converted to the hydrochloride salt by treatment with methanolic HCl to give 110 mg of the HCl salt, m.p. 134°-141° C.

| Elemental analysis (for $C_{27}H_{32}Cl_5NO_5 \cdot HCl \cdot \frac{1}{2} H_2O$): | | | |
|---|---|---|---|
| | % C | % H | % N |
| Found: | 55.20 | 5.86 | 11.53 |
| Calculated: | 55.19 | 5.83 | 11.92 |

EXAMPLE 51

The following examples illustrate pharmaceutical formulations according to the invention containing 6-{4-[N-[2-[3-(2-cyanophenoxy)-2-hydroxypropylamino]-2-methyl-propyl]carbamoylmethoxy-3-chlorophenyl]}-4,5-dihydro-3(2H)-pyridazinone as the active ingredient. Other compounds of the invention may be formulated in a very similar manner.

| TABLETS FOR ORAL ADMINISTRATION DIRECT COMPRESSION | |
|---|---|
| | mg/tablet |
| Active Ingredient | 25 |
| Calcium hydrogen phosphate B.P.* | 72.5 |
| Croscarmellose sodium USP | 2.00 |

| TABLETS FOR ORAL ADMINISTRATION | |
|---|---|
| DIRECT COMPRESSION | mg/tablet |
| Magnesium sterate, B.P. | 0.50 |
| Compression Weight | 100 mg |

*of a grade suitable for direct compression

The active ingredient is sieved before use. The calcium hydrogen phosphate, croscarmellose sodium and active ingredient are weighed into a clean polythene bag. The powders are mixed by vigorous shaking then the magnesium stearate is weighed and added to the mix which is blended further. The mix is then compressed using a Manesty F3 tablet machine fitted with 5.5 mm flat beveled edge punches, into tablets with target compression weight of 100 mg.

Tablets may also be prepared by other conventional methods such as wet granulation.

Tablets of other strengths may be prepared by altering the ratio of active ingredient to lactose or the compression weight and using punches to suit.

The tablets may be film coated with suitable film forming materials, such as hydroxypropyl methylcellulose, using standard techniques. Alternatively the tablets may be sugar coated.

| CAPSULES | |
|---|---|
| | mg/capsule |
| Active ingredient | 25 |
| *Starch 1500 | 174 |
| Magnesium Stearate | 1.00 |
| Fill Weight | 200.00 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

| | mg/5 ml dose |
|---|---|
| Active Ingredient | 25 |
| Buffer | |
| Flavour | |
| Colour | as required |
| Preservative | |
| Thickening agent | |
| Sweetening agent | |
| Purified Water to | 5.00 ml |

The active ingredient, buffer, flavor, color, preservative, thickening agent and sweetening agent are dissolved in some water, the solution is adjusted to volume and mixed. The syrup produced is clarified by filtration.

EXAMPLE A (2S)-(+)-Glycidyl-3-nitrobenzenesulfonate

A 250 ml rounded bottom flask was charged with triethylamine (3.3 g, 4.5 ml, 32 mmol), R-glycidol (2.0 g, 27 mmol)(Arco Company, Newton Square, PA) and dichloromethane (50 ml) then cooled to 0° C. A solution of 3-nitrobenzenesulfonyl chloride (6.0 g, 27 mmol) in dichloromethane (40 ml) was added dropwise over a 5-minute period to the glycidol solution and the reaction mixture was stirred at 0° C. under $N_2$ for 3 hrs. The reaction mixture was poured into a separatory funnel and washed successively with 1N aqueous hydrochloric acid (90 ml), 5% aqueous sodium bicarbonate solution (90 ml), and saturated aqueous sodium chloride. The organic layer was separated, dried over anhydrous magnesium sulfate (10 g), filtered and concentrated in vacuo to yield (2S)-(+)-glycidyl-3-nitrobenzenesulfonate as a pale colored solid. Recrystallization from hexanes-/EtOAc (1:1, 50 ml) provided 5.89 g (83%) of pure (2S)-(+)-glycidyl-3-nitrobenzenesulfonate, m.p. 61°-63° C., $[\alpha]_D$+22.3° (c 0.41, chloroform), >95% optical purity.

EXAMPLE B (2R)-(-)-Glycidyl-3-nitrobenzenesulfonate

The procedure of Example A was repeated with S-glycidol (3.0 g, 40.5 mmol) (Arco Chemical Company, Newton Square, Pa.) in place of R-glycidol to provide 7.4 g (70%) of (2R)-(−)-glycidyl-3-nitrobenzenesulfonate, m.p.=61°-63° C. $[\alpha]_D$−21.5 (c0.97, chloroform).

EXAMPLE C (2R)-(+)-Glycidyl-2-cyanobenzene

A 250 ml round-bottomed flask was charged with 10.0 g (38.6 mmol) of (2S)-(+)-glycidyl-3-nitrobenzenesulfonate from Example A, 2-cyanophenol (4.60 g, 38.6 mmol) and anhydrous potassium carbonate (10.7 g, 77.2 mmol) in DMF (40 ml). The slurry was placed under an atmosphere of nitrogen at 65° C. for 4 hrs. The reaction mixture was cooled to 25° C. and poured into ice/water (100 g/75 ml). The precipitate was collected by suction filtration. The damp solid was dissolved in hot EtOAc (50 ml), dried over anhydrous magnesium sulfate (5 g), filtered and concentrated in vacuo to provide (2R)-(+)-glycidyl-2-cyanobenzene (5.27 g, 78%) as a solid. Recrystallization from EtOAc/hexane (30 ml/50 ml) provided 4.95 g (73%) of pure (2R)-(+)-glycidyl-2-cyanobenzene m.p. 88°-89° C., $[\alpha]_D$+25° (c 1.8, methanol).

EXAMPLE D (2S)-(-)-Glycidyl-2-cyanobenzene

The procedure of Example C was repeated with 4.0 g (15.4 mmol) of 2R-(−)-glycidyl-3-nitrobenzenesulfonate from Example B in place of the (2S) isomer to provide 2.3 g (85%) of (2S)-(−)-glycidyl-2-cyanobenzene as a crystalline solid, m.p. 88°-89° C., $[\alpha]_D$−24.4° (c 1.82, methanol).

EXAMPLE E (±)-4-[Cyano-(N-morpholino)methyl]anisole

A 5 L, four-necked round-bottomed flask equipped with a reflux condenser connected to a base trap, a glass rod air-driven stirrer, a thermometer and a gas inlet was charged with deionized water (2.4 L) and p-toluenesulfonic acid monohydrate (476.7 g, 2.51 mmol), then cooled to 10° C. Morpholine (323.4 g, 3.72 mmol) was added to the solution via an addition funnel at such a rate as not to allow the internal temperature to rise above 20° C. (15 min). A solution of p-anisaldehyde (169.4 g, 1.25 mmol) in methanol (160 ml) was added to the reaction mixture via an addition funnel over 10 min followed by the addition of solid potassium cyanide (161.7 g, 2.49 mmol). The slurry was warmed to 23° C. at which point it became a homogeneous solution. The solution was stirred for 4 hrs under an atmosphere of nitrogen, then cooled to 3° C. over 1 hour to induce crystallization. The white crystals were collected by suction filtration and dried in a vacuum oven at 25° C. (0.2 mm) to a constant weight to provide 252.3 g (88%) of pure (±)-4-[cyano-,(N-morpholino)methyl]anisole), m.p. 76°–78° C.

EXAMPLE F (±)-4-[1,3-Dicyano-2-methyl-3-(N-morpholino)propyl anisole

A 100 ml round-bottomed flask was charged with sodium hydride (60% dispersion, 2.0 g, 52 mmol) and tetrahydrofuran (anhydrous, 20 ml) then cooled to 0° C. under an atmosphere of nitrogen. To the slurry was added 10 g (43 mmol) of (±)-4-[cyano-(N-morpholino)-methyl]anisole from Example E in 2 g portions. The slurry was warmed to 23° C. and crotonitrile (5.8 g, 86 mmol) was added. The reaction mixture was stirred at 23° C. for 1 hr, poured into saturated aqueous ammonium chloride (40 ml) and extracted into EtOAc (2×50 ml). The combined EtOAc extracts were washed with saturated aqueous sodium chloride (75 ml), dried over anhydrous magnesium sulfate (5 g), filtered and concentrated in vacuo to provide 15.6 g of crude product, contaminated with crotonitrile. Recrystallization from hexanes/EtOAc ($\approx$1:2, 80 ml) provided 8.1 g (63%, two crops) of pure (±)-4-(1,3-dicyano-2-methyl-3-(N-morpholino)propyl]anisole, as a 2:1 mixture of diastereomers as determined by $^1$H NMR. Further purification or isolation of the diastereomers was not necessary.

EXAMPLE G (±)-3-(4'-Methoxybenzoyl)-3-methylpropanonitrile

A solution of 8.1 g (27 mmol) of (±)-4-[1,3-dicyano-2-methyl-3-(N-morpholino)propyl]anisole from Example F and 75% aqueous acetic acid (60 ml) in a 250 ml round-bottomed flash was stirred under an atmosphere of nitrogen at 100° C. for 3 hrs. The reaction mixture was cooled to 23° C., poured into water (300 ml) and extracted into dichloromethane (2×200 ml). The combined organic extracts were washed with saturated aqueous sodium bicarbonate (3×200 ml), dried over anhydrous magnesium sulfate (10 g), filtered and concentrated in vacuo to provide 5.1 g (100%) of pure (±)-3-(4-methocybenzoyl)-3-methylpropanonitrile. The sample was taken to the next step without further purification.

EXAMPLE H (±)-3-(4'-Hydroxybenzoyl)-3-methylpropanoic acid

A 5 L three-necked round-bottomed flask equipped with a reflux condenser connected to a base trap, a glass rod air driven stirrer, and a thermometer was charged with 192.0 g (0.946 mmol) of (±)-3-(4'-methoxybenzoyl)-3-methylpropionitrile from Example G and 48% aqueous hydrogen bromide (1.0 L). The reaction mixture was heated over 1 hr to 65° C. then stirred at this temperature for 45 min (this effected complete hydrolysis of the nitrile moiety). The reaction temperature was increased to 110° C. and the solution was stirred for 3.5 hrs to effect demethylation. The solution was cooled to 23° C., diluted with water (1250 ml), cooled to 0° C. and the pH was adjusted to pH 8.5 with sodium hydroxide pellets (325 g) and powdered sodium bicarbonate (50 g). The aqueous solution was washed with EtOAc (2.5 L), transferred to a 4 L beaker in an ice/water bath and the pH was adjusted to pH 2 with 36% concentrated hydrochloric acid (Fisher, 150 ml). The aqueous solution was extracted with EtOAc (1L) and the organic layer was separated. The aqueous solution was saturated with solid sodium chloride (200 g) then extracted again twice with EtOAc (1×1L, 1×0.5L). The combined organic extracts were dried over anhydrous magnesium sulfate (10 g), filtered and concentrated in vacuo to provide 154.0 g (78%) of pure (±)-3-(4'-hydroxybenzoyl)-3-methylpropanoic acid, m.p. 122°–126° C.

EXAMPLE I (±)-4,5-Dihydro-6-(4'-hydroxyphenyl -5-methyl-3(2H)-pyridazinone

A 1 l three-necked round-bottomed flask equipped with a condenser connected to a gas inlet, a glass rod air driven stirrer and a thermometer was charged with 63.8 g, (306 mmol) of (±)-3-(4'-hydroxybenzoyl)-3-methyl-propanoic acid from Example H and 2-propanol (400 ml) at 40° C. The solution was placed under an atmosphere of nitrogen and heated to 65° C. Then hydrazine monohydrate (45 ml, 2.2 mol) was added dropwise over 10 min. The reaction mixture was heated to 80-81° C. (reflux), stirred for 1 hour then slowly cooled to 3° C. over 1 hour with gentle stirring. The formed precipitate was collected by suction filtration, triturated in a 1 L beaker with deionized water (300 ml) at 23° C. for 2 hrs and collected by suction filtration. The solids were dried to constant weight in an air oven (90° C.) to provide 51.9 g (83.5%) of pure (±)-4,5-dihydro-6-(4'-hydroxyphenyl)-5-methyl-3(2H)-pyridazinone, m.p. 268°–273° C.

EXAMPLE J (±)-6-(4'-Butanoyloxyphenyl)-4,5-dihydro-5-methyl-3(2H)-pyridazinone A 100 ml round-bottomed flask was charged with pyridine (30 ml) and 7.10 g (34.8 mmol) of (±)-4,5-dihydro-6-(4'-hydroxyphenyl)-5-methyl-3(2H)-pyridazinone from Example I, then cooled to 0° C. under an atmosphere of nitrogen. Butanoyl chloride (4.10 g, 38.3 mmol) was added dropwise to the solution via syringe. The reaction mixture was stirred for 30 min at 0° C., warmed to 23° C. over 15 min then poured into 1N aqueous hydrochloric acid (400 ml). The aqueous solution was extracted with EtOAc (2×200 ml). The combined EtOAc extracts were successively washed with 5% aqueous sodium bicarbonate solution (300 ml), saturated aqueous sodium chloride (200 ml), dried over anhydrous magnesium sulfate (5 g), filtered and concentrated in vacuo to provide 9.8 g of crude product as a solid. Recrystallization from ethyl acetate/hexanes (2:1, 35 ml) yielded 7.61 g (80%) of pure (±)-6-(4'-butanoyloxyphenyl)-4,5-dihydro-5-methyl-3(2H)-pyridazinone as colorless needles, m.p. 112°–113° C.

EXAMPLE K (+)-6-(4'-Butanoyloxyphenyl)-4,5-dihydro-5S-methyl-3(2H)pyridazinone and (-)-4,5-Dihydro-6-(4'-hydroxyphenyl)-5R-methyl-3(2H)-pyridazinone A three-necked 1 L round-bottomed flask equipped with a pH electrode wired to a peristaltic pump, a 0.5 N aqueous sodium hydroxide reservoir and a magnetic stir bar was charged with 0.025 M, pH 7 potassium phosphate monobasic-sodium hydroxide buffer (450 ml) and lipase P-30 enzyme (3.9 g, 1600 units/mmol)(Amano International Enzyme Co. Inc., Troy, Va., U.S.A.). To this was added a solution of 20 g (73 mmol) of (±)-6-(4'-butanoyloxyphenyl)-4,5-dihydro-5-methyl-3(2H)-pyridazinone from Example J in tetrahydrofuran (150 ml) and the pH of the solution was adjusted pH 6.8 with glacial acetic acid (0.1 ml). The slurry was stirred at room temperature maintaining a pH range of pH 6.7 to pH 6.9 by the addition of 0.5 N aqueous sodium hydroxide using a pH electrode controlled peristaltic pump. The enzymatic hydrolysis was terminated after 0.55 equivalent of 0.5 N aqueous sodium hydroxide (80 ml, 8.2 mmol) was consumed (2.3 hr). The solution was transferred to a 2 L separatory funnel and extracted with EtOAc (3×500 ml). The combined EtOAc extracts were washed with saturated aqueous sodium chloride (700 ml), dried over anhydrous magnesium sulfate (10 g), and concentrated in vacuo to provide a mixture of (+)-6-(4'-butanoyloxyphenyl)-4,5-dihydro-6-(4'-hydroxyphenyl)-5-methyl-3(2H)-pyridazinone (19.7 g total). The solid was suspended in dichloromethane (300 ml) and triturated for 2 hrs with stirring. The butanoyl ester dissolved in dichloromethane but the 4'-hydroxy phenol was completely insoluble. The 9.25 g (62%, ≈53% optical purity) of (−)-enriched phenol was collected by suction filtration and dried at reduced pressure. The filtrate was concentrated in vacuo to provide 9.4 g of the butanoyl ester as an impure solid. The solid was dissolved in hot EtOAc/hexanes (1:1, 70 ml), filtered, then cooled slowly to 0° C. The crystals were collected by suction filtration and dried in vacuo to provide 5.25 g (26%) of pure (+)-6-(4'-butanoyloxyphenyl)-4,5-dihydro-5S-methyl-3(2H)-pyridazinone, m.p. 149°–150° C.; $[\alpha]_C +291.5°$ (c 0.20, methanol); >97% ee as determined by Eu(hfc)$_3$ chiral shift $^1$H NMR in deuterchloroform.

A portion of the above (−) enriched phenol was converted to (−) enriched butanoate by treatment with butanoyl chloride as in the above procedure of this Example K.

The ≈53% optical purity was based on the rotation of this sample $[[\alpha]_D -154°$ (c 0.30, methanol)]. The (−) enriched butyrate was recycled through the enzymatic process described above to yield after ca. 55% hydrolysis, (−) enriched phenol in ≈80% optical purity. This material was then treated with butanoyl chloride again and recycled through the process (≈55% hydrolysis) once again to provide the (−) enriched phenol in 99% optical purity. An overall yield of 15-18% was obtained for (−)-4,5-dihydro-6-(4'-hydroxyphenyl)-5R-methyl-3(2H)-pyridazinone, m.p. 262°–264° C.; $[\alpha]_D -398°$ (c 0.28, methanol), >99% ee as determined by chiral HPLC [250×4.6 mm 5μm spherical Ranin Cyclobond I (β) column.

EXAMPLE L (+)-4,5-Dihydro-6-(4'-hydroxyphenyl)-5S-methyl-3(2H)-pyridazinone

A 250 ml round-bottomed flask was charged with 5.25 g (19.2 mmol) of (+)-6-(4'butanoyloxyphenyl)-4,5-dihydro-5S-methyl-3(2H)-pyridazinone as prepared in Example K and methanol (90 ml). To this was added a solution of sodium hydroxide (3.84 g, 96 mmol) in deionized water (90 ml). The reaction mixture was stirred at 23° C. for 1 hour, then poured into deionized water (200 ml). The aqueous solution was adjusted to pH 2 with concentrated hydrochloric acid, then extracted with ethyl acetate (3×200 ml). The combined ethyl acetate extracts were washed with saturated aqueous sodium chloride (30 ml), dried over anhydrous magnesium sulfate (5 G), filtered and concentrated in vacuo to provide 3.74 g of a white powder. The solid was triturated with dichloromethane (50 ml), collected by suction filtration and dried vacuo (0.1 mm) to provide 3.64 (93%) of pure (+)-4,5-dihydro-6-(4'-hydroxyphenyl)-5S-methyl-3(2H)-pyridazinone, m.p. 262°"264° C.; $[\alpha]_D +395°$ (c 0.15, methanol); >99% ee as determined by chiral HPLC (250×4.6 mm 5 μm spherical Ranin Cyclobond I(β) column).

EXAMPLE M

Epimerization of (−)-Enriched 4.5-Dihydro-6-(4'-hydroxyphenyl)-5R-methyl-3(2H)-pyridazinone A 25 ml round-bottomed flask equipped with a stir bar and reflux condenser was charged with 0.10 g (0.49 mmol) of (−)-enriched-4,5-dihydro-6-(4'-hydroxyphenyl)-5-methyl-3(2H-pyridazinone (45% ee by chiral HPLC), 0.45 g (0.24 mmol) of p-toluenesulfonic acid monohydrate and methanol (15 ml). The solution was stirred under an atmosphere of nitrogen at reflux and epimerization of C-5 ° f the starting material was monitored by chiral HPLC (Cyclobond I, 75% pH 7 NaOH/KH$_2$PO$_4$ buffer, 25% methanol, 0.5 ml/min, lamba=280 nm). After 24 hrs, the starting material was nearly racemized. The solution was poured into water (30 ml) and extracted with EtOAc (3x35 ml). The combined EtOAc extracts were washed with saturated aqueous sodium chloride (50 ml), dried over anhydrous magnesium sulfate (5 g), filtered and concentrated in vacuo to provide 0.08 g (80%) of (±)-4,5-dihydro-6-(4'-hydroxyphenyl)-5-methyl-3(2H)-pyridazinone, m.p. 268°–273° C.; $[\alpha]_D -9.8°$ (c 0.24, methanol); 2.5% optical purity.

EXAMPLE N (±)-4,5-Dihydro-6-(4'-acetoxyphenyl)-5-methyl-3(2H)-pyridazinone

A 100 ml round-bottomed flask was charged with pyridine (34 ml) and 10 g (49 mmol) of (±)-4,5-dihydro-6-(4'-hydroxyphenyl)-5-methyl-3(2H)-pyridazinone, then cooled to 0° C. under an atmosphere of nitrogen. Acetyl chloride (4.2 g, 54 mmol) was added dropwise to the solution via syringe. The reaction mixture was stirred for 30 min at 0° C., warmed to 23° C. over 15 min then poured into IN aqueous hydrochloric acid (200 ml). The aqueous solution was extracted with EtOAc (2'200 ml). The combined EtOAc extracts were successively washed with 5% aqueous sodium bicarbonate (300 ml), saturated aqueous sodium chloride (200 ml), dried over anhydrous magnesium sulfate (5 g), filtered and concentrated in vacuo to a ≈50 ml. Hexanes (20 ml) were added and the solution cooled to 0° C. to effect crystallization. The crystals that formed were collected by suction filtration and dried in vacuo (0.1 mm) to provide 10.5 g (87%) of pure (±)-4,5-dihydro-6-(4'-acetoxyphenyl)-5-methyl-3(2H)-pyridazinone, m.p. 152°–153° C.

EXAMPLE O (−)-enriched-4,5-Dihydro-6-(4'-acetoxyphenyl)-5R-methyl-3(2H)-pyridazinone A 100 ml round-bottomed flask was charged with pyridine (15 ml) and 3.46 g (16.9 mmol) of (−)-enriched 4,5-dihydro-6-(4'-hydroxyphenyl-5-methyl-3(2H)-pyridazinone $[([\alpha]_D^{22} -179$ ° (c=0.09, methanol)](≈49% optical purity), then cooled to 0° C. under an atmosphere of nitrogen. Acetyl chloride (1.46 g, 18.6 mmol) was added dropwise to the solution via syringe. The reaction mixture was stirred for 30 min at 0° C., warmed to 23° C. over 15 min then poured into water (100 ml). The pH of the aqueous solution was adjusted to pH 2 with concentrated hydrochloric acid. The aqueous solution was extracted with EtOAc (2×100 ml). The combined EtOAc extracts were successively washed with 5% aqueous sodium bicarbonate (100 ml), saturated aqueous sodium chloride (100 ml), dried over anhydrous magnesium sulfate (5 g), filtered and concentrated in vacuo to a ≈15 ml. Hexanes (10 ml) were added and the solution was cooled to 0° C. to induce crystallization. The crystals that formed were collected by suction filtration and dried in vacuo (0.1 mm) to provide 4.08 g (98%) of (−)-enriched)4,5-dihydro-6-(4'-acetoxyphenyl)-5R-methyl-3(2H)-pyridazinone, m.p. 148°–150° C., $[\alpha]_D$ −163° (c 0.10, methanol); (≈49% optical purity).

EXAMPLE P (−)-4,5-Dihydro-6-(4'-hydroxyphenyl)-5R-methyl-3(2H)-pyridazinone

A three-necked 500 ml round-bottomed flask equipped with a pH electrode wired to a peristaltic pump, a 1N aqueous sodium hydroxide reservoir and a magnetic stir bar was charged with 0.025 M, pH 7 potassium phosphate monobasic-sodium hydroxide buffer (200 ml) and lipase P-30 enzyme (0.81 g, 1600 units/mmol) (Amano International Enzyme Co. In., Troy, Va., U.S.A.). To this mixture was added a solution of 4.0 g (16.2 mmol) of (−)-enriched 4,5-dihydro-6-(4'-acetoxyphenyl)-5R-methyl-3(2H)-pyridazi none $[\alpha]_D$ −163° (c 0.10, methanol); (≈49% optical purity) from Example 0 in tetrahydrofuran (80 ml). The pH of the solution was adjusted to pH 6.8 with glacial acetic acid (0.1 ml). The slurry was stirred at RT maintaining a pH range of 6.7 to pH 6.9 by the addition of 1 N aqueous sodium hydroxide using the pH electrode controlled peristaltic pump. The enzymatic hydrolysis was terminated after 0.45 equivalent of 1 N aqueous sodium hydroxide (7.3 ml, 7.3 mmol) was consumed (≈35 min). The solution was transferred to a 1 L separatory funnel, diluted with saturated aqueous sodium chloride (100 ml) then extracted with EtOAc (3×150 ml). The combined EtOAc extracts were washed with saturated aqueous sodium chloride (200 ml), dried over anhydrous magnesium sulfate (5 g), and concentrated in vacuo to provide a mixture of (+)-enriched starting material and (−)-enriched phenol title product. The mixture was triturated with chloroform (50° C., 100 ml), filtered and the precipitate washed with ethyl acetate (10 ml). The combined filtrates were concentrated in vacuo, triturated with dichloromethane (75 ml), filtered and concentrated in vacuo to provide 2.10 g (53%) of (+)-enriched starting material. The precipitate was triturated with ether (100 ml), collected by suction filtration and dried in vacuo (0.1 mm) to provide 1.35 g (41%) of (−)-4,5-dihydro-6-(4'-hydroxy-phenyl)-5R-methyl-3(2H)-pyridazinone, m.p. 262°–264° C.; o (c 0.12, methanol); >99% as determined by chiral HPLC (250 × 4.6 mm 5 μm spherical Ranin Cyclobond I($\beta$) column).

EXAMPLE O (+)-6-[4'-(Carboethoxymethylene)oxyphenyl]-4,5-dihydro-5S-methyl-3(2H)-pyridazinone A 100 ml round-bottomed flask equipped with a reflux condenser was charged with 1.0 g (4.9 mmol) of (+)-4,5-dihydro-6-(4'-hydroxyphenyl)-5S-methyl-3(2H)-pyridazinone, ethyl bromoacetate (0.90 g, 5.4 mmol), anhydrous potassium carbonate (1.0 g, 7.3 mmol) and acetronitrile (30 ml). The slurry was heated to reflux (81° C.) under an atmosphere of nitrogen then stirred for 4 hrs. The slurry was cooled to 23° C., poured into water (150 ml) and extracted with ethyl acetate (2×100 ml). The combined ethyl acetate extracts were washed with saturated aqueous sodium chloride (100 ml), dried over anhydrous magnesium sulfate (5 g), filtered and concentrated in vacuo to yield a crude solid. Purification by flash chromatography (hexanes/ethyl acetate, 1:1 to 1:3) provided 1.13 g (80%) of (+)-6-[4'-(carboethoxymethylene)oxyphenyl]-4,5-dihydro-5S-methyl-3(2H)-pyridazinone as a crystalline solid, m.p. 135°–136° C., $[\alpha]_D$ +285° (c 0.47, methanol).

EXAMPLE R (−)-6-[4'-Carboethoxymethylene1oxyphenyl]-4.5-dihydro-5R-methyl-3(2H)-pyridazinone The procedure of Example Q was repeated with 1.1 g (3.8 mmol) of (−)-4,5-dihydro-6-(4'-hydroxyphenyl)-5R-methyl-3(2H)-pyridazinone to yield 1.24 g (87%) of (−)-6-[4'-(carboethoxymethylene)oxyphenyl]-4,5-dihydro-5R-methyl3(2H)-pyridazinone as a crystalline solid, m.p. 135°–136° C.; (c 0.63, methanol).

EXAMPLE S (+)-6-4'-[N-(2-Amino-2-methylpropyl)carbamoylmethoxy1phenyl]-4,5-dihydro-5S-methyl-3(2H)-pyridazinone A 25 ml round-bottomed flask equipped with a reflux condenser was charged with 1.1 g (3.8 mmol) of (+)-6-[4'-(carboethoxymethylene)oxyphenyl]-4,5-dihydro-5S-methyl-3(2H)-pyridazinone from Example Q, 1,2-diamino-2methylpropane (0.68 g, 7.6 mmol) and methanol (10 ml). The solution was stirred at reflux (65° C.) under an atmosphere of nitrogen for 12 hrs. The reaction mixture was concentrated in vacuo and purified by flash chromatography (chloroform/methanol, 94:6) to provide 1.27 g (100%) of pure (+)-6-[4'-[N-(2-amino-2-methylpropyl)carbamoylmethoxy]phenyl]-4,5-dihydro-5S-methyl-3(2H)-pyridazinone as a colorless foam; $[\alpha]_D$ +212° (c 0.40, methanol).

EXAMPLE T (−)-6-4'-[N-(2-Amino-2-methylpropyl)carbamoylmethoxy1phenyl]-4,5-dihydro-5R-methyl-3(2H)-pyridazinone The procedure of Example S was repeated with 1.2 g (4.1 mmol) of (−)-6-[4'-(carboethoxymethylene)oxyphenyl]-4,5-dihydro-5R-methyl-3(2H)-pyridazinone to provide 1.32 g (96%) of (−)--6-[4'-[N-(2-amino-2-methylpropyl)carbamoylmethoxy]phenyl]-4,5-dihydro-5R-methyl-3(2H)-pyridazinone as a colorless foam; $[\alpha]_D$ −216° (c 0.19, methanol).

EXAMPLE U (−)-6-4,-[N-2-[2-Cyanophenoxy-2S-hydroxypropylamino1-2methylpropyl]carbamoylmethoxy1phenyl11-4.5-dihydro-5S-methyl-3(2H)-pyridazinone Monomaleate Salt A 25 ml round-bottomed flask equipped with a reflux condenser was charged with 0.48 g (2.7 mol) of (+)-6-[4'-{N-(2-amino-2-methylpropyl)carbamoylmethoxy]-phenyl]-4,5-dihydro-5S-methyl-3(2H)-pyridazinone of Example S, 0.48 (2.7 mmol) of (2R)-(+)-glycidyl-2-cyanobenzene of Example C and methanol (15 ml). The solution was stirred at reflux under an atmosphere of nitrogen for 12 hr, then concentrated in vacuo. Purification by flash column chromatography provided 0.95 g (69%) of (+)-6-[4'-[N-[2-[2-cyanophenoxy-2S-hydroxypropylamino]-2-methylpropyl]carbamoylmethoxy]-phenyl]-4,5-dihydro-5S-methyl-3(2H)pyridazinone as a colorless foam $[\alpha]_D + 131°$ (c 0.45, methanol). This foam was dissolved in ethyl acetate (35 ml), cooled to 0° C. and 0.11 M maleic acid in ether (27 ml, 3 mmol) was added. A precipitate formed immediately and oiled out in the bottom of the flask. The solution was carefully decanted. The solid was then dried in vacuo (0.1 mm) to yield a colorless foam. The foam was pulverized, washed with ether, and dried in vacuo to give 0.89 g (52%) of (+)-6-[4'-[N-[2-[2-cyanophenoxy-2S-hydroxypropylamino]2-methylpropyl]carbamoylmethoxy]-phenyl]-4,5-dihydro-5S-methyl-3(2H)-pyridazinone monomaleate salt as a colorless amorphous solid, m.p. 70°–73° C.; $[\alpha]_D + 109°$ (c 0.25, methanol), >95% de (by $^1$H NMR in deuterchloroform).

EXAMPLE V (−)-6-[4'-N-[2-[2-Cyanophenoxy-2S-hydroxypropylamino1-2methylpropyl]carbamoylmethoxy1-phenyl11-4.5-dihydro-5R-methyl-3(2H)-pyridazinone Monomaleate Salt The procedure of Example U was repeated with 0.73 g (2.2 mmol) of (−)-6-[4-[N-(2-amino-2-methylpropyl)-carbamoylmethoxy]phenyl]-4,5-dihydro-5R-methyl-3(2H)-pyridazinone of Example T and 0.38 g (2.2 mmol) of (2R)-(+)-glycidyl-2-cyanobenzene of Example C to yield 0.82 g (75%) of (−)-6-[4'-[N-[2-cyanophenoxy-2S-hydroxypropylamino]-2-methylpropyl]carbamoylmethoxy]phenyl]-4,5-dihydro-5R-methyl-3(2H)-pyridazinone; $[\alpha]_D - 145°$ (c 0.48, methanol). This was then converted into 0.76 g (55%) of (−)-6-[4'-[N-[2-[2-cyanophenoxy-2S-hydroxypropylamino-2-methyl-propyl]carbamoylmethoxy]phenyl]-4,5-dihydro-5R-methyl-3(2H)-pyridazinone monomaleate salt as a colorless amorphous solid, m.p. 70°–73° C.; $[\alpha]_D - 145°$ (c 0.38, methanol); >95% de (by $^1$H NMR in deuterchloroform.

EXAMPLE W (+)-6-[4'-[N-2-2-Cyanophenoxy-2R-hydroxypropylamino1-2-methyl-propyl]carbamoylmethoxy1-phenyl11-4,5-dihydro-5S-methyl-3(2H)-pyridazinone Monomaleate Salt The procedure of Example U was repeated with 1.25 g (3.8 mmol) of (+)-6-[4'-[N-(2-amino-2-methylpropyl)-carbamoylmethoxy]phenyl]-4,5-dihydro-5S-methyl-3(2H)-pyridazinone of Example S and 0.66 g (3.8 mmol) of 2S)-(−)-glycidyl-2-cyanobenzene of Example D to yield 1.36 g (72%) of (+)-6-[4'-[N-[2-[2-cyanophenoxy-2R-hydroxypropylamino]-2-methylpropyl]carbamoylmethoxy]phenyl]-4,5-dihydro-5S-methyl-3(2H)-pyridazinone. This was then converted to (+)-6-[4 [N-[2-[2-cyanophenoxy-2R-hydroxypropylamino]-2-methylpropyl]carbamoylmethoxy]-2-methylpropyl]carbamoylmethoxy]phenyl]-4,5-dihydro-5S-methyl-3(2H)-pyridazinone monomaleate salt as a colorless amorphous solid, m.p. 99°–103° C.; $[\alpha]_D + 137°$ C. (c 0.19, methanol), >95% de (by $^1$H NMR in deuterchloroform).

EXAMPLE X (−)-6-[4'-[N-[2-[2-Cyanophenoxy-2R-hydroxypropylamino1-2methylpropyl]carbamoylmethoxy1-phenyl11-4,5-dihydro-5R-methyl-3(2H)-pyridazinone Monomaleate Salt The procedure of Example W was repeated with 1.30 g (3.9 mmol) of (−)-6-[4'-[N-(2-amino-2-methylpropyl)-carbamoylmethoxy]phenyl]-4,5-dihydro-5R-methyl-3(2H)-pyridazinone of Example T and 0.68 (3.9 mmol) of (2S)-(−)-glycidyl-2-cyanobenzene of Example D to yield 1.46 g (74%) of (+)-6-[4'[N-[2-[2-cyanophenoxy-2R-hydroxypropyl-amino]-2-methylpropyl]carbamoylmethoxy]phenyl]-4,5-dihydro-5R-methyl-3(2H)-pyridazinone. This was then converted to 1.58 g (65%) of (−)-6-[4 -[N-[2-[2-cyanophenoxy-2R-hydroxypropylamino]-2-methylpropyl]carbamoylmethoxy]-phenyl]-4,5-dihydro-5R-methyl-3(2H)-pyridazinone monomaleate salt as a colorless amorphous solid, m.p. 101°–105° C.; $[\alpha]_D - 112°$ (c 0.30, methanol), >95% de (by $^1$H NMR in deuterchloroform).

EXAMPLE Y (±)-4,5-Dihydro-5-methyl-6-(4'-octanoylphenoxy)-3(2H)-pyridazinone A 500 ml round-bottomed flask was charged with chloroform (300 ml) and (±)-4,5-dihydro-6-(4-hydroxyphenyl)5-methyl-3(2H)-pyridazinone (3.0 g, 14.7 mmol), then cooled to 0° C. under an atmosphere of nitrogen. To the slurry was added octanoyl chloride (Aldrich, 2.63 g, 16.2 mmol) followed by triethyl amine (Fisher, 3.27 g, 32.3 mol). The slurry was warmed to 23° C. and stirred for 30 min. The slurry became homogeneous after 30 min. The solution was transferred to a separatory funnel, washed with saturated aqueous sodium bicarbonate (150 ml), then saturated aqueous sodium chloride. The organic solution was dried over magnesium sulfate (10 g), filtered and concentrated in vacuo to provide a solid (4.86 g). The solid was recrystallized from hexane (50 ml)/EtOAc (70 ml) to provide $^1$H NMR pure title product (50% yield). m.p. 90°–92° C.

EXAMPLE Z (-enriched)-4,5-Dihydro-6-(4'-hydroxyphenyl)-5-methyl3(2H)-pyridazinone A three-necked 0.25L round-bottomed flask equipped with a pH electrode wired to a peristatic pump, a 0.1N aqueous sodium hydroxide reservoir and a magnetic stir bar was charged with 0.025 M, pH 7 potassium phosphate monobasic-sodium hydroxide buffer (Fisher, 100 ml) and lipase P-30 (Amano, 0.35 g 1500 units/mol). To this was added a solution of (±)-4,5-dihydro-5-methyl-6(4'-octanoylphenoxy)-3(2H)-pyridazinone from Example Y (2.25 g, 6.81 mmol) in tetrahydrofuran (Mallinckridt, 35 ml). The pH of the solution was adjusted to 6.8 With glacial acetic acid (0.1 ml). The slurry was stirred at RT maintaining a pH range of 6.7 to 6.9 by the addition of 0.1N aqueous sodium hydroxide (pH electrode controlled peristatic pump (Cole-Parmer). The enzymatic hydrolysis was terminated after 0.4 equivalents of 0.1 N aqueous sodium hydroxide (27.2 ml, 2.72 mmol) was consumed ($\approx$35 min). The solution was transferred to a 1 L separatory funnel, diluted with saturated aqueous sodium chloride (100 ml) then extracted with EtOAc (3×150 ml). The combined EtOAc extracts were washed with saturated aqueous sodium chloride (200 ml), dried over anhydrous magnesium sulfate (5 g), and concentrated in vacuo to provide a mixture of starting material and the title product. Purification by flash chromatography (chloroform/methanol, 97:3 to 93:7) provided unreacted starting material (1.54 g, 68%) and the title product (0.50 g, 36% yield). $[\alpha]_D - 168°$ (c 0.215, methanol), 42% optical purity.

What is claimed is:

1. A process of resolving a mixture of 5R and 5S pyridazinone esters of the following formula (A):

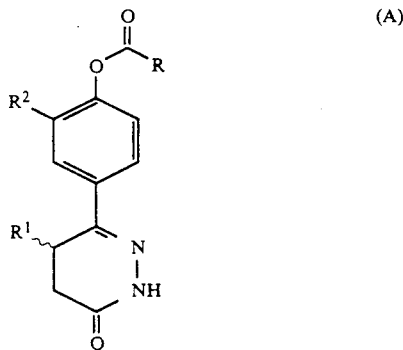

wherein:

$R^1$ represents lower alkyl;

$R^2$ represents hydrogen, halogen, trifluoromethyl, cyano, lower alkyl or loweralkyloxy; and R represents alkyl, which comprises reacting said ester mixture with a hydrolytic lipase enzyme and recovering i) a mixture of esters of formula (A) optically enriched of formula (A) in one of the 5R or 5S enantiomers and ii) a mixture of the phenols of the following formula (B) optically enriched in the other of the 5R or 5S enantiomers:

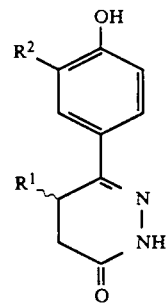

2. The process of claim 1, wherein said mixture of esters (A) is enriched in the 5S ester and said mixture of phenols (B) is enriched in the 5R phenol.

3. The process of claim 1, wherein said reaction is conducted to about 40 to 60% completion.

4. The process of claim 1, wherein said reaction is conducted in about a ratio of about 100 to 10,000 units of enzyme per millimole of ester mixture (A).

5. The process of claim 1, wherein said reaction is conducted at a temperature of about 0° to 40° C.

6. The process of claim 1, wherein said reaction is conducted in an aqueous solution with an organic cosolvent.

7. The process of claim 6, wherein said co-solvent is an ether, an alkanol, a ketone or a halogenated hydrocarbon.

8. The process of claim 1, wherein said hydrolytic enzyme is lipase derived from Pseudomonas.

9. The process of claim 1, wherein R is alkyl of less than 20 carbons.

10. The process of claim 1, wherein R is alkyl of less than 4 carbons.

11. The process of claim 1, wherein $R^2$ is hydrogen.

12. The process of claim 1, wherein $R^1$ is methyl.

13. The process of claim 1, wherein said mixture (A) is derived from a mixture of approximately the same optical purity of phenols of the formula (B).

14. The process of claim 1, wherein said phenol mixture of formula (B) recovered in said reaction is further optically purified by esterification with a source of —C(O)R and reacted again with a hydrolytic enzyme to yield a mixture of phenols (B) having a greater optical purity.

15. The process of claim 1, wherein said ester mixture of formula (A) recovered in said reaction is racemized by chemical hydrolysis to recover the corresponding phenol mixture of formula (B) followed by acid catalyzed epimerization at C-5.

* * * * *